United States Patent
Hatch et al.

(10) Patent No.: US 10,988,723 B1
(45) Date of Patent: Apr. 27, 2021

(54) MODULAR ASSEMBLIES AND SYSTEMS FOR CELL CULTURES AND METHODS THEREOF

(71) Applicant: National Technology & Engineering Solutions of Sandia, LLC, Albuquerque, NM (US)

(72) Inventors: Anson Hatch, Tracy, CA (US); Vinay Abhyankar, Keller, TX (US); Chung-Yan Koh, Dublin, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 549 days.

(21) Appl. No.: 15/273,408

(22) Filed: Sep. 22, 2016

Related U.S. Application Data

(60) Provisional application No. 62/222,597, filed on Sep. 23, 2015.

(51) Int. Cl.
| | |
|---|---|
| *C12M 3/06* | (2006.01) |
| *C12M 3/00* | (2006.01) |
| *C12M 1/12* | (2006.01) |
| *C12M 1/00* | (2006.01) |

(52) U.S. Cl.
CPC ............ *C12M 23/44* (2013.01); *C12M 23/16* (2013.01); *C12M 23/46* (2013.01); *C12M 25/02* (2013.01); *C12M 29/10* (2013.01)

(58) Field of Classification Search
None
See application file for complete search history.

(56) References Cited

U.S. PATENT DOCUMENTS

| | | | |
|---|---|---|---|
| 6,284,497 B1 | 9/2001 | Sabanayagam et al. | |
| 6,329,195 B1 * | 12/2001 | Pfaller | C12M 23/24 435/287.1 |
| 6,408,884 B1 | 6/2002 | Kamholz et al. | |
| 6,415,821 B2 | 7/2002 | Kamholz et al. | |
| 6,541,213 B1 | 4/2003 | Weigl et al. | |
| 6,743,399 B1 | 6/2004 | Weigl et al. | |
| 6,811,752 B2 * | 11/2004 | Barbera-Guillem | B01L 3/50853 422/503 |
| 7,141,429 B2 | 11/2006 | Munson et al. | |
| 7,271,007 B2 | 9/2007 | Weigl et al. | |
| 7,470,403 B2 | 12/2008 | Beebe et al. | |

(Continued)

OTHER PUBLICATIONS

Toepke et al. (PDMS absorption of small molecules and consequences in microfluidic applications. Lab Chip, 2006, 6, 1484-1486).*

(Continued)

*Primary Examiner* — William H. Beisner
(74) *Attorney, Agent, or Firm* — Helen S Baca

(57) ABSTRACT

The present invention relates to modular assemblies and systems for conducting cell analyses. In particular embodiments, an assembly has micron-scale fluidic structures, thereby minimizing sample use, and possesses a modular architecture that facilitates disassembly of the apparatus. Thus, one such modular assembly facilitates on-chip cell growth and on-chip assays; and then, as needed, the assembly can be disassembled to provide direct access to the cells that were incubated and treated within the chip. Methods of making and using such assemblies, as well as systems thereof, are further described herein.

22 Claims, 36 Drawing Sheets

Specification includes a Sequence Listing.

(56) References Cited

U.S. PATENT DOCUMENTS

| | | | |
|---|---|---|---|
| 7,828,948 B1 | 11/2010 | Hatch et al. | |
| 8,047,829 B1 | 11/2011 | Sommer et al. | |
| 8,163,154 B1 | 4/2012 | Hatch et al. | |
| 8,257,964 B2 | 9/2012 | Hung et al. | |
| 8,329,016 B1 | 12/2012 | Sommer et al. | |
| 8,394,312 B1 | 3/2013 | Sommer et al. | |
| 8,703,058 B1 | 4/2014 | Hatch et al. | |
| 8,728,290 B1 | 5/2014 | Sommer et al. | |
| 8,748,180 B2 | 6/2014 | Shuler et al. | |
| 8,871,496 B1 | 10/2014 | Sommer et al. | |
| 8,945,914 B1 | 2/2015 | Schaff et al. | |
| 8,962,346 B2 | 2/2015 | Schaff et al. | |
| 9,005,147 B2 | 4/2015 | Sommer et al. | |
| 9,201,069 B2 | 12/2015 | Hatch et al. | |
| 9,304,128 B1 | 4/2016 | Koh et al. | |
| 9,304,129 B2 | 4/2016 | Schaff et al. | |
| 9,409,357 B1 | 8/2016 | Sommer et al. | |
| 2004/0242469 A1* | 12/2004 | Lee | A61K 38/10 424/93.1 |
| 2009/0098659 A1* | 4/2009 | Abhyankar | B01L 3/5027 436/180 |
| 2012/0135452 A1* | 5/2012 | Shuler | C12M 23/16 435/29 |
| 2012/0214189 A1 | 8/2012 | Shuler et al. | |
| 2012/0231976 A1 | 9/2012 | Wu et al. | |
| 2012/0315694 A1 | 12/2012 | Cho et al. | |
| 2013/0295551 A1* | 11/2013 | Eddington | A01N 1/0247 435/1.2 |
| 2014/0178992 A1* | 6/2014 | Nakashima | C12M 23/12 435/375 |
| 2016/0326477 A1* | 11/2016 | Fernandez-Alcon | C12M 23/16 |

OTHER PUBLICATIONS

Esch et al. (Multi-cellular 3D human primary liver cell culture elevates metabolic activity udner fluidic dlow. Lab Chip 2015, 15 2269).*
U.S. Appl. No. 12/182,755, filed Jul. 30, 2008, Hatch.
U.S. Appl. No. 12/900,276, filed Oct. 7, 2010, Renzi et al.
U.S. Appl. No. 13/423,008, filed Mar. 16, 2012, Koh et al.
U.S. Appl. No. 13/941,186, filed Jul. 12, 2013, Koh et al.
U.S. Appl. No. 14/090,040, filed Nov. 26, 2013, Koh et al.
U.S. Appl. No. 14/546,876, filed Nov. 18, 2014, Koh et al.
U.S. Appl. No. 14/957,405, filed Dec. 2, 2015, Koh et al.
U.S. Appl. No. 15/008,285, filed Jan. 27, 2016, Meagher et al.
U.S. Appl. No. 15/153,519, filed May 12, 2016, Hatch et al.
Abbott NJ et al., "Astrocyte-endothelial interactions at the blood-brain barrier," *Nat. Rev. Neurosci.* 2006;7(1):41-53.
Abhyankar et al., "A Reversibly Sealed, Easy Access, Modular (SEAM) Microfluidic Architecture to Establish In Vitro Tissue Interfaces," *PLOS One* 2016; 11(5): e0156341 (20 pp.).
Andonegui G et al., "Endothelium-derived Toll-like receptor-4 is the key molecule in LPS-induced neutrophil sequestration into lungs," *J. Clin. Invest.* 2003;111(7):1011-20.
Badylak SF et al., "Extracellular matrix as a biological scaffold material: Structure and function," *Acta Biomater.* 2009;5(1):1-13.
Beebe DJ et al., "Microfluidic tectonics: a comprehensive construction platform for microfluidic systems," *Proc. Nat'l Acad. Sci. USA* 2000;97(25):13488-93.
Beniash E et al., "Self-assembling peptide amphiphile nanofiber matrices for cell entrapment," *Acta Biomater.* 2005;1:387-97.
Berry SM et al., "Streamlining gene expression analysis: integration of co-culture and mRNA purification," *Integr. Biol. (Camb.)* 2014;6(2):224-31.
Bhatia SN et al., "Microfluidic organs-on-chips," *Nat. Biotechnol.* 2014;32(8):760-72.
Bhattacharya J et al., "Regulation and repair of the alveolar-capillary barrier in acute lung injury," *Annu. Rev. Physiol.* 2013;75:593-615.

Bruggeman LA et al., "A cell culture system for the structure and hydrogel properties of basement membranes; Application to capillary walls," *Cell. Mol. Bioeng.* 2012;5(2):194-204.
Byun CK et al., "Pumps for microfluidic cell culture," *Electrophoresis* 2014;35(2-3):245-57.
Capito RM et al., "Self-assembly of large and small molecules into hierarchically ordered sacs and membranes," *Science* 2008;319:1812-6.
Carvajal D et al., "Physical properties of hierarchically ordered self-assembled planar and spherical membranes," *Soft Matter* 2010;6:1816-23.
Chow LW et al., "A bioactive self-assembled membrane to promote angiogenesis," *Biomaterials* 2011;32:1574-82.
Cui H et al., "Self-assembly of peptide amphiphiles: from molecules to nanostructures to biomaterials," *Biopolymers* 2010;94(1):1-18.
Domansky K et al., "Clear castable polyurethane elastomer for fabrication of microfluidic devices," *Lab Chip* 2013;13(19):3956-64.
Duffy DC et al., "Rapid prototyping of microfluidic systems in poly(dimethylsiloxane)," *Anal. Chem.* 1998;70(23):4974-84.
Engler AJ et al., "Extracellular matrix elasticity directs stem cell differentiation," *J. Musculoskelet. Neuronal Interact.* 2007;7(4):335.
Engler AJ et al., "Matrix elasticity directs stem cell lineage specification," *Cell* 2006;126(4):677-89.
Engler AJ et al., "Myotubes differentiate optimally on substrates with tissue-like stiffness: pathological implications for soft or stiff microenvironments," *J. Cell. Biol.* 2004;166(6):877-87.
Esch MB et al., "How multi-organ microdevices can help foster drug development," *Adv. Drug Deliv. Rev.* 2014;69-70:158-69.
Esch MB et al., "Multi-cellular 3D human primary liver cell culture elevates metabolic activity under fluidic flow," *Lab Chip* 2015;15:2269-77.
Esch MB et al., "On chip porous polymer membranes for integration of gastrointestinal tract epithelium with microfluidic 'body-on-a-chip' devices," *Biomed. Microdevices* 2012;14(5):895-906.
Fahlman A et al., "Static inflation and deflation pressure-volume curves from excised lungs of marine mammals," *J. Exp. Biol.* 2011;214(Pt 22):3822-8.
Frohlich EM et al., "Topographically-patterned porous membranes in a microfluidic device as an in vitro model of renal reabsorptive barriers," *Lab Chip* 2013;13(12):2311-9.
Geetha T et al., "Nerve growth factor receptor TrkA, a new receptor in insulin signaling pathway in PC12 cells," *J. Biol. Chem.* 2013;288(33):23807-13.
Ghaemmaghami AM et al., "Biomimetic tissues on a chip for drug discovery," *Drug Discov. Today* 2012;17(3-4):173-81.
Harris RS, "Pressure-volume curves of the respiratory system," *Respir. Care* 2005;50(1):78-99.
Hartgerink JD et al., "Peptide-amphiphile nanofibers: a versatile scaffold for the preparation of self-assembling materials," *Proc. Nat'l Acad. Sci. USA* 2002;99:5133-8.
Hartgerink JD et al., "Self-assembly and mineralization of peptide-amphiphile nanofibers," *Science* 2001;294:1684-8.
Hatch AV et al., "Integrated preconcentration SDS-PAGE of proteins in microchips using photopatterned cross-linked polyacrylamide gels," *Anal. Chem.* 2006;78(14):4976-84.
Herr AE et al., "Microfluidic immunoassays as rapid saliva-based clinical diagnostics," *Proc. Nat'l Acad. Sci. USA* 2007;104(13):5268-73.
Huh D et al., "A human disease model of drug toxicity-induced pulmonary edema in a lung-on-a-chip microdevice," *Sci. Transl. Med.* 2012;4(159):159ra147.
Huh D et al., "From 3D cell culture to organs-on-chips," *Trends Cell. Biol.* 2011;21(12):745-54.
Huh D et al., "Microengineered physiological biomimicry: organs-on-chips," *Lab Chip* 2012;12(12):2156-64.
Huh D et al., "Reconstituting organ-level lung functions on a chip," *Science* 2010;328(5986):1662-8.
Huynh J et al., "Substrate stiffness regulates PDGF-induced circular dorsal ruffle formation through MLCK," *Cell. Mol. Bioeng.* Jun. 2013;6(2): 16 pp.

(56) References Cited

OTHER PUBLICATIONS

Ismagilov RF et al., "Microfluidic arrays of fluid-fluid diffusional contacts as detection elements and combinatorial tools," *Anal. Chem.* 2001;73(21):5207-13.

Kang E et al., "Large-scale, ultrapliable, and free-standing nanomembranes," *Adv. Mater.* 2013;25(15):2167-73.

Kim HJ et al., "Human gut-on-a-chip inhabited by microbial flora that experiences intestinal peristalsis-like motions and flow," *Lab Chip* 2012;12(12):2165-74.

Kim T et al., "A pumpless cell culture chip with the constant medium perfusion-rate maintained by balanced droplet dispensing," *Lab Chip* 2011;11:1825-30.

Kim T et al., "On-chip three-dimensional tumor spheroid formation and pump-less perfusion culture using gravity-driven cell aggregation and balanced droplet dispensing," *Biomicrofluidics* 2012;6:034107 (10 pp.).

Lee DW et al., "A pumpless perfusion cell culture cap with two parallel channel layers keeping the flow rate constant," *Biotechnol. Prog.* 2012;28(6):1466-71.

Licatalosi DD et al., "RNA processing and its regulation: global insights into biological networks," *Nat. Rev. Genet.* 2010;11(1):75-87.

Lin CC et al., "Microfluidic immunoassays," *J. Assoc. Lab. Automat.* 2010;15:253-74.

Lu JT et al., "Thin collagen film scaffolds for retinal epithelial cell culture," *Biomaterials* 2007;28(8):1486-94.

Mata A et al., "Bone regeneration mediated by biomimetic mineralization of a nanofiber matrix," *Biomaterials* 2010;31(23):6004-12.

Miller JJ et al., "Lift-off of large-scale ultrathin nanomembranes," *J. Micromech. Microeng.* 2015; 25(1):015011.

Nan L et al., "Emerging microfluidic devices for cell lysis: a review," *Lab Chip* 2014;14(6):1060-73.

Nakayama M et al., "A novel RING-H2 motif protein downregulated by axotomy: its characteristic localization at the postsynaptic density of axosomatic synapse," *J. Neurosci.* 1995;15(7 Pt 2):5238-48.

Rehfeldt F et al., "Cell responses to the mechanochemical microenvironment—implications for regenerative medicine and drug delivery," *Adv. Drug Deliv. Rev.* 2007;59(13):1329-39.

Richert L et al., "Elasticity of native and cross-linked polyelectrolyte multilayer films," *Biomacromolecules* 2004;5(5):1908-16.

Ruoslahti E, "Brain extracellular matrix," *Glycobiology* 1996;6(5):489-92.

Silva GA et al., "Selective differentiation of neural progenitor cells by high-epitope density nanofibers," *Science* 2004;303(5662):1352-5.

Soofi SS et al., "The elastic modulus of Matrigel as determined by atomic force microscopy," *J. Struct. Biol.* 2009;167: 216-9.

Storrie H et al., "Supramolecular crafting of cell adhesion," *Biomaterials* 2007;28(31):4608-18.

Toepke MW et al., "PDMS absorption of small molecules and consequences in microfluidic applications," *Lab Chip* 2006;6(12):1484-6.

Van Heirstraeten L et al., "Integrated DNA and RNA extraction and purification on an automated microfluidic cassette from bacterial and viral pathogens causing community-acquired lower respiratory tract infections," *Lab Chip* 2014;14(9):1519-26.

Verbist B et al., "Using transcriptomics to guide lead optimization in drug discovery projects: Lessons learned from the QSTAR project," *Drug Discov. Today* 2015;20(5):505-13.

Verhulsel M et al., "A review of microfabrication and hydrogel engineering for micro-organs on chips," *Biomaterials* 2014;35(6):1816-32.

Wang JD et al., "Quantitative analysis of molecular absorption into PDMS microfluidic channels," *Ann. Biomed. Eng.* 2012;40(9):1862-73.

Wang TW et al., "Development of hyaluronic acid-based scaffolds for brain tissue engineering," *Acta Biomater.* 2009;5(7):2371-84.

Zhang J et al., "c-fos regulates neuronal excitability and survival," *Nat. Genet.* 2002;30(4):416-20.

Zhang P et al., "Innate immunity and pulmonary host defense," *Immunol. Rev.* 2000;173:39-51.

Zhu X et al., "Arrays of horizontally-oriented mini-reservoirs generate steady microfluidic flows for continuous perfusion cell culture and gradient generation," *Analyst* 2004;129(11):1026-31.

\* cited by examiner

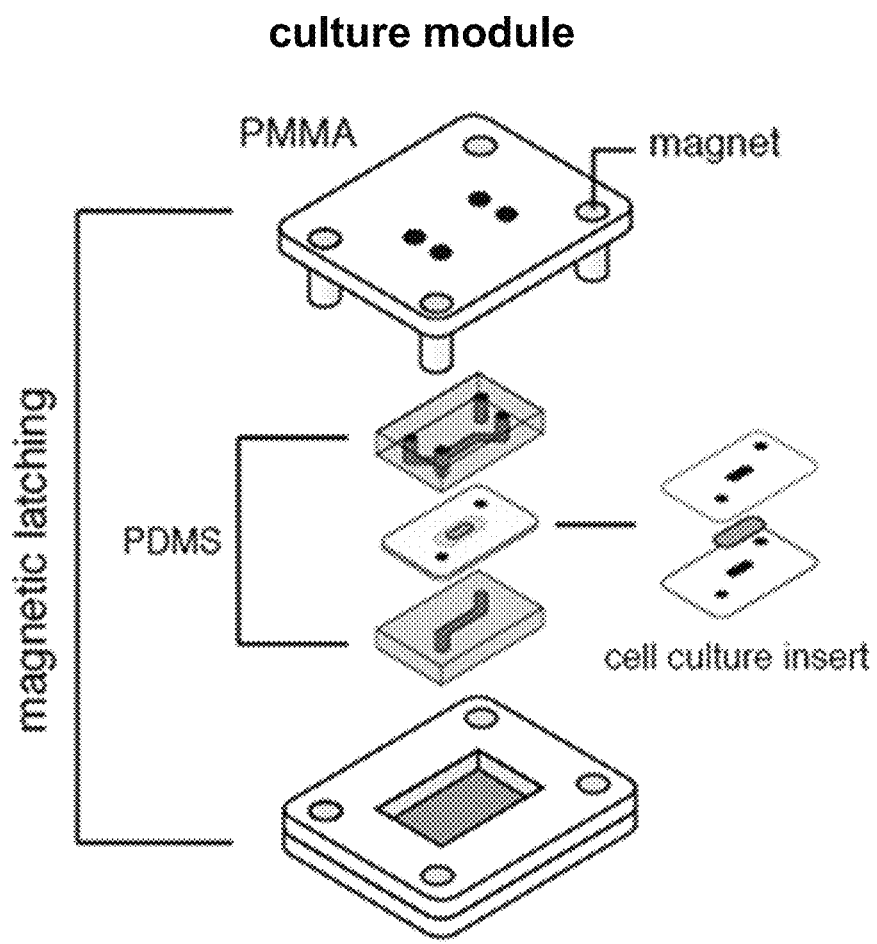
FIG. 10A
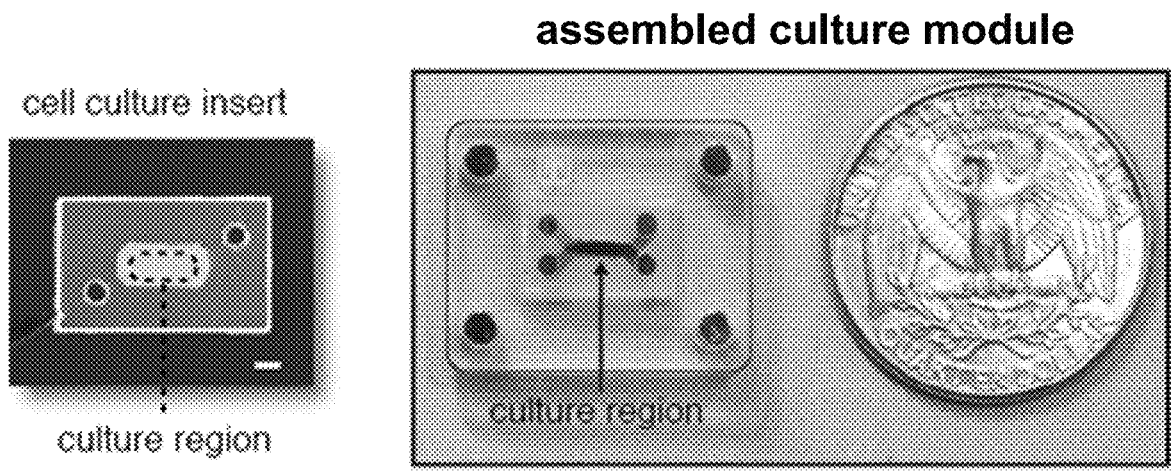
FIG. 10B
FIG. 10C gravity fed perfusion $\Delta P_{aa-bb} = \rho g \Delta z$ $Q_{avg} = \Delta P_{aa-bb} R^{-1}$

MODULAR ASSEMBLIES AND SYSTEMS FOR CELL CULTURES AND METHODS THEREOF

CROSS-REFERENCE TO RELATED APPLICATION

This application claims the benefit of U.S. Provisional Application No. 62/222,597, filed Sep. 23, 2015, which is hereby incorporated by reference in its entirety.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

REFERENCE TO A SEQUENCE LISTING APPENDIX

A sequence listing appendix including an ASCII formatted file accompanies this application. The appendix includes a file named "SD12792_1_Sequence_Listing_ST25.txt," created on Sep. 20, 2016 (size of 3.91 kilobytes), which is hereby incorporated by reference in its entirety.

FIELD OF THE INVENTION

The present invention relates to modular assemblies and systems for conducting cell analyses, as well as methods thereof. In particular embodiments, an assembly has micron-scale fluidic structures, thereby minimizing sample use, and possesses a modular architecture that facilitates disassembly of the apparatus.

BACKGROUND OF THE INVENTION

Complex cell interactions provide key insights into organ and tissue function. Yet, such interactions are difficult to elucidate in vivo. In vitro platforms are an attractive alternative that simplifies testing, while providing viable mechanistic correlations that can be later confirmed by way of in vivo testing. Various monolithic in vitro platforms have been developed, in which the components of the platform are sealed together, thereby providing limited direct access to cells that were grown or tested within the platforms. Direct access, at times, would be helpful, e.g., such as to conduct additional laboratory-scale testing on a certain cell colonies or subpopulations of cells. In addition, platforms having simplified architectures are desired, thereby allowing the platforms to be employed without the use of specialized training or complicated equipment. Accordingly, there is a need for simplified platforms that can be used to study cell interactions, while also providing direct access to such cell populations.

SUMMARY OF THE INVENTION

The present invention relates to modular assemblies and systems configured to grow cells on-chip (e.g., including 3D assemblages of cells) and to provide access to such cells. In particular, the modular assembly employs a transferrable culture insert having a cell culture membrane on which cells can be deposited, as well as a handling layer that facilitates removing or transferring the insert from the assembly. In addition, the modular assembly includes a detachable housing set configured to be assembled around the insert. After use, this housing set can be easily disassembled, and, if desired, another housing set configured for another use (e.g., configured for conducting a cell assay) can be assembled around the insert containing the cells. In this way, the present invention also encompasses modular systems, which includes a plurality of housing sets, where each housing set is configured for a different use (e.g., for use as a seeding module, a culture module, a perfusion module, etc.), but each set is also configured to be assembled around the same transferrable insert. In this way, different modalities (or biochemical techniques) can be implemented with the same cells on the same insert by arranging different housing sets around the transferrable insert.

In some situations, to minimize leakage or contamination, the modular assembly can include one or more sealing layers disposed between the insert and the housing. Such sealing layers can include one or more adhesive layers (e.g., disposed on the housing in order to, e.g., facilitate handling and assembly of the module), one or more channels (e.g., to provide fluidic communication between one or more access ports, reservoirs, cell culture membranes, etc.), and one or more vias (e.g., to provide fluidic communication between different layers within the assembly).

In a first aspect, the present invention features a modular assembly including: a transferrable cell culture insert, where the transferrable insert includes a handling layer, an aperture disposed within the handling layer, and a cell culture membrane disposed within or in proximity to the aperture; a top housing including one or more access ports, where at least one access port is in fluidic communication with the cell culture membrane; and a bottom housing, where the top and bottom housing are configured to accommodate the transferrable insert and to be reversibly attached, thereby facilitating transfer of the transferrable insert.

In a second aspect, the present invention features a module system including: a transferrable cell culture insert (e.g., including a handling layer, an aperture disposed within the handling layer, and a cell culture membrane disposed within or in proximity to the aperture); a detachable first housing set (e.g., including a first top housing including one or more access ports, where at least one access port is configured to be in fluidic communication with the cell culture membrane; and a first bottom housing, where the first top housing and the first bottom housing are configured to accommodate the transferrable insert and to be reversibly attached, thereby facilitating transfer of the transferrable insert); a top sealing layer (e.g., configured to be affixed to a top planar surface of the transferrable insert, where the top sealing layer is further configured to be disposed between the first top housing and the transferrable insert); and a bottom sealing layer (e.g., configured to be affixed to a bottom planar surface of the transferrable insert, where the bottom sealing layer is further configured to be disposed between the transferrable insert and the first bottom housing).

In some embodiments, the assembly and/or the system further includes one or more fasteners disposed within the top housing (e.g., the first top housing), within the bottom housing (e.g., the first bottom housing), and/or between the top and bottom housing (e.g., the first top housing and first bottom housing). In further embodiments, one or more fasteners includes one or more adhesive layers, where at least one adhesive layer is disposed between the top housing and the transferrable insert and/or between the transferrable insert and the bottom housing. In other embodiments, at least one adhesive layer includes a reversible sealing material.

In some embodiments, the top housing, the bottom housing, the one or more adhesive layers, and/or the handling layer further includes one or more alignment features.

In some embodiments, the top housing (e.g., first top housing) further includes one or more first fasteners and the bottom housing (e.g., first bottom housing) further includes one or more second fasteners. In further embodiments, at least one first fastener and at least one second fastener are configured to be reversibly attached to each other. In other embodiments, the top and bottom housing are configured to be detached, thereby facilitating transfer of the transferrable insert.

In some embodiments, the bottom housing further includes a recess configured to accommodate the transferrable insert. In other embodiments, the transferrable insert includes one or more vias configured to be aligned with any one or more vias present in the assembly. In yet other embodiments, the top sealing layer and/or the bottom sealing layer includes one or more vias configured to be aligned with one or more vias present in the transferrable insert.

In further embodiments, the assembly and/or system includes a top sealing layer configured to be affixed to a top planar surface of the transferrable insert; and a bottom sealing layer configured to be affixed to a bottom planar surface of the transferrable insert. In some embodiments, an optional recess within the bottom housing is further configured to accommodate the transferrable insert affixed to the top sealing layer and to the bottom sealing layer.

In other embodiments, the top sealing layer and the bottom sealing layer are configured to be reversibly affixed to the transferrable insert and to form a seal between the transferrable insert, the top housing, and the bottom housing. In some embodiments, the top sealing layer and/or the bottom sealing layer includes a channel disposed therein (e.g., the channel is configured to be in fluidic communication with at least one access port in the top housing and/or the bottom housing; and/or the channel is disposed above or below the cell culture membrane of the transferrable insert). In yet other embodiments, the channel in the top sealing layer is in fluidic communication with a top surface of the cell culture membrane, and/or the channel in the bottom sealing layer is in fluidic communication with a bottom surface of the cell culture membrane.

In some embodiments, the top sealing layer further includes a via configured to be in fluidic communication with the channel of the top sealing layer and at least one access port in the top housing. In other embodiments, the top sealing layer includes a channel disposed between two vias, the transferrable insert includes at least two vias, and/or the bottom sealing layer includes a channel disposed between two vias. In yet other embodiments, at least one via of the top sealing layer is in fluidic communication with at least one via of the transferrable insert, and/or at least one via in the bottom sealing layer is in fluidic communication with at least one via of the transferrable insert.

In further embodiments, the assembly and/or system includes a fluidics layer (e.g., including a channel and a via, where the fluidics layer is configured to be disposed above the top sealing layer and/or where the via of the fluidics layer is configured to be in fluidic communication with at least one access port of the top housing). In some embodiments, the via of the fluidics layer is further configured to be in fluidic communication with a channel disposed within the top sealing layer.

In some embodiments, at least one first fastener is arranged in the top housing configured to be in contact with at least one second fastener arranged in the bottom housing. In other embodiments, at least one first fastener and/or at least one second fastener includes a magnetic fastener, an adhesive fastener, a mechanical fastener, a clamp, a mating member, a clip, and/or a closure.

In some embodiments, the cell culture membrane (e.g., of the assembly and/or the transferrable insert) includes a porous substrate. In other embodiments, the handling layer or a portion thereof includes a porous substrate. In some embodiment, the handling layer is porous or is porous within a cross-section around a periphery of the aperture. In yet other embodiments, the cell culture membrane includes a polymer membrane (e.g., including a plurality of nanofibers). In some embodiments, at least one access port is configured to be in fluidic communication with the cell culture membrane.

In some embodiments, the transferrable insert includes a laminated structure. The laminated structure can include, e.g., a top handling layer having a first aperture, a bottom handling layer having a second aperture, and a cell culture membrane disposed between the top and bottom handling layers and positioned between the first and second apertures. In other embodiments, the top handling layer, the cell culture membrane, and/or the bottom handling layer are positioned and laminated. In yet other embodiments, the transferrable insert includes a rim disposed around a periphery of the aperture within the handling layer, where the cell culture membrane is configured to be tethered to the rim.

In some embodiments, the assembly and/or system further includes a layer of adhesive disposed between the top housing and the transferrable insert and/or between the bottom housing and the transferrable insert. In other embodiments, the assembly further includes a layer of adhesive disposed between the top housing and the top sealing layer, between the top sealing layer and the transferrable insert, between the transferrable insert and the bottom sealing layer, and/or between the bottom sealing layer and the bottom housing.

In further embodiments, the assembly and/or system includes a perfusion module (e.g., configured to be reversibly attached to the top housing and configured to be in fluidic communication with at least one access port of the top housing). In other embodiments, the perfusion module includes a top reservoir layer including a first reservoir; an isolation layer including a first via configured to be in fluidic communication with the first reservoir; a resistance layer including at least two vias and a channel disposed between the at least two vias, where one of the at least two vias is configured to be in fluidic communication with the first via of the isolation layer; and a bottom reservoir layer including a second reservoir and a second via, where the second via is configured to be in fluidic communication with at least one access port of the top housing.

In some embodiments, the assembly and/or system includes the housing set (e.g., first housing set) that is configured as a seeding module. In other embodiments, the top housing includes a reservoir configured to be in fluidic communication with a top surface of the cell culture membrane, and the bottom housing includes a channel configured to be in fluidic communication with a bottom surface of the cell culture membrane. In other embodiments, at least one access port of the top housing is configured to be in fluidic communication with the channel of the bottom housing.

In further embodiments, the assembly and/or system includes: a detachable second housing set (e.g., including a second top housing including one or more access ports, where at least one access port is configured to be in fluidic communication with the cell culture membrane; and a second bottom housing, where the second top housing and the second bottom housing are configured to accommodate the transferrable insert and to be reversibly attached, thereby facilitating transfer of the transferrable insert). In some embodiments, the second housing set is configured as a culture module. In other embodiments, the top sealing layer includes a channel configured to be in fluidic communication with the cell culture membrane, and at least one access port of the second top housing is configured to be in fluidic communication with the channel of the top sealing layer.

In a third aspect, the invention features a transferrable cell culture insert including: a handling layer; an aperture disposed within the handling layer; and a cell culture membrane disposed within or in proximity to the aperture (e.g., where the cell culture membrane includes a self-assembled membrane including a plurality of nanofibers). In some embodiments, a periphery of the aperture includes a porous scaffold and/or the self-assembled membrane is tethered to a surface of the porous scaffold.

In some embodiments, the periphery includes a rim having a first height and the self-assembled membrane has a second height (e.g., where the first height is greater than the second height). In other embodiments, the self-assembled membrane includes an interleaving portion tethered to the handling layer, or a portion thereof, and a freestanding portion suspended within the aperture.

In a fourth aspect, the present invention features a stacked cell culture assembly comprising a plurality of transferrable cell culture inserts (e.g., any described herein).

In a fifth aspect, the present invention features a method of forming a transferrable cell culture insert. In some embodiments, the method includes: placing an aperture of a handling layer in contact with one or more precursor agents (e.g., where the one or more precursor agents are configured to react and form a self-assembled membrane and where a periphery of the aperture further comprises a porous material); and forming the self-assembled membrane disposed within the aperture and/or in proximity to the aperture (e.g., where one or more fibers of the self-assembled membrane are interleaved to the porous material surrounding the periphery of the aperture, or a portion of the periphery).

In some embodiments, the method includes (e.g., after the forming step): removing the handling layer and the self-assembled membrane from the one or more precursor agents, thereby providing the transferrable insert; and/or rinsing the transferrable insert with one or more agents.

In some embodiments, the method (e.g., the placing step) includes placing the aperture in contact with a first precursor agent on a first surface of the handling layer and with a second precursor agent on a second surface of the handling layer (e.g., thereby forming an interface of the first and second precursor agents within the aperture). In other embodiments, the method (e.g., the placing step) includes assembling a first platen (e.g., including the first precursor agent), placing the aperture above the first platen (e.g., and in contact with the first precursor agent), and assembling a second platen (e.g., including the second precursor agent), where the second platen is placed above the aperture and the aperture is in contact with the second precursor agent.

In some embodiments, the first precursor agent includes a peptide amphiphile and/or the second precursor agent includes a biopolymer or a monomer thereof.

In some embodiments, the method (e.g., the forming step) includes establishing an interface between the first precursor agent and the second precursor agent and forming the self-assembled membrane at the interface.

In as sixth aspect, the present invention features a method (e.g., for forming a cell culture) including assembling a seeding module; seeding one or more cells within the seeding module (e.g., any described herein, including any portions on the seeding module described herein, such as on the cell culture membrane of the transferrable insert); transferring a portion of the seeding module (e.g., the transferrable cell culture insert) to a culture module (e.g., any described herein); incubating the one or more cells within the culture module; removing a portion of the culture module (e.g., the transferrable cell culture insert); and releasing one or more cells (e.g., from the transferrable cell culture insert).

In some embodiments, the seeding module (e.g., any described herein) includes a transferrable cell culture insert disposed between within a detachable first housing set (e.g., including a first top housing and a first bottom housing). In some embodiments, the transferrable insert includes a handling layer, an aperture disposed within the handling layer, and/or a cell culture membrane disposed or in proximity to within the aperture. In other embodiments, the seeding module includes a top housing further including a top loading reservoir (e.g., configured to deliver the one or more cells to the transferrable insert); and a bottom housing further including a channel (e.g., configured to deliver one or more reagents to the one or more cells disposed on the cell culture membrane).

In some embodiments, the culture module includes a transferrable cell culture insert disposed between within a detachable second housing set (e.g., including a second top housing and a second bottom housing). In other embodiments, the culture module includes a top sealing layer including a channel (e.g., configured to be in fluidic communication with the cell culture membrane, where the top sealing layer is further configured to be affixed to a top planar surface of the transferrable insert); a bottom sealing layer including a channel configured to be in fluidic communication with the cell culture membrane (e.g., where the bottom sealing layer is further configured to be affixed to a bottom planar surface of the transferrable insert); and a second bottom housing (e.g., further including a recess configured to accommodate the transferrable insert, the top sealing layer, and/or the bottom sealing layer).

In further embodiments, the method includes (e.g., before, during, and/or after the incubating step): analyzing the one or more cells on the cell culture membrane. In some embodiments, the method (e.g., the analyzing step) includes one or more of conducting an assay with the one or more cells (e.g., on the cell culture membrane); collecting one or more analytes released from the one or more cells; imaging the one or more cells; treating the one or more cells with one or more capture agents and/or detection agents; and/or exposing the one or more cells to one or more reactive agents.

In further embodiments, the method includes (e.g., before or after the incubating step): attaching a perfusion module (e.g., any described herein) to the culture module. In some embodiments, the perfusion module includes a top reservoir layer including a first reservoir; an isolation layer including a first via configured to be in fluidic communication with the first reservoir; a resistance layer including at least two vias and a channel disposed between the at least two vias (e.g., where one of the at least two vias is configured to be in fluidic communication with the first via of the isolation layer); and a bottom reservoir layer including a second reservoir and a second via (e.g., where the second via is configured to be in fluidic communication with at least one access port of the culture module).

In further embodiments, the method includes (e.g., after the transferring and/or incubating step): collecting one or more analytes eluted from the transferrable insert. In other further embodiments, the method includes (e.g., after the releasing step): analyzing the one or more cells, or components thereof. Additional details follow.

Definitions

As used herein, the term "about" means+/−10% of any recited value. As used herein, this term modifies any recited value, range of values, or endpoints of one or more ranges.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

By "micro" is meant having at least one dimension that is less than 1 mm. For instance, a microfluidic structure (e.g., any structure described herein) can have a length, width, height, cross-sectional dimension, circumference, radius (e.g., external or internal radius), or diameter that is less than 1 mm.

By "nano" is meant having at least one dimension that is less than 1 μm. For instance, a nanofluidic structure (e.g., any structure described herein) can have a length, width, height, cross-sectional dimension, circumference, radius (e.g., external or internal radius), or diameter that is less than 1 μm.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

FIG. 10A-10C provides an exemplary culture module for an exemplary scalable, easy-access, modular (SEAM) assembly. Shown are a schematic representation of SEAM architecture composed of PMMA housing with embedded magnets, PDMS channels, and a transferrable cell culture insert (FIG. 10A); an image of the transferrable cell culture insert with a membrane, where the dashed line outlines the micro-porous cell culture region and the scale bar is 1 mm (FIG. 10B); and an image of the assembled SEAM device with top and bottom microfluidic channels being distinct fluidic compartments with a U.S. quarter shown for scale (FIG. 10C).

FIG. 11A-11B shows one non-limiting embodiment. Shown are images of the top and bottom housing layers of the direct seeding module, in which the membrane is positioned on the bottom layer and the magnets compress and seal the culture insert between the lower perfusion channel and top housing layer (FIG. 11A);

and an image of an assembled seeding module, where the dashed line outlines the seeding chamber (FIG. 11B). After seeding a desired number of cells on the culture region of the insert, the platform is incubated to allow cell attachment. The seeded membrane is then decoupled and transferred to the culture module. FIG. 11C-11E shows another non-limiting embodiment. Shown are a schematic (FIG. 11C, left) and an image (FIG. C, right) of an assembled seeding module composed of top and bottom PMMA housing layers and a magnetically sealed culture insert. FIG. 11D provides an exemplary workflow (steps 1-4) to establish co-cultured tissue interfaces. The desired cell number was added to the culture region of the insert and allowed to attach (step 1). The insert was then decoupled from the PMMA housings (step 2), flipped over (step 3), resealed, and then seeded with a second population (step 4). FIG. 11E provides a representative image of co-cultured primary human alveolar epithelium stained for occludin and primary human microvascular endothelium stained for VE-cadherin both with nuclear counterstain. Scale bars are 40 µm.

In FIG. 12B, the arrow identifies the fluidic pathway from aa to bb through the culture channels, in which flow is driven by gravity and controlled by the height differential ($\Delta z$, e.g., where $\Delta z=z_1+z_2+z_3$) between the aa and bb fluid reservoirs. The fluidic circuit (inlet reservoir aa through the culture module to the outlet reservoir bb) was gently primed with medium using a syringe. In FIG. 12C, once filled, surface tension kept the medium from spilling out of the reservoirs, and the difference in hydrostatic pressure $\Delta P$ induced fluid flow from inlet to outlet reservoirs.

In FIG. 13A, shown is a workflow in which a) cells are seeded directly on the culture region of the membrane at the desired density using the seeding module. Then, b) a culture insert with attached cells is transferred to the culture platform for long-term perfusion culture and exposure studies. Cells can be b) directly imaged within the module, or c) the membrane can be removed for off-chip nucleic acid (e.g., RNA) extraction. The transfer of the culture insert (and attached cells) to off-chip extraction techniques limits sample losses and enables RNA analysis of microscale tissue culture. The modular approach enables d) a combination of functional and transcriptomic responses to be explored. FIG. 13B shows another exemplar workflow, in which a) cells are seeded and then b) the culture insert with attached cells is transferred to the culture platform for long-term perfusion culture and exposure studies. The insert can then be c) mounted on a slide for imaging or d) directly transferred for off-chip lysis and nucleic acid isolation. Cells can also be imaged within the platform using a long working distance objective. The modular approach enables a combination of imaging and gene level responses to be easily explored.

DETAILED DESCRIPTION OF THE INVENTION

The present invention relates to transferrable cell culture inserts, modular assemblies, and modular systems configured to support cell attachment and growth, as well as to facilitate acquisition of functional, structural, and transcriptomic information from such cells. In particular embodiments, these assemblies and its components provide a controlled cellular environment, in which chemical or biological cues can be delivered to on-chip cell cultures in a controlled manner and in which micron-scale structural features attempt to replicate in vivo structural and diffusive length scales. Furthermore, these assemblies are adapted for modular use, in which different modalities or biochemical techniques are provided by different housing modules that are adapted to accommodate an insert including the cell culture. In this way, the same cell culture can be easily transferred for further assays, either conducted on-chip or off-chip. Additional details follow.

Modular Assemblies

The present invention relates to modular assemblies having a housing set that accommodates a transferrable cell culture insert. The housing set includes one or more access ports configured to deliver one or more agents to cells, and the transferrable insert include a cell culture membrane configured to attach and support cells, populations of cells, tissue, etc., as well as 3D assemblages thereof. In some embodiments, the insert includes a cell culture membrane that is a thin suspended membrane disposed within an aperture of a handling layer. For facile removal of the insert, the housing set can include one or more fasteners configured to be reversibly attached to each other. In this way, the housing set can be easily disassembled to access the cell culture supported on the insert. In further embodiments, one or more sealing layers can be included to retain cells and agents within the housing set, the insert, and optional fluidics layers.

Figure 1A:
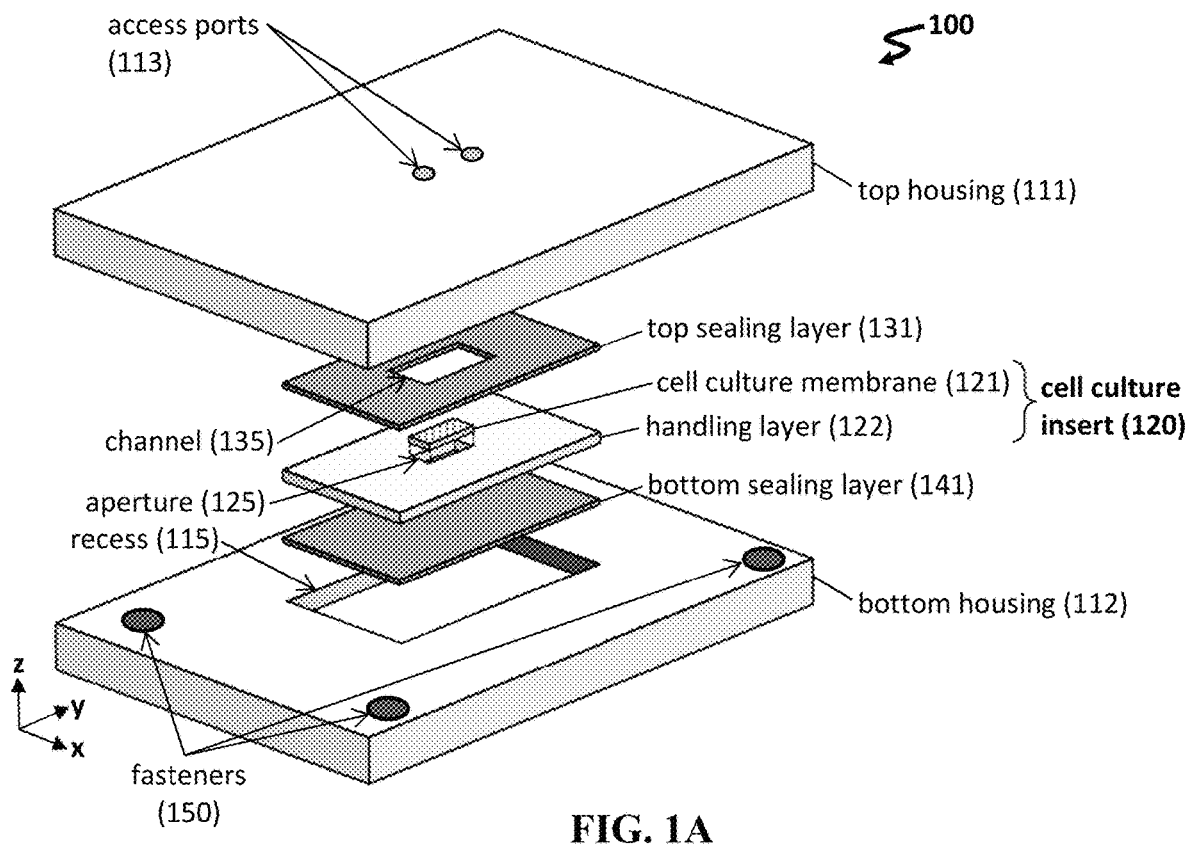
FIG. 1A-1E provides an exemplary modular assembly and its components. Shown are an exploded view of an exemplary modular assembly 100 including a cell culture insert 120 (FIG. 1A); a perspective view of an assembled modular assembly 1000 (FIG. 1B); a cross-sectional view along line 1C-1C in FIG. 1B (FIG. 1C); a cross-sectional view along line 1D-1D in FIG. 1B (FIG. 1D); and an exploded view of another exemplary modular assembly 1100 having one or more adhesive sealing layers 1161,1162, 1163,1164 (FIG. 1E).
Figure 1B:
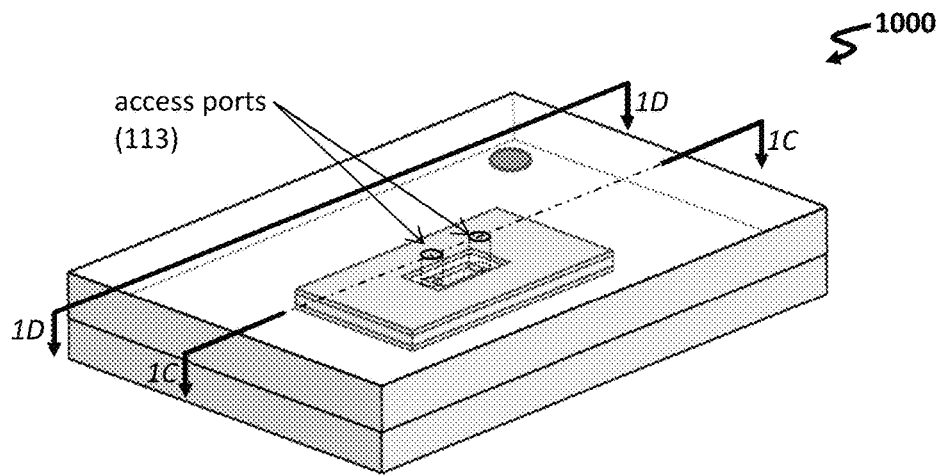

FIG. 1A-1B shows an exemplary modular assembly 100, 1000. As can be seen, the assembly 100 includes a housing set, which in turn includes a top housing 111 and a bottom housing 112. Each component of the assembly can be configured to allow for an aligned construct 1000 once assembled.

Each housing portion can include one or more vias, channels, chambers, alignment features, or recesses to control fluidic resistance and/or to accommodate any useful component for use within the modular assembly. For instance, the top housing 111 can include one or more access ports 113 to deliver agents to cells within the assembly. In another instance, the bottom housing 112 can optionally include a recess 115 configured to accommodate the cell culture insert 120 or one or more sealing layers 131,141. In yet another instance, the top and/or bottom housing can include one or more alignment features (e.g., alignment holes within the top and bottom housing, as well as the disposed culture insert) to properly stack and align the components within the assembly.

The cell culture insert generally includes a cell culture membrane to support cells and a handling layer to facilitate transfer and manipulation of the insert. The cell culture membrane can include any useful substrate or scaffold (e.g., any described herein). In addition, the handling layer can include any useful material (e.g., any described herein, including porous and/or non-porous substrates). In one instance, the cell culture insert 120 includes a handling layer 122, an aperture 125 disposed within or in proximity to the handling layer, and a cell culture membrane 121 disposed within the aperture. The cell culture membrane, in turn, can include a tethered portion configured to be attached to a periphery of the aperture and a freestanding portion suspended within the aperture.

The assembly can include one or more sealing layers disposed between different components. For instance, if the housing set and cell culture membrane include materials that are non-conformal (e.g., a rigid polymer), then gaps or voids may be present between these different components. To reduce fluid leakage and contamination, one or more sealing layers may be present between the housing and the cell culture insert to minimize such gaps or voids. As seen in FIG. 1A, the modular assembly can include a top sealing layer 131 configured to be affixed (e.g., reversibly affixed) to a top surface of the insert 120, as well as a bottom sealing layer 141 configured to be affixed (e.g., reversibly affixed) to a bottom surface of the insert 120. In this way, cells and agents delivered to the insert will be maintained within any chamber or channel in fluidic communication with the cell culture membrane of the insert. Optionally, the sealing layer can include one or more fluidic elements, such as vias, channels, or chambers to provide fluidic communication between two or more components. For instance, the top sealing layer 131 can include a chamber 135 that provides fluidic communication between the access ports 113 and the cell culture membrane 121.

Figure 1C:
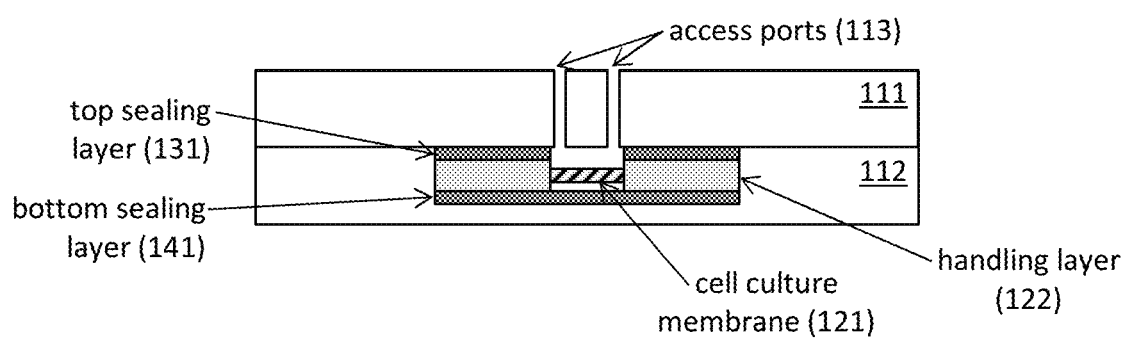

Fluidic pressure may be applied in any useful manner to provide any useful fluidic path. For instance, as seen in FIG. 1C, one or more agents can be pumped through one of the access ports 113 of the top housing 111 and into the channel of the top sealing layer 131 that overlays the cell culture membrane 121, and any excess agents can be collected at the other access port 113. If the cell culture membrane is porous, then agents can also be delivered to a chamber formed in the space disposed within the bottom housing 112 and located between the cell culture membrane 121 and the bottom sealing layer 141.

Each of the housing can include one or more fasteners 150 (e.g., any described herein), which are located in any useful position (e.g., to ensure a seal between the top and bottom housing, as well as between any component(s) disposed within the housing). In one instance, each pair of fasteners includes a pair of magnetic fasteners, in which a first magnet is aligned within the top housing to reversibly bind to the second magnet disposed within the bottom housing when the top and bottom housing are in proximity to each other. In another instance, each pair of fasteners includes a magnet and a metal (e.g., a ferromagnetic metal), in which the metal is located within the top housing and the magnet is located within the bottom housing or vice versa. The metal and magnet can be aligned to allow for reversible binding upon bringing the top and bottom housing in proximity to each other. Other fasteners (e.g., any described herein) can be employed in a similar manner. Alternatively, one or more external fasteners can be used to clamp the top housing to the bottom housing.

Figure 1D:
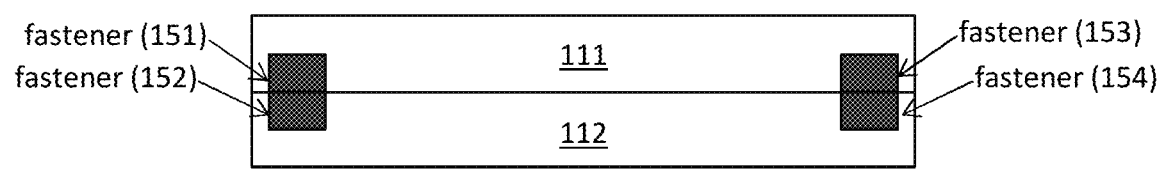

As seen in FIG. 1D, the fasteners are magnets that are aligned to allow for reversible binding upon bringing the top and bottom housing in proximity to each other. A first pair of magnets 151,152 is located within the top housing 111 and bottom housing 112, respectively, and aligned to allow for binding by way of magnetic attraction. A second pair of magnets 153,154 is also located within the top housing 111 and bottom housing 112, respectively. Additional pairs of magnets can be placed within the housing (e.g., along each corner and/or edge of the housing) to facilitate a seal between each of the components of the modular assembly. In addition, each of the magnets 151,152 and 153,154 is arranged to ensure appropriate alignment of magnetic poles. The magnets can be of any useful shape (e.g., bar, cylindrical, etc.), cross-section (e.g., circular, rectangular, etc.), dimension, material (e.g., a rare earth material), or form (e.g., solid, powder, bead, etc., including any described herein). For instance, the magnet fasteners can extend through the entire height of the housing (i.e., a height along the z-axis in FIG. 1A) or through only a portion of the height of the housing (e.g., as in FIG. 1D).

Alternatively, the assembly employs adhesive as a fastener. The adhesive can be provided as an adhesive sealing layer or, alternatively, as a coating on a sealing layer. To ensure that each layer is aligned to provide the desired fluidic network, one or more layers (e.g., adhesive layers, sealing layers, handling layers, etc.) can optionally include one or more alignment features (e.g., an alignment hole that allows an alignment pin or post to be inserted within each hole in order to provide an aligned stack). An alignment pin or post can be provided externally or, alternatively, the post can be included on a surface of the top and/or bottom housing. Alignment features can be placed in any useful region of each layer, such as away from the fluidic elements. After alignment, the stack can be treated to activate the adhesive. If the adhesive is pressure-sensitive, then pressure can be applied to the stack to promote adhesion of the layers. Alternatively, if the adhesive is heat- or light-activated, then heat or light can be applied to the stack.

Figure 1E:
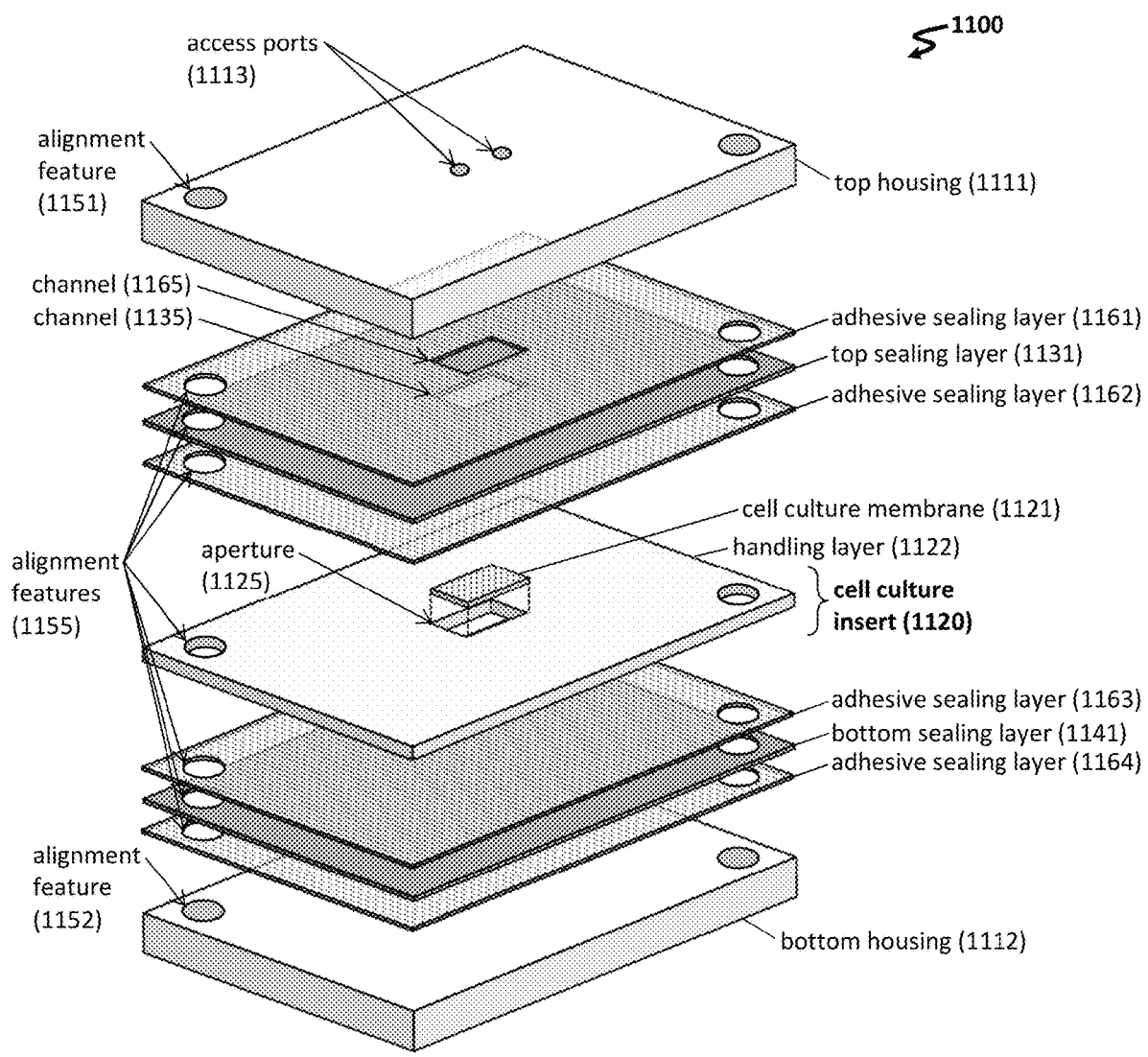

As seen in FIG. 1E, the assembly 1100 includes a top housing 1111 including first alignment features 1151 (e.g., alignment holes) and access ports 1113, as well as a bottom housing 1112 including second alignment features 1152 (e.g., alignment holes) configured to be aligned with the first alignment features 1151. The top and bottom housing are configured to accommodate the cell culture insert 1120, which in turn includes a cell culture membrane 1121 disposed within an aperture 1125 of the handling layer 1122 and further includes alignment features 1155 disposed within the handling layer 1122.

Alignment features can be included in any useful component, such as any other component (e.g., sealing layer and/or handling layer) configured to be disposed between the top and bottom housing. For instance, the top sealing layer 1131 includes a channel 1135 and alignment features 1155, and this top sealing layer 1131 can optionally include an adhesive material disposed on its top and/or bottom surface. The bottom sealing layer 1141 also includes alignment features 1152.

Furthermore, the top sealing layer 1131 and bottom sealing layer 1141 can be associated with one or more adhesive sealing layers, in which each adhesive sealing layer is configured to be affixed to a surface of the top or bottom sealing layer. As can be seen, a first adhesive sealing layer 1161 is configured to be affixed to a top surface of the top sealing layer 1131, and a second adhesive sealing layer 1162 is configured to be affixed to a bottom surface of the top sealing layer 1131. As can be seen, a first adhesive sealing layer 1161 is configured to be affixed to a top surface of the top sealing layer 1131, and a second adhesive sealing layer 1162 is configured to be affixed to a bottom surface of the top sealing layer 1131. A third adhesive sealing layer 1163 is configured to be affixed to a top surface of the bottom sealing layer 1141, and a fourth adhesive sealing layer 1164 is configured to be affixed to a bottom surface of the bottom sealing layer 1141. The adhesive sealing layer can include any useful fluidic element, e.g., a channel 1165, that can optionally be aligned with any other fluidic element, e.g., an aperture 1125 of the cell culture insert 1120.

Figure 2A:
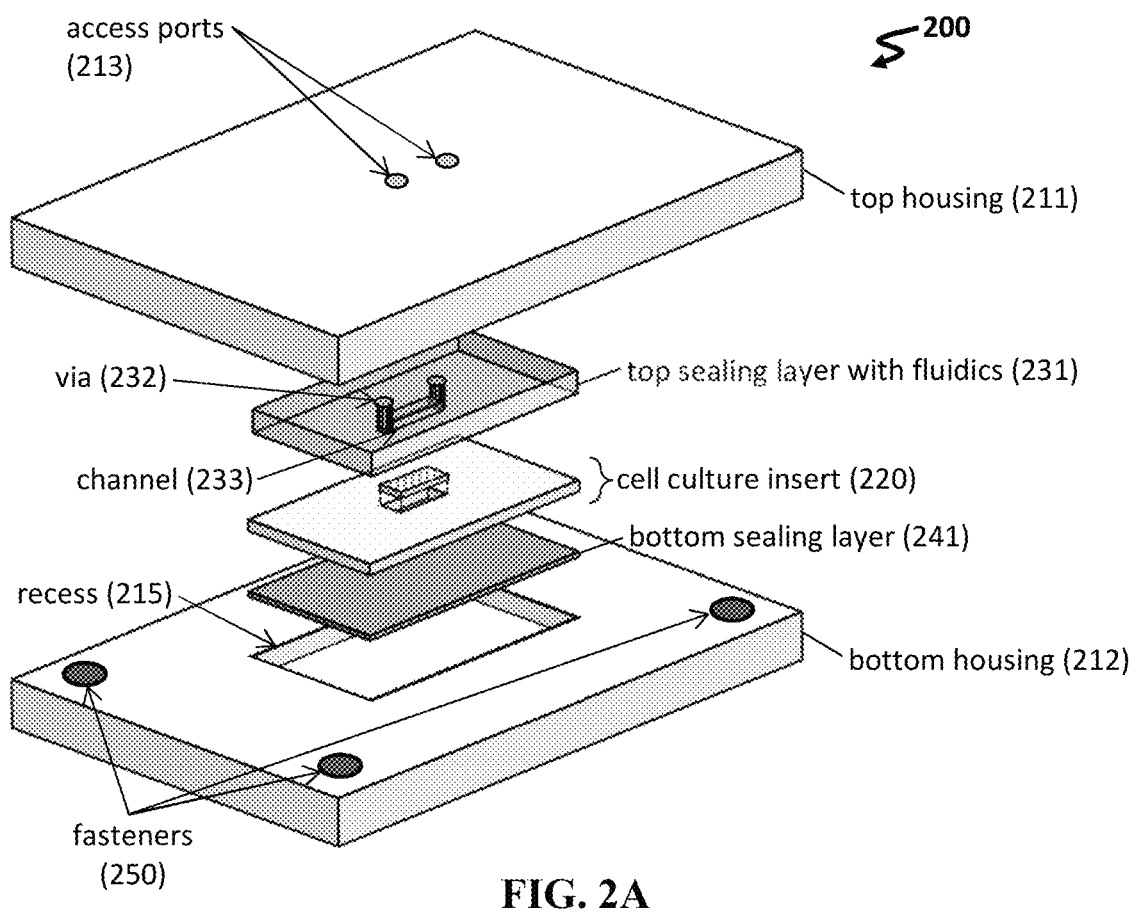
FIG. 2A-2B provides other exemplary modular assemblies. Shown are an exploded view of an exemplary modular assembly 200 including a cell culture insert 220 (FIG. 2A) and an exploded view of another exemplary modular assembly 2000 including a fluidics layer 2060 for use with a cell culture insert 2020 (FIG. 2B).

The modular assembly can include any other useful component to provide a fluidic network. In one instance, as seen in FIG. 2A, the modular assembly 200 includes a top sealing layer 231 including fluidic elements (e.g., one or more fluidic channels, vias, channels, chambers, valves, etc.) that affixes to the cell culture insert 220. The top sealing layer 231 includes one or more vias 232 to provide fluidic communication with the access ports 213 in the top housing 211, as well as a channel 233 to provide fluidic communication with the cell culture membrane of the cell culture insert 220. The bottom housing 212 includes a recess 215 to accommodate the bottom sealing layer 241 with the cell culture insert 220, as well as one or more fasteners 250. Optionally, the bottom sealing layer and/or bottom housing can also include one or more fluidic elements (e.g., one or more fluidic channels, vias, channels, chambers, access ports, valves, etc.) in order to, e.g., provide both apical and basolateral access to the cell culture disposed on the cell culture membrane.

Figure 2B:
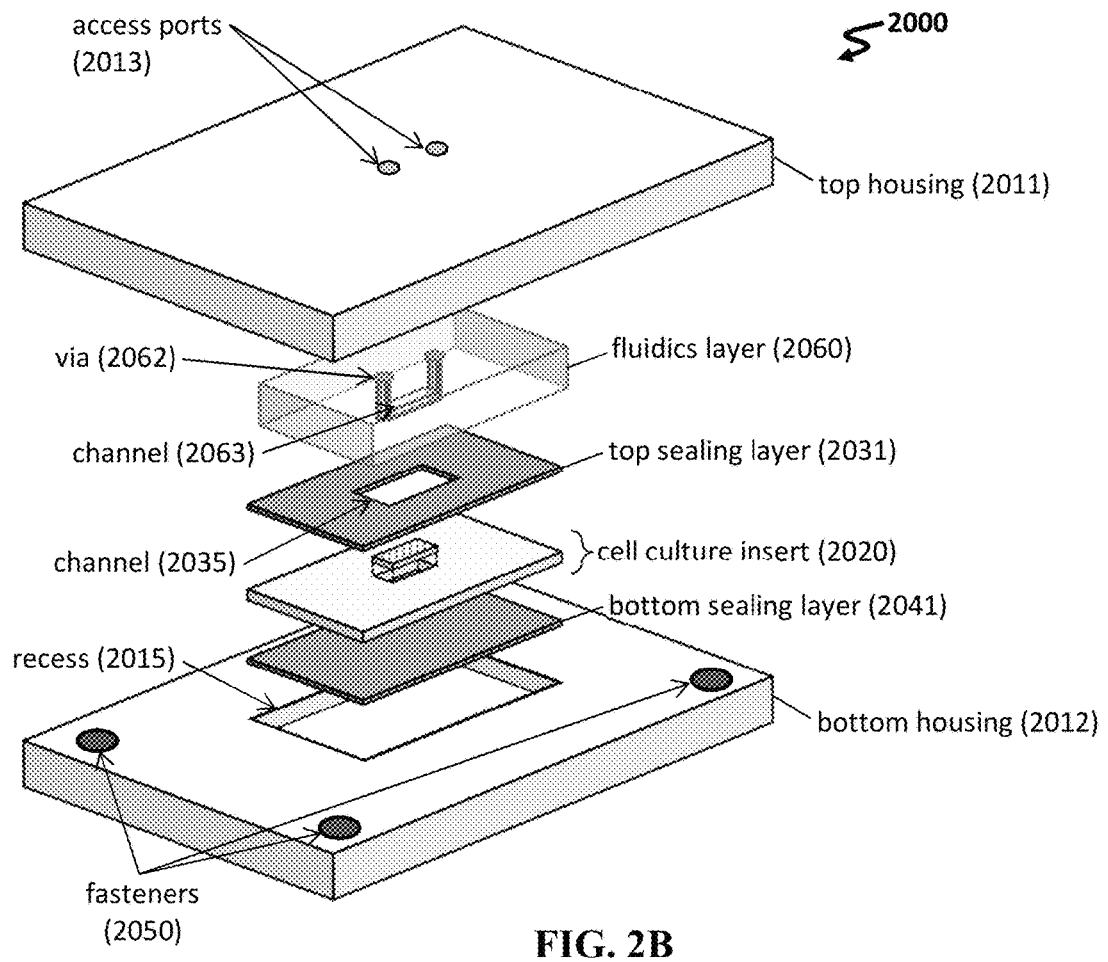

In yet another instance, fluidics may be introduced in a different layer, e.g., a fluidics layer. As seen in FIG. 2B, the modular assembly 2000 can include a fluidics layer 2060 having one or more channel 2063, as well as one or more vias 2062 in fluidic communication with the access port 2013 of the top housing 2011. The fluidics layer 2060 can be configured to be affixed to the top sealing layer 2031, in which the fluidics within the fluidics layer 2060 is aligned with the channel 2035 in the top sealing layer 2031 in order to provide a fluidic network with access to the cell culture disposed on the cell culture insert 2020. Each of the top housing 2011 and/or bottom housing 2012 can include any useful component, including one or more fasteners 2050, access ports 2013, and/or recesses 2015. Any recess herein can be configured to accommodate any useful aligned stack, such as an aligned stack including one or more of the following components: a cell culture insert, one or more sealing layers, one or more fluidics layers, or any other useful layer. Additional modular assemblies, and its components, are described herein.

Transferrable Inserts

The assemblies and systems described herein include a transferrable insert, which in turn includes a cell culture membrane and a handling layer. The cell culture membrane (e.g., a microscale porous cell culture region) is surrounded by the handling layer (e.g., including a non-porous carrier region), thereby facilitating transfer and coupling with different fluidic modules (e.g., a seeding module, a cell culture module, a perfusion module, etc.).

In one instance, the transferrable insert is configured to be removable from the module assemblies described herein. This is in contrast to conventional platform techniques, which permanently seal membranes between elastomeric channels by primarily using oxygen plasma bonding (see, e.g., Ismagilov R F et al., "Microfluidic arrays of fluid-fluid diffusional contacts as detection elements and combinatorial tools," *Anal. Chem.* 2001; 73(21):5207-13). Such conventional platforms can have difficulties forming robust, liquid-tight seals when hydrated materials are present. By using both the reversible attachment scheme (e.g., magnetic latching) and removable culture insert structures, the culture materials do not have to be directly compatible with the overall fabrication method of the architecture. Thus, manufacturing methods can be separated into discrete steps, in which a first step can be optimized with fabrication conditions to generate the insert with a delicate porous membrane and a second step can be optimized to manufacture housing sets with useful fluidic elements.

Figure 3A:
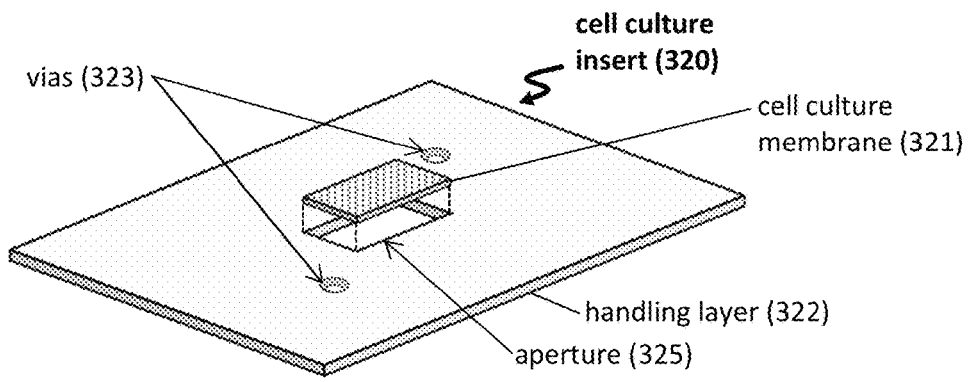
FIG. 3A-3F provides exemplary transferrable cell culture inserts. Shown are an exemplary insert 320 including optional vias 323 (FIG. 3A); another exemplary insert 3020 composed of laminated top and bottom handling layers 3022,3023 (FIG. 3B); (C) an exemplary insert 3120 assembled to include a cell culture membrane 3121 disposed within an aperture 3125 (FIG. 3C); and yet another exemplary insert 3220 (FIG. 3D), including a cell culture membrane 3221 supported by a rim 3224 of the handling layer 3223. Also shown are handling layers including a rim layer 3324 with a single handling layer 3322 (FIG. 3E) and a rim layer 3424 disposed between two handling layers 3422,3423 (FIG. 3F).

FIG. 3A shows an exemplary cell culture insert 320 including a handling layer 322 and an aperture 325 disposed within the handling layer. The handling layer facilitates manipulation of the cell culture membrane, which itself can be fragile and can include cell cultures requiring gentle handling. Thus, in one instance, the handling layer is sized to allow for manual manipulation (e.g., by use of forceps, tweezers, etc.) and/or integration into a modular assembly. The handling layer can be formed from any useful material, e.g., a rigid material to maintain the planarity of the membrane, a biocompatible material to minimize contamination or leached contaminants to the cell culture, a porous material to support tethering of a cell culture membrane (e.g., where a portion of the handling layer in proximity to the aperture includes the porous material), and/or a non-porous material to limit leakage between different components of the modular assembly (e.g., where a portion of the handling layer in proximity to the outer edge includes a non-porous material, in which the outer edge regions of the handling layer will be contacted to transfer the culture insert). Optionally, the handling layer can include one or more fluidic elements (e.g., channels, vias, valves, or any other element described herein) to provide a useful fluidic network. As seen in FIG. 3A, the handling layer 322 can include one or more vias 323 that are aligned with one or more fluidic elements disposed in a sealing layer, a fluidic layer, and/or a housing adapted to be accommodate the handling layer of the cell culture insert.

The cell culture insert includes one or more cell culture membranes. In use, the cell culture membrane provides a substrate to support cell attachment and/or growth. The physical properties of the membrane can be tuned to provide a useful substrate, where such physical properties include stress, strain, elastic modulus, pore size, surface chemistry, membrane thickness, etc. In particular embodiments, the cell culture membrane is suspended within the aperture of the handling layer, thereby ensuring that deposited cells encounter only the cell culture membrane. In this way, growth conditions can be spatially controlled by controlling the characteristics of the cell culture membrane. Furthermore, each component of the cell culture insert can be selected to allow for sterilization, e.g., by gamma irradiation.

As seen in FIG. 3A, the cell culture membrane 321 is configured to be disposed within or in proximity to the aperture 325 of the handling layer 322. The cell culture membrane can be formed and placed within the aperture in any useful manner. The membrane can be formed in situ (e.g., by way of self-assembly or any other useful deposition process), excised from a larger membrane source, or deposited on a support already in place within an aperture of the handling layer. The membrane can be placed in any useful manner, such as within the aperture or in proximity to the aperture (e.g., suspended from a periphery of the aperture).

In one instance, the membrane can be cut from a larger membrane sample and sized to be placed within the aperture. If needed, one or more adhesives (e.g., pressure sensitive adhesives) can be placed on the periphery of the aperture to ensure a seal between the membrane and the handling layer. Furthermore, the membrane can be further functionalized (e.g., in any manner described herein).

In another instance, the membrane is a self-assembled membrane including a suspended portion and a tethered portion. The suspended portion can be a freestanding portion of the membrane that provides a surface within the aperture, and the tethered portion can be a portion of the membrane having polymers (e.g., fibers) that interleave with the material located at the periphery of the aperture. By having such interleaving polymers, the membrane is fixed to the handling layer and suspended within the aperture. To facilitate such interleaving, the periphery of the aperture can include a porous scaffold (e.g., any useful material having a pore size of from about 0.1 µm to about 100 µm). Optionally, such architecture can provide a self-assembled, suspended membrane that is thinner than the thickness of the periphery of the aperture (e.g., thinner than the surrounding porous scaffold).

In yet another instance, the membrane includes a support and a self-assembled membrane deposited upon that support. The support can include a porous material of any useful pore size (e.g., a first pore size that is larger than the desired pore size of the final cell culture material), such as a polyester or polycarbonate porous membrane that is located within the aperture. Then, a self-assembly reaction (e.g., a reaction between a peptide amphiphile and a biopolymer, such as hyaluronic acid, or monomers of the biopolymer) can be conducted to deposit self-assembled micelles or fibers within the pores of the support. The self-assembly reaction can be characterized by a second pore size or a second permeability (e.g., determined by molecular weight cut-off studies) that is different than the first pore size of the support.

One or more cell culture membranes can be stacked (e.g., along the z-direction in FIG. 1A) to provide a multilevel structure to grow different cell populations upon each cell culture membrane. Such stacks can be formed in any useful manner, e.g., by stacking cell culture membranes within the same aperture of a handling layer and optionally including spacers between each cell culture membrane; or by stacking a plurality of cell culture inserts, in which each insert includes a cell culture membrane that is configured to align with other cell culture membranes within the stack.

Figure 3B:
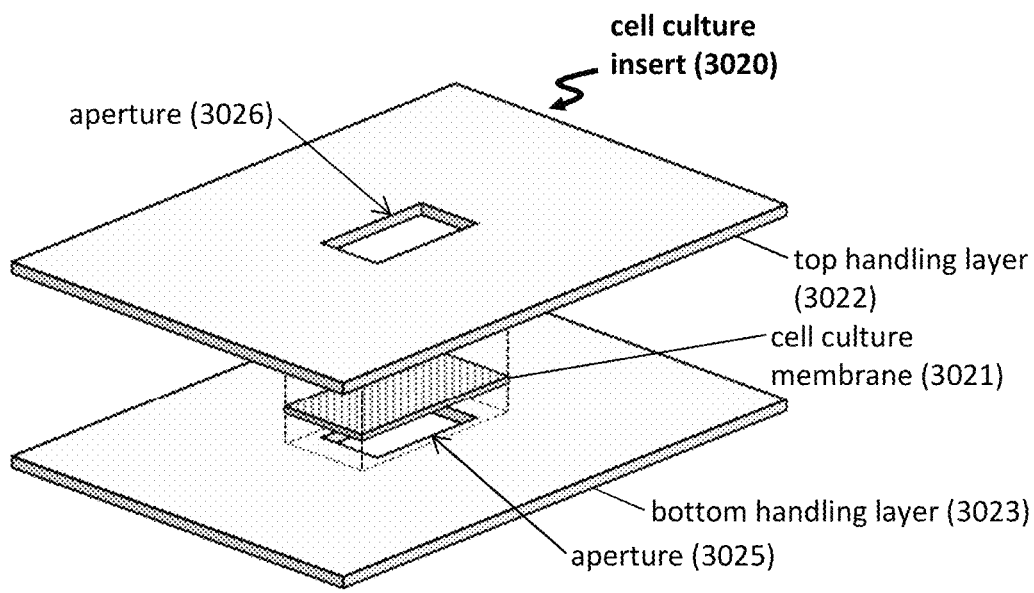

In some instances, the insert is formed by laminating various layers. For example, as seen in FIG. 3B, a top handling layer 3022 and bottom handling layer 3023 can include a polymer (e.g., polyester) sheet having desired laser cut vias and/or apertures 3026,3025. The cell culture membrane 3021 can be aligned to be disposed between the apertures 3026,3025, and then the stack can be pressed together to form a laminate insert structure 3020. To maintain that laminate structure, each of the handling layers can optionally include a pressure sensitive adhesive on one face or surface, in which a cell culture membrane can be aligned between two adhesive surfaces and then the stack can be pressed together to form the laminate structure. Alternatively, the handling layer can include a meltable material (e.g., a polymer, such as any described herein) that can be hot-pressed together to form a laminate structure. Such a laminate structure can be compatible with using commercially available microporous and nanoporous membranes that have been optimized to provide low auto-fluorescence, high optical clarity, and defined pore size distributions.

Figure 3C:
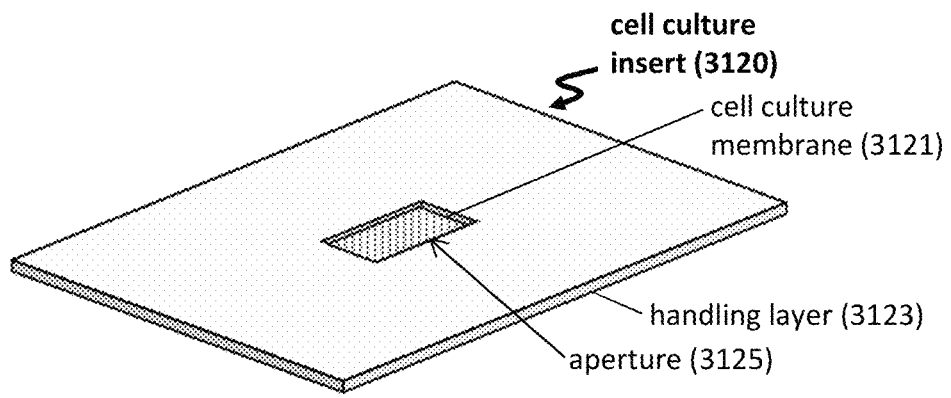

In other instances, as in FIG. 3C, the insert 3120 includes a freestanding membrane 3121 disposed within the aperture 3125 of the handling layer 3123. For example, the freestanding membrane can be a suspended membrane. When the cell culture membrane is a suspended membrane (i.e., a membrane suspended within an aperture), then the periphery of the aperture may be modified in any useful manner to tether the suspended membrane within the handling layer. For instance, the periphery of the aperture can include an adhesive. In another instance, the periphery of the aperture can include a porous substrate that facilitates interleaving of the suspended membrane to the handling layer.

In one non-limiting embodiment, the suspended membrane is formed in situ by using two or more precursor agents. Optionally, the periphery of the aperture can be impregnated with a first precursor agent and then exposed to the second precursor agent that reacts with the first precursor agent, thereby facilitating polymerization within the periphery region of the aperture. In yet another option, the periphery of the aperture can include a porous scaffold having a top surface and a bottom surface, in which the top surface is exposed to a first precursor agent and the bottom surface is exposed to a second precursor agent. In this way, the self-assembled membrane is tethered to the handling layer by an interleaving portion disposed within the porous scaffold, and the self-assembled membrane further includes a freestanding portion suspended within an aperture of the handling layer.

The periphery of the aperture can have any useful geometry. For instance, the aperture can have any useful dimension, including geometry (e.g., rectangular, square, circular, ellipsoid, etc.), length, and width. In addition, the periphery of the aperture can include a rim that surrounds the aperture. The rim can provide a stepped region that can assist in disposing the cell membrane within or in proximity to the aperture. For instance, the rim can be treated with an adhesive that facilitates affixing the membrane to the handling layer. Alternatively, the rim can include a porous scaffold that facilitates tethering the membrane.

Figure 3D:
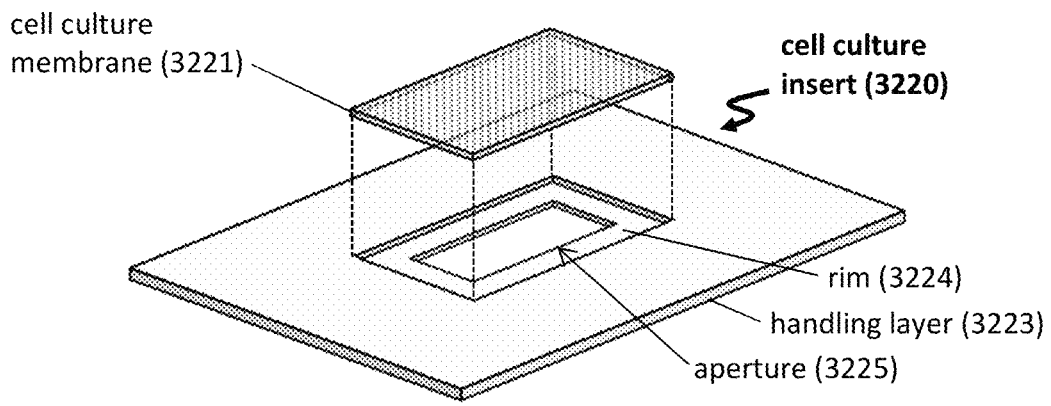
Figure 3E:
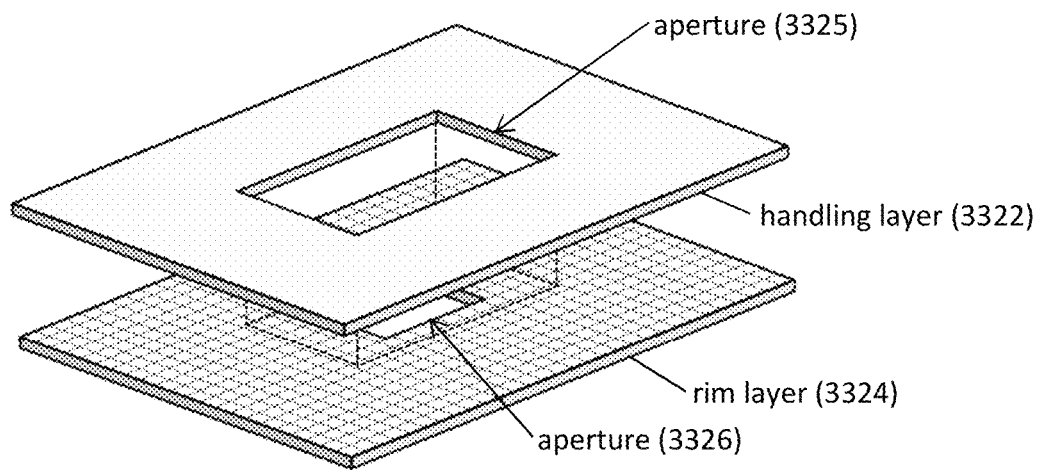

FIG. 3D provides an exemplary insert 3220 including a handling layer 3223, an aperture 3225 disposed within the layer, and a rim 3224 surrounding the periphery of the aperture. The cell culture membrane 3221 is configured to be placed within the cavity formed by the rim 3224, thereby providing a membrane in proximity to (e.g., overlying) the aperture 3225. The rim region can be formed in any useful manner, such as by machining the handling layer to include the rim, by laminating two or more different layers, etc. FIG. 3E shows an exemplary laminate insert structure including a rim layer 3324 having an aperture 3326 disposed therein and a single handling layer 3322 having an aperture 3325 disposed therein, where the two apertures are configured to be aligned and to provide an exposed rim once the structure is laminated. The edges of the rim layer can extend to the edge of the handling layer or, alternatively, the rim layer can include an outer edge dimension that is less than that of the handling layer.

Figure 3F:
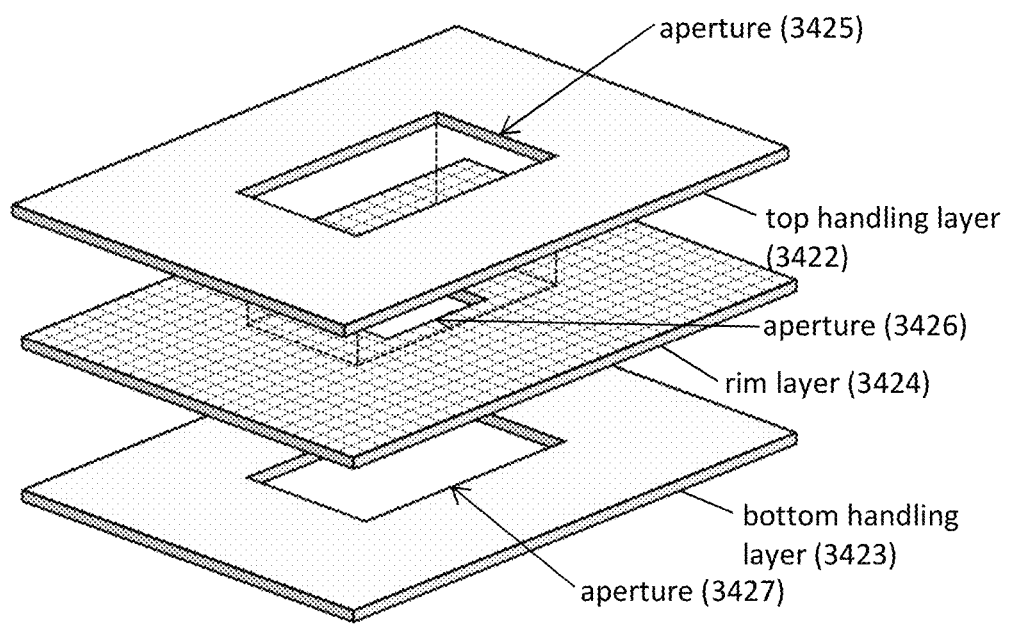

FIG. 3F shows another exemplary laminate insert structure including a rim layer 3424 disposed between two handling layers 3422,3423. Again, the aperture 3426 of the rim layer is configured to be aligned with the apertures 3425,3427 of the handling layers 3422,3423 to provide an exposed rim. The rim layer can be any useful material, e.g., a porous material. To minimize fluidic communication between the surfaces of the insert with any underlying or overlying fluidic chamber, the insert can include a top handling layer and a bottom handling layer that are each composed of a non-porous substrate.

The insert can include a culture region, which can include any useful cell culture membrane. The culture region, as well as the cell culture membrane, can have any useful dimension (e.g., length and/or width), e.g., of from about 1 mm to about 10 mm. The cell culture membrane can be formed of any useful substrate, such as a porous substrate (e.g., a porous polymer substrate), an ultrathin nano-membrane, a protein film (e.g., a collagen film), a gel (e.g., a hydrogel sheet), a patterned substrate, a biological scaffold (e.g., an extracellular matrix (ECM) substrate or film), and/or a layered composite biomaterial, or any other described herein.

In one non-limiting instance, the insert includes a suspended thin membrane configured to support one or more cells, cell populations, and/or tissue. Thus, in some instances, the membrane or a portion thereof (e.g., a portion configured as a tissue culture region) can include any useful biocompatible material, including porous forms thereof, such as a polyester (e.g., polyethylene terephthalate), a polycarbonate (e.g., a track etched polycarbonate), or a polystyrene having any useful pore size (e.g., a pore size of from about 0.1 µm to about 50 µm, such as from 0.1 µm to 25 µm, 0.1 µm to 10 µm, 0.1 µm to 5 µm, 0.1 µm to 1 µm, 0.25 µm to 25 µm, 0.25 µm to 10 µm, 0.25 µm to 5 µm, 0.25 µm to 1 µm, 0.5 µm to 25 µm, 0.5 µm to 10 µm, 0.5 µm to 5 µm, 0.5 µm to 1 µm, 1 µm to 25 µm, 1 µm to 10 µm, 1 µm to 5 µm, 5 µm to 25 µm, or 5 µm to 10 µm).

The membrane can have any useful other dimension, including thickness (e.g., a thickness of $z_m$ as in FIG. 20D or a dimension along the z-axis in FIG. 1A), width (e.g., a dimension along the x-axis in FIG. 1A), or length (e.g., a dimension along the y-axis in FIG. 1A). Exemplary thicknesses include of from about 1 µm to 1 mm (e.g., from 1 µm to 500 µm, 1 µm to 250 µm, 1 µm to 100 µm, 1 µm to 50 µm, 5 µm to 1 mm, 5 µm to 500 µm, 5 µm to 250 µm, 5 µm to 100 µm, 5 µm to 50 µm, 10 µm to 1 mm, 10 µm to 500 µm, 10 µm to 250 µm, 10 µm to 100 µm, 10 µm to 50 µm, 25 µm to 1 mm, from 25 µm to 500 µm, 25 µm to 250 µm, 25 µm to 100 µm, or 25 µm to 50 µm).

The membrane can be further functionalized, e.g., by way of depositing one or more polymers, proteins, peptides, or mixtures thereof, treating the surface with a plasma; sterilizing the membrane; etc., either before or after placing it in proximity to the aperture. For instance, the membrane can be treated with a protein, such as an extracellular matrix protein, e.g., collagen (e.g., type I or IV), fibronectin, laminin, polylysine (e.g., poly-D-lysine), polyornithine (e.g., poly-L-ornithine), gelatin, entactin, proteoglycan, a solubilized basement membrane matrix (e.g., Matrigel™), etc., as well as combinations thereof.

Any useful membrane can be used to grow, culture, or propagate cells on the transferrable insert. In particular an embodiment, the membrane is composed of a self-assembled peptide amphiphile optionally in the presence of an extracellular matrix (ECM) protein, a saccharide, or a carbohydrate, as well as a component thereof. The peptide amphiphile generally include a hydrophobic tail (e.g., an optionally substituted alkyl, alkenyl, alkynyl, or alkoxycarbonyl, i.e., R—C(O)—, where R is an optionally substituted $C_{12-24}$ alkyl group), a beta sheet forming peptide segment (e.g., a peptide segment comprising or consisting of -Val$_3$Ala$_3$-(SEQ ID NO:1) or -Ala$_4$Gly$_3$- (SEQ ID NO:2)), and a charged segment (e.g., -Lys or -Glu). Exemplary peptide amphiphiles are described in U.S. Pat. Nos. 8,772,228; 8,748,569; 8,580,923; 8,512,693; 8,450,271; 8,366,974; 8,138,140; 8,124,583; 8,114,835; 8,114,834; 8,110,125; 8,080,262; 8,063,014; 7,851,445; 7,838,491; 7,745,708; 7,683,025; 7,662,298; 7,554,021; 7,544,661; 7,534,761; 7,491,690; 7,452,679; 7,390,526; 7,371,887; and 7,371,719, each of which is incorporated herein by reference in its entirety. Other exemplary amphiphiles include any of the following: X-Val$_3$Ala$_3$Lys$_3$-Y (SEQ ID NO:4), X-Val$_3$Ala$_3$-Y (SEQ ID NO:5), X-Ala$_4$Gly$_3$-Y (SEQ ID NO:6), X-Ala$_3$Leu$_3$-Y (SEQ ID NO:7), X-Ala$_3$Leu$_3$Glu$_2$-Y (SEQ ID NO:8), X-Ala$_3$Leu$_3$Lys$_2$-Y (SEQ ID NO:9), and X-Ala$_3$Leu$_3$Glu$_2$-Y (SEQ ID NO:10), including salts thereof, where X is an optionally substituted $C_{8-24}$ alkyl, alkenyl, or alkynyl; optionally substituted $C_{8-24}$ alkoxy, alkenyloxy, or alkynyloxy; or optionally substituted carbonyl-$C_{8-24}$ alkyl, alkenyl, or alkynyl (such as —$C_{14}H_{29}$, —C(O)$C_{14}H_{29}$, —O$C_{14}H_{29}$, —$C_{15}H_{31}$, —C(O)$C_{15}H_{31}$, —O$C_{16}H_{31}$, —$C_{16}H_{33}$, —C(O)$C_{14}H_{33}$, and —O$C_{16}H_{33}$), and where Y is absent, —NH$_2$, -Glu, -GluIleLysValAlaVal (-EIKVAV, SEQ ID NO:11), -IleLysValAlaVal (-IKVAV, SEQ ID NO:12), -GluArgGlyAsp (-ERGD, SEQ ID NO:13), -LysLysLys (-Lys$_3$), -SerGly (-SG), -Ser(phosphorylated)Gly (—S(phos)G), -AlaGly (-AG), -ArgGlyAsp (-RGD), and -ArgGlyAspSer (-RGDS, SEQ ID NO:14).

Exemplary ECM proteins, saccharides, and carbohydrates include a glycosaminoglycan (e.g., hyaluronic acid), a fiber (e.g., collagen or elastin), a proteoglycan (e.g., heparan sulfate, chondroitin sulfate, or keratan sulfate), a saccharide (e.g., alginate, chitin, glycogen, pectin, N-acetylglucosamine, glucuronic acid, or a starch, as well as combinations of these), a biodegradable polymer (e.g., poly(L-lactic acid), poly(glycolic acid), alginate, or copolymers thereof), fibronectin, or laminin, as well as fragments or derivatives thereof. Further exemplary peptide amphiphiles, ECM proteins, saccharides, and carbohydrates are described in Capito R M et al., "Self-assembly of large and small molecules into hierarchically ordered sacs and membranes," *Science* 2008; 319:1812-6; Carvajal D et al., "Physical properties of hierarchically ordered self-assembled planar and spherical membranes," *Soft Matter* 2010; 6:1816-23; and Chow L W et al., "A bioactive self-assembled membrane to promote angiogenesis," *Biomaterials* 2011; 32:1574-82, each of which is incorporated herein by reference in its entirety.

Other exemplary membrane materials include ultrathin nano-membranes (see, e.g., Miller J J et al., "Lift-off of large-scale ultrathin nanomembranes," *J. Micromech. Microeng.* 2015; 25(1):015011; and Kang E et al., "Large-scale, ultrapliable, and free-standing nanomembranes," *Adv. Mater.* 2013; 25(15):2167-73), collagen films (see, e.g., Lu J T et al., "Thin collagen film scaffolds for retinal epithelial cell culture," *Biomaterials* 2007; 28(8):1486-94), hydrogel sheets (see, e.g., Bruggeman L A et al., "A cell culture system for the structure and hydrogel properties of basement membranes; Application to capillary walls," *Cell. Mol. Bioeng.* 2012; 5(2):194-204), patterned substrates (see, e.g., Frohlich E M et al., "Topographically-patterned porous membranes in a microfluidic device as an in vitro model of renal reabsorptive barriers," *Lab Chip* 2013; 13(12):2311-9; and Esch M B et al., "On chip porous polymer membranes for integration of gastrointestinal tract epithelium with microfluidic 'body-on-a-chip' devices," *Biomed. Microdevices* 2012; 14(5):895-906), commercial ECM products (see, e.g., Badylak S F et al., "Extracellular matrix as a biological scaffold material: Structure and function," *Acta Biomater.* 2009; 5(1):1-13), and layered composite biomaterials (see, e.g., Richert L et al., "Elasticity of native and cross-linked polyelectrolyte multilayer films," *Biomacromolecules* 2004; 5(5):1908-16), which can be used to further tune the culture interface to reflect the physiology of the tissue, where each of these references is incorporated herein by reference in its entirety.

The insert can be employed with one or more sealing layers to provide an insert assembly. In this embodiment, the insert can be configured to provide a fluidic seal (e.g., by being affixed to one or more sealing layers) and to facilitate mechanical handling (e.g., insertion and removal from the assembly, as well as coupling and decoupling from different modules, such as by being composed of a rigid material, such as Mylar™). The handling layer of the insert can include various regions, including an aperture, a periphery of the aperture, a fluidic seal region (e.g., disposed around the aperture and optionally extended to the edge of the handling layer), and a handling region (e.g., surrounding the edge of the handling layer). The fluidic seal region can be configured to provide a fluidic seal and/or to interface with a sealing layer. In one instance, the fluidic seal region is at least 0.2 mm and preferably not greater than 5 mm and would surround the culture region including the cell culture membrane. In another instance, the fluidic seal region is configured to provide no gaps, perforations, nor leaks between the fluidic sealing region, the handling region, and/or the cell culture membrane. In yet another instance, the gaps and/or perforations are significantly smaller than the inherent pore size of the membrane and/or the support of the culture region.

Figure 4A:
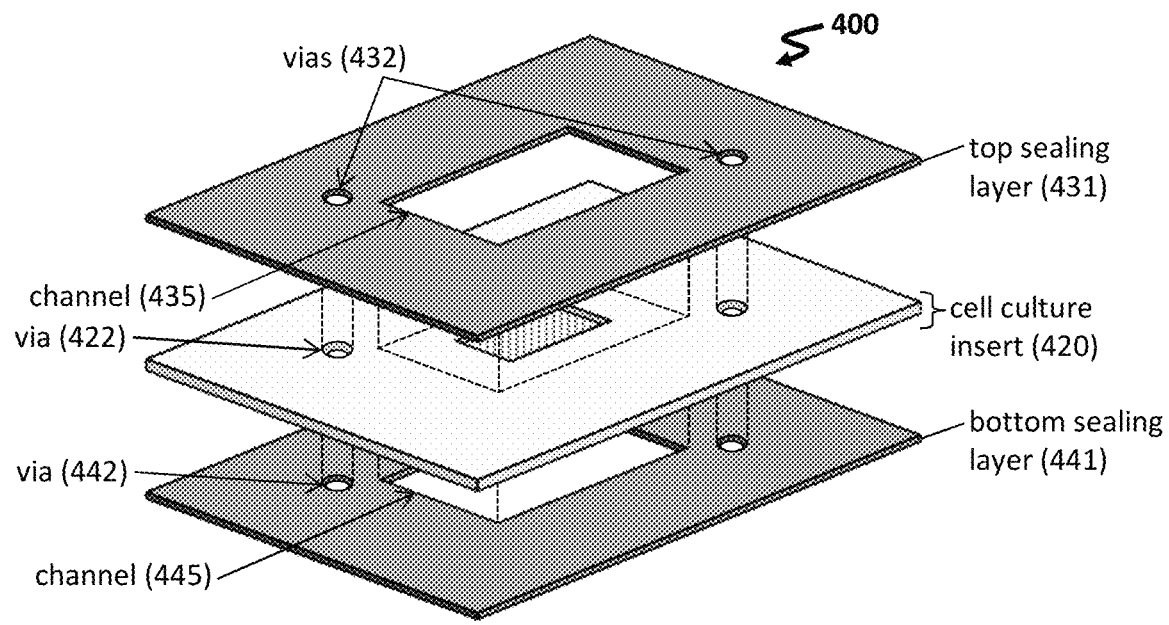
FIG. 4A-4B provides an exemplary insert assembly. Shown are an insert assembly 400 including a cell culture insert 420 disposed between top and bottom sealing layers 431,441 (FIG. 4A); and (B) an aligned insert assembly 4000 (FIG. 4B).

The sealing layer can be configured to be affixed to a surface of the cell culture insert (e.g., a surface of the fluidic seal region of the handling layer). FIG. 4A provides an insert assembly 400 including a cell culture insert 420 disposed between a top sealing layer 431 and a bottom sealing layer 441. As can be seen, a bottom surface of the top sealing layer 431 is configured to contact a top surface of the cell culture insert 420, thereby forming a fluidic seal between the top sealing layer 431 and the cell culture insert 420 and minimize leaking between these two components. Also, the top surface of the bottom sealing layer 441 is configured to contact a bottom surface of the cell culture insert 420, thereby forming a fluidic seal beneath the cell culture membrane.

Figure 4B:
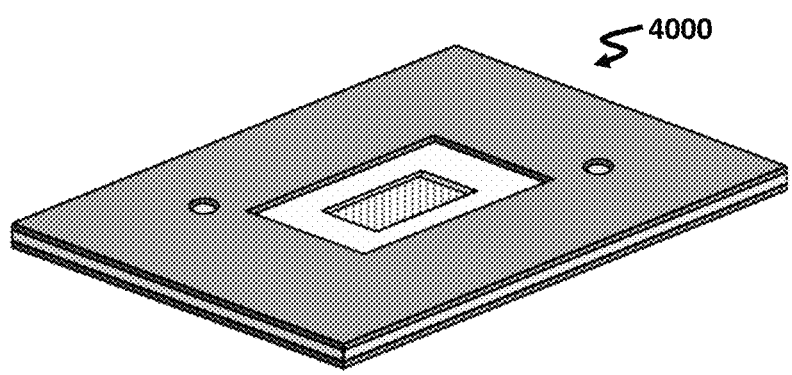

The sealing layer can include one or more fluidic elements (e.g., any described herein) to provide a fluidic network. FIG. 4A provides a top sealing layer 431 having a central channel 435 that provides fluidic access to the underlying culture membrane disposed within the cell culture insert, as well as one or more vias 432 disposed therein to provide a fluidic pathway through the layers of the assembly (e.g., through a via 432 in the top sealing layer 431, into a via 422 in the cell culture insert layer 420, and then into a via 442 in the bottom sealing layer 441). The bottom sealing layer 441 can also include one or more vias 442 and channels 445. Each via and channel can be aligned to provide any useful fluidic pathway in the stacked insert assembly 4000 (FIG. 4B).

Figure 5A:
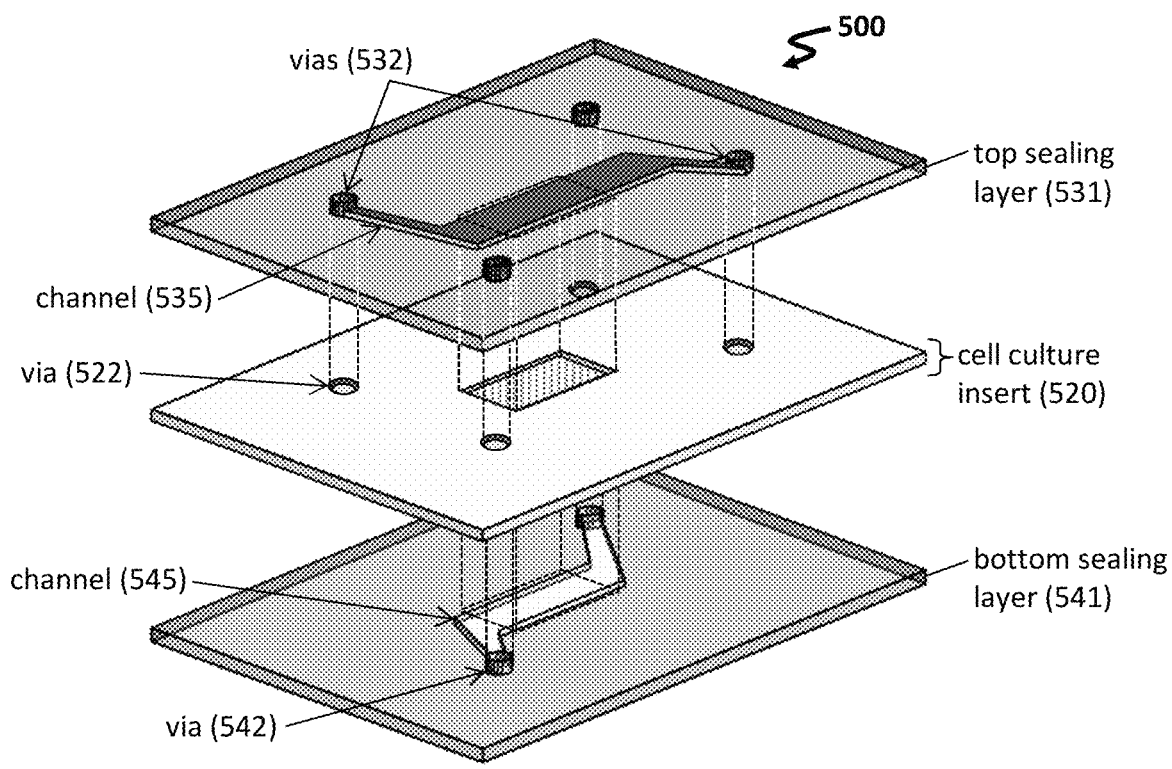
FIG. 5A-5E provides another exemplary insert assembly. Shown are an insert assembly 500 including a cell culture insert 520 disposed between top and bottom sealing layers 531,541 having channels 535,545 (FIG. 5A); an aligned insert assembly 5000 (FIG. 5B); a cross-sectional view along line 5C-5C in FIG. 5B (FIG. 5C); a cross-sectional view along line 5D-5D in FIG. 5B (FIG. 5D); and a cross-sectional view along line 5E-5E in FIG. 5B (FIG. 5E).

FIG. 5A provides an exemplary insert assembly 500 including a top sealing layer 531 having a channel 535 and vias 532, a bottom sealing layer 541 including a channel 545 and vias 542, as well as cell culture insert 520 including vias 522 and configured to be disposed between the top and bottom sealing layers 531,541. The channels 535,545 in the sealing layers can be aligned to provide fluidic access to the membrane provided in the cell culture insert 520. Also, each layer within the insert assembly can include one or more vias that are aligned to provide the desired fluidic path. For instance, the vias 532 in the top sealing layer 531 are aligned with two of the four vias 522 in the cell culture insert, and the vias 542 in the bottom sealing layer 541 are aligned with the other two of the four vias 522 in the cell culture insert.

Figure 5B:
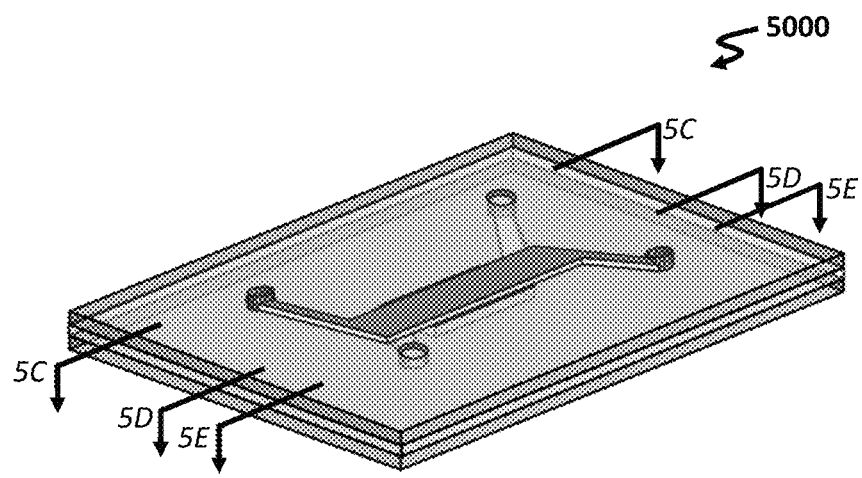
Figure 5C:
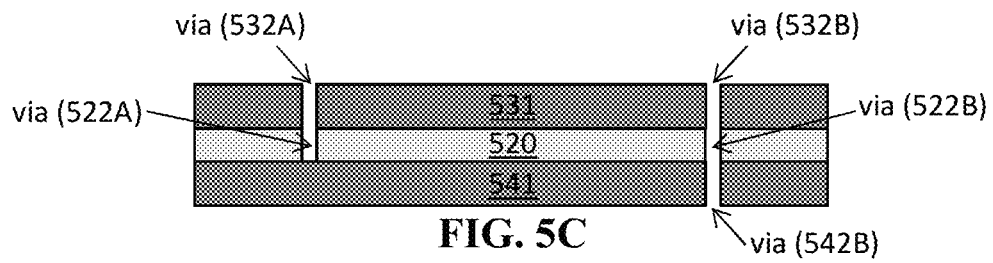
Figure 5D:
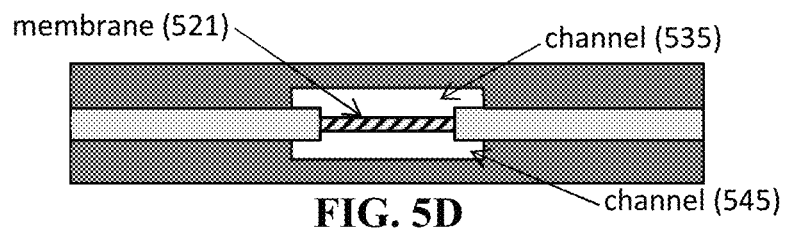
Figure 5E:
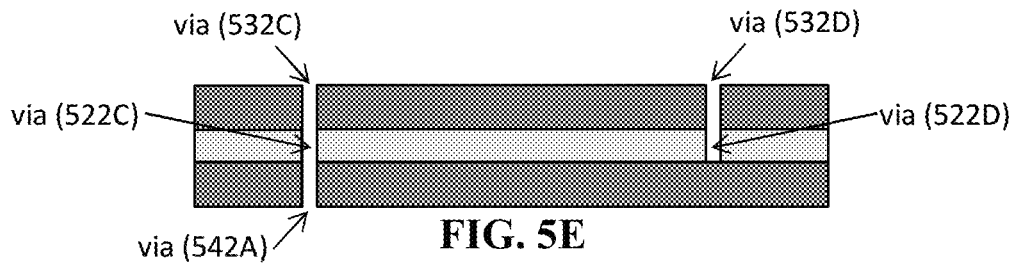

The fluidic elements within the insert and the sealing layers can provide any useful fluidic pathway once the assembly components are aligned. FIG. 5B provides an aligned assembly 5000 having a fluidic pathway. As seen in FIG. 5C-5E, a first via 532A in the top sealing layer 531 provides a fluidic pathway to the via 522A in the cell culture insert 520, into the channel 535 disposed in the top sealing layer 531, to the membrane 521, and then into the via 532D located at the end of the channel 535 in the top sealing layer 531. If the membrane is porous, then the fluidic pathway can travel through the membrane 521, into the underlying channel 545, and to either vias 542A,542B located in the bottom sealing layer 541. Another via 532B located in the top sealing layer 531 provides a fluidic pathway directly to the second channel 545 disposed in the bottom sealing layer 541. For instance, the fluidic pathway can continue from via 532B in the top sealing layer 531, through the via 522B in the cell culture insert 520, into the channel 545 in the bottom sealing layer 541, to the via 542A at the end of the channel 545, to the via 522C in the cell culture insert 520, and then to the via 532C located in the top sealing layer 531. The applied pressure in each of the vias, inlets, and outlets can be calibrated to controlled flow direction, flow rate, flow time, etc.

By including such channels and vias within the sealing layer, agents can be externally provided to an access port in the housing set and internally delivered to the cell culture region. The fluidic pathway within the fluidic network can be controlled by applying force (e.g., pressure) to one or more access ports, inlets, or outlets, thereby controlling the direction of the fluidic pathway that is determined by minimizing pressure difference.

The sealing layer can include one or more adhesive sealing layers. For instance, a sealing layer itself can be composed of an adhesive material having one or more fluidic elements (e.g., channels, vias, etc.) laser cut into the adhesive material. Alternatively, a sealing layer (e.g., a polymer sealing layer, such as a layer formed from a polymer) can include one or more adhesive materials coated on one or more surfaces. In yet another alternative, the adhesive material can be provided in an adhesive sealing layer, which in turn can be employed with a sealing layer composed of a non-adhesive material, such as the polymer poly(dimethylsiloxane) (PDMS). Thus, a plurality of sealing layers can be employed, in which a polymer sealing layer is aligned with one or more adhesive sealing layers. In use, if the adhesive is a pressure-sensitive adhesive, then the transferrable insert can be exposed by peeling apart the various layers within the modular assembly.

For instance, FIG. 1E provides an exemplary modular assembly 1100 having one or more adhesive sealing layers 1161,1162,1163,1164. As can be seen, the adhesive sealing layers are disposed between each layer within the assembly to provide seals that are resistant to fluid leakage. Each adhesive sealing layer can include one or more useful fluidic elements (e.g., channels 1165, vias, etc.), as well as one or more alignment features 1155.

The adhesive material can include any useful reversible adhesive material, e.g., a pressure-sensitive adhesive, a photosensitive adhesive, a heat-sensitive adhesive, or any described herein. If desired, external clamps disposed around the housing set can be employed to provide additional pressure for a gasket seal. Such adhesive sealing layers can be used in combination with any other fasteners described herein (e.g., magnetic fasteners disposed within the housing, and adhesive sealing layers disposed between the housing and the cell culture insert and/or other sealing layers).

Modular Systems

The modular system is composed of one or more modular assemblies, where each assembly is configured to accommodate the same cell culture insert. In use, the system allows the same insert to be transferred and used within various assemblies to conduct different useful assays, cultures, or other useful biochemical modalities.

For use as a modular system, the housing set for each assembly can be configured to be reversibly attached and detached from a universal cell culture insert. Rather than a monolithic assay system that conducts only particular assays, only the housing set can be adapted to conduct particular assays and yet the cell culture insert can be retained.

Figure 6A:
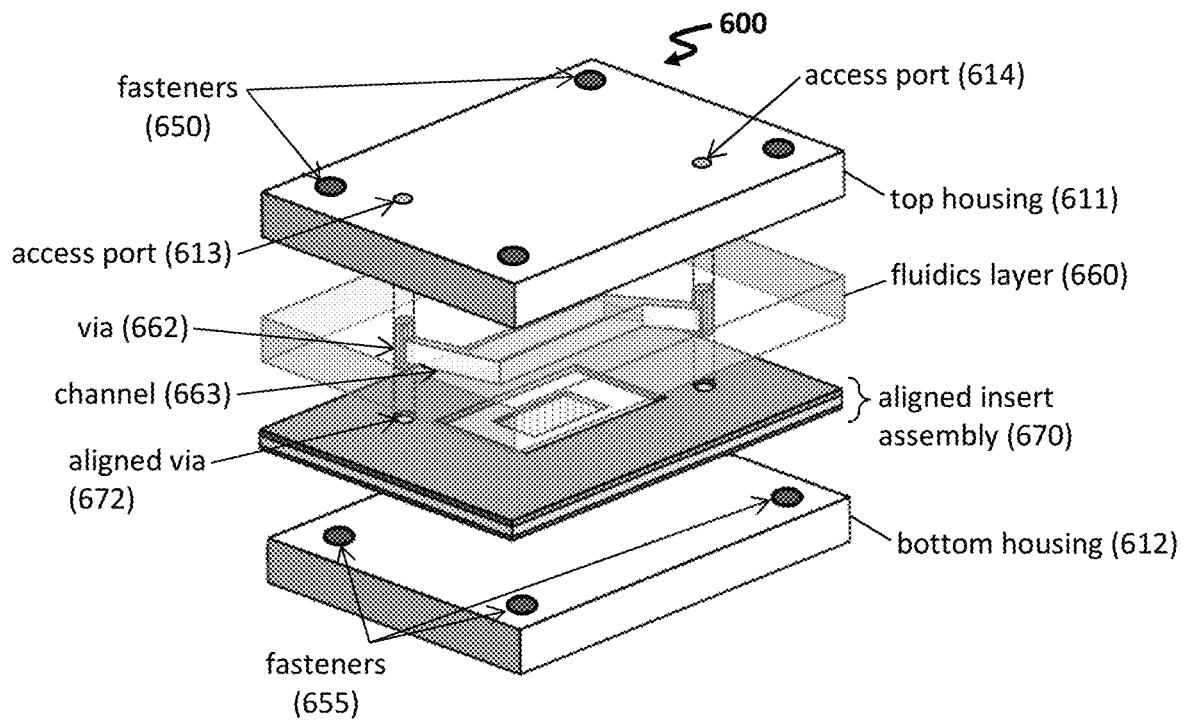
FIG. 6A-6B provides exemplary modular assemblies with a fluidics layer. Shown are an exemplary modular assembly 600 with aligned components (FIG. 6A); and another exemplary modular assembly 6000 in which the bottom housing 6012 has a recess 6015 to accommodate the insert assembly 6080 (FIG. 6B).
Figure 6B:
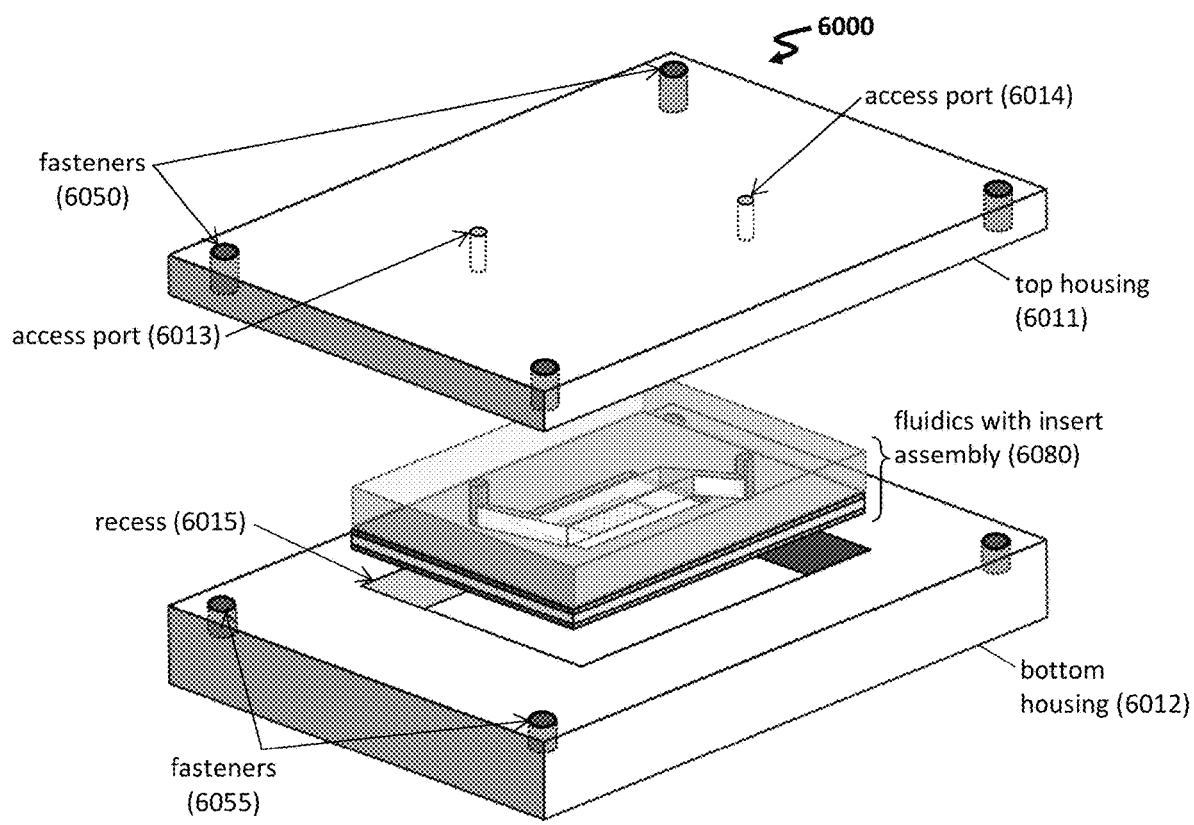

FIG. 6A-6B provides exemplary modular assemblies that can be included in a modular system. FIG. 6A provides a modular assembly 600 including a detachable housing set, which in turn includes a top housing 611 and a bottom housing 612. In this particular non-limiting system, fasteners 650,655 (e.g., magnetic fasteners) are disposed within the housing set to be reversibly attached the top housing 611 to the bottom housing 612. The assembly 600 employs an aligned insert assembly 670 having an aligned via 672 to provide a fluidic pathway from the access port 613 in the top housing 611, to the via 662 and the channel 663 in the fluidics layer 660, to the membrane within the insert assembly 670, back through another via in the fluidics layer 660, and then to the access port 614 (an outlet) in the top housing 611. To provide additional functionality, a fluidic layer 660 is employed to direct agents to the membrane of the insert assembly. In addition, to minimize leakage between components, one or more sealing layers (e.g., any described herein) can be disposed between the components within the assembly.

As can be seen, the same aligned insert assembly 670 from a first modular assembly 600 can be detached and then transferred to a second modular assembly 6000 in FIG. 6B. The second modular assembly 6000 provides a different housing set, in which the top housing 6011 includes two access ports 6013,6014 and fasteners 6050; and the bottom housing 6012 includes fasteners 6055 and a recess 6015 to accommodate the fluidics with the insert assembly 6080.

Another exemplary modular system is described in FIG. 7A-7D, in which each modular assembly in these figures can be adapted to employ the same universal cell culture insert. These modular assemblies employ fasteners disposed within the housing (e.g., magnetic fasteners within the housing, in which a first fastener in the top housing is configured to be reversibly attached to a second fastener in the bottom housing). Alternatively, the assemblies can be modified to employ adhesive sealing layers to perform as fasteners. In addition, each module can include any useful sealing layers, optionally including fluidic elements, that are designed for the module's particular use and as well as for affixation to the transferrable insert.

Figure 7A:
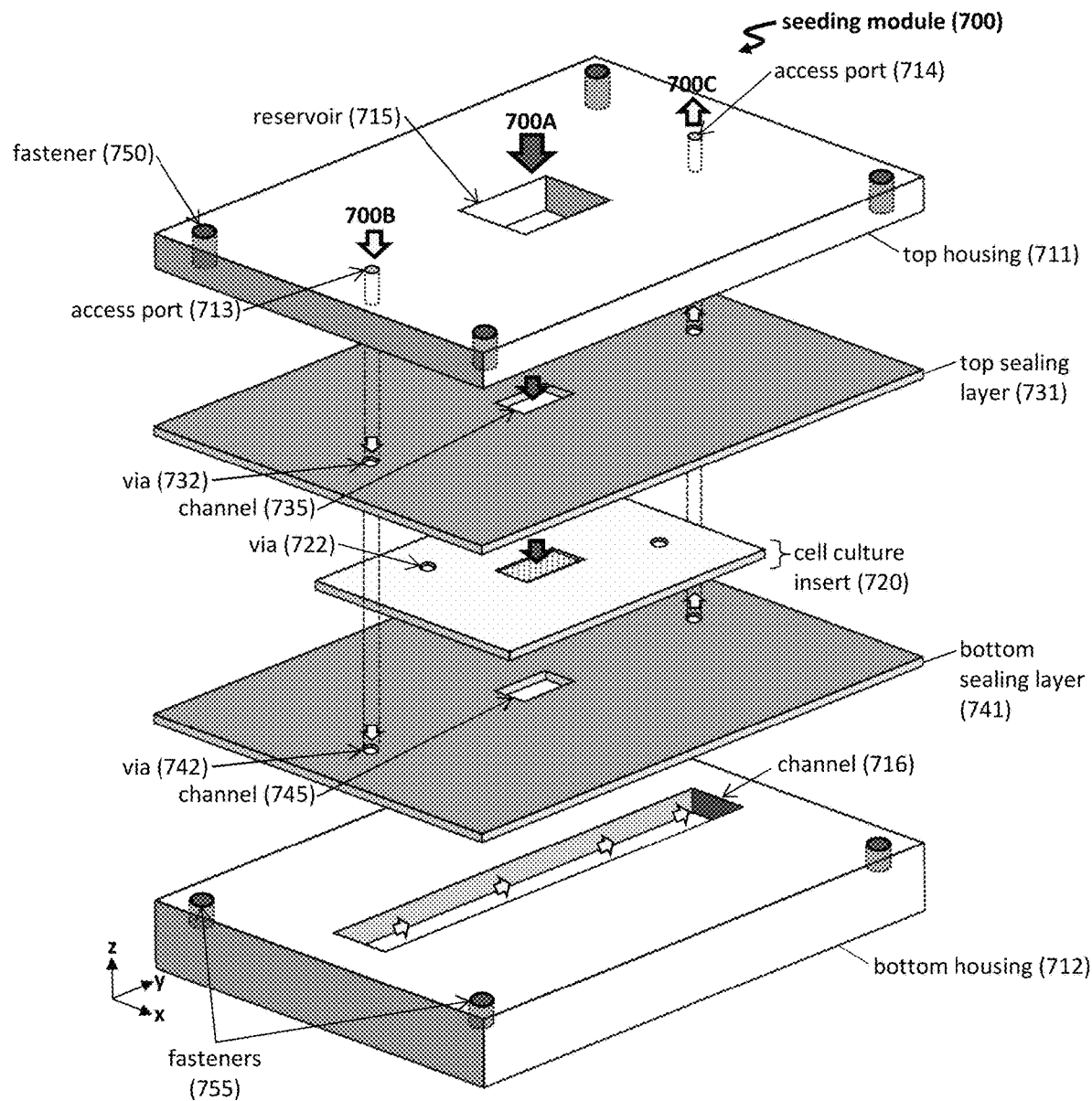
FIG. 7A-7D provides an exemplary modular system having different housing sets configured to accommodate the same transferrable cell culture insert. Shown are an exemplary seeding module 700 having a detachable housing set configured to deliver one or more cell samples (FIG. 7A); an exemplary culture module 7000 having a detachable housing set configured to deliver and/or collect agents to a top surface of the insert 7020 (FIG. 7B); another exemplary culture module 7100 having a detachable housing set configured to deliver and/or collect agents to both top and bottom surfaces of the insert 7120 (FIG. 7C); and an exemplary perfusion module 7300 configured to be attached to an assembled culture module 7200 (FIG. 7D).

FIG. 7A provides an exemplary modular assembly 700 employed as a seeding module.

The seeding module can be configured to deliver one or more cells to the cell culture membrane disposed within the transferrable insert, as well as to maintain cell growth upon that membrane. As can be seen, the module 700 includes a top housing 711 having a plurality of first fasteners 750, where each fastener is disposed in each corner of the top housing. The top housing 711 also include one or more fluidic elements to deliver and maintain cells, including a reservoir 715 to allow top loading of one or more cells and two access ports 713,714 to deliver agents (e.g., cell culture media, buffer, nutrients, etc., such as those described herein) to the cell(s). The bottom housing 712 includes a plurality of second fasteners 755 and a channel 716 configured to underlie the cell culture insert 720.

The top and bottom housing 711,712 are configured to accommodate the cell culture insert 720, as well as one or more optional sealing layers. In this particular seeding module 700, the assembly includes a top sealing layer 731 and a bottom sealing layer 741, in which each sealing layer is configured to be disposed on a surface of the insert 720. The insert 720 can further include one or more vias 722 that are available to provide a fluidic path, if desired.

Fluidic pathways through the module can be designed to include any useful fluidic network. In particular, each component of the module can include vias, channels, and access ports that can each be aligned to provide a desired fluidic pathway. For instance, as seen in FIG. 7A, a first fluidic pathway 700A (dark gray arrows) is configured to provide access to the cell culture membrane within the insert 720. This first fluidic pathway 700A is provided by a reservoir 715 disposed in the top housing 711 and a channel 735 disposed in the top sealing layer 731, in which the channel 735 overlies the membrane in the insert 720 and provides fluidic communication with this membrane. Excess fluid can travel through a channel 745 in the bottom sealing layer 741 and into the underlying channel 716.

Other fluidic pathways can be implemented. In one instance, a second fluidic pathway 700B,700C (light gray arrows) is configured to provides access to a channel 716 underlying the cell culture membrane, in which one access port 713 provides an inlet to the beginning of the fluidic pathway 700B and another access port 714 provides an outlet to the end of the fluidic pathway 700C. This second fluidic pathway 700B is provided by a first access port 713, a first upper via 732 disposed in the top sealing layer 731, and a first lower via 742 disposed in the bottom sealing layer 741. The fluidic pathway then continues through the channel 716 disposed in the bottom housing 712, up into a second lower via located in the bottom sealing layer 741, then into a second upper via located in the top sealing layer 731, and up into the access port 714 located in the top housing 711, thereby ending the fluidic pathway 700C.

Figure 7B:
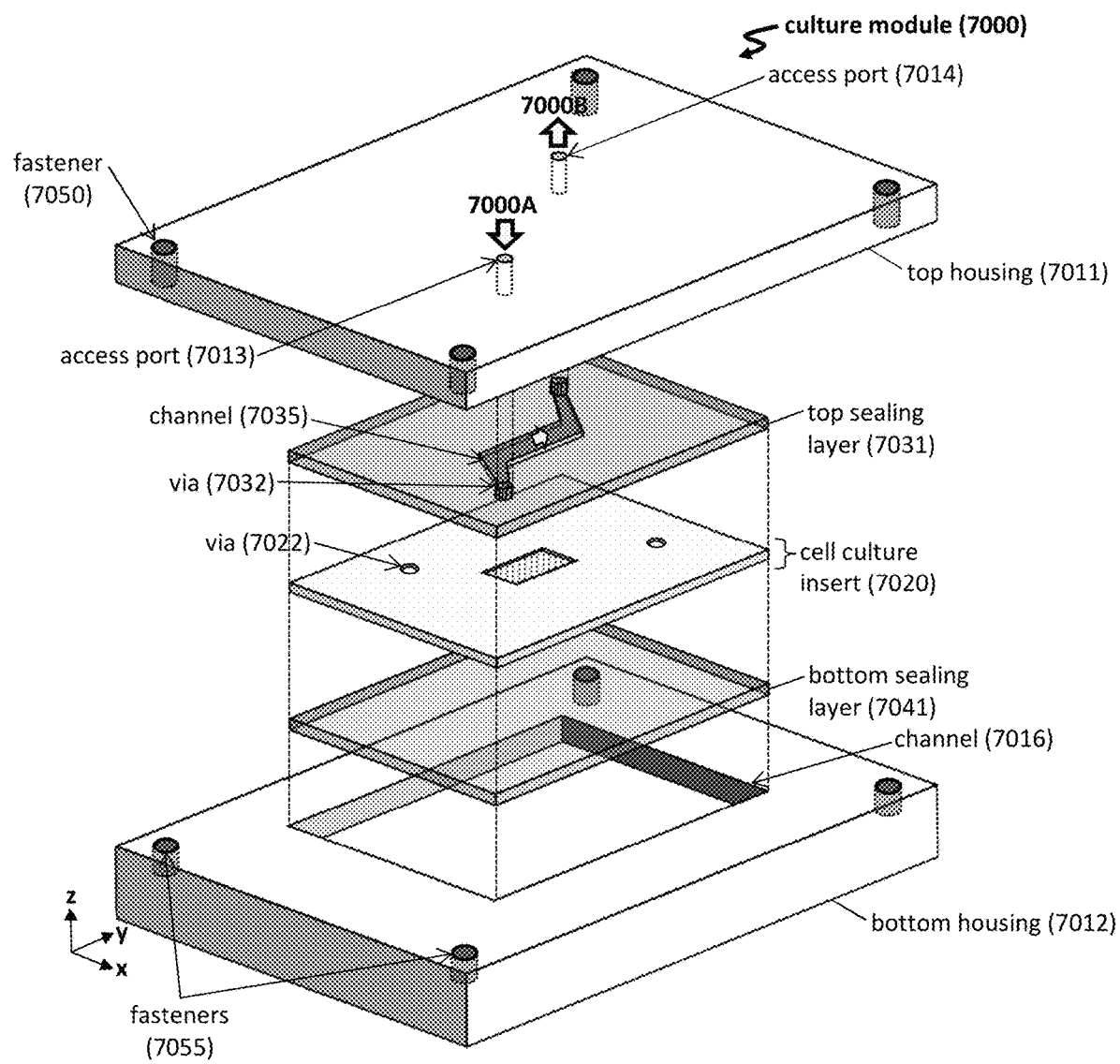

FIG. 7B provides another modular assembly configured as a culture module 7000. As can be seen, the culture insert 7020 (with vias 7022) for the culture module 7000 has the same configuration as the culture insert 720 (with vias 722) for the seeding module 700. Thus, the insert is a universal insert that can be accommodated by different detachable housing sets.

In FIG. 7B, the housing set is configured to provide a culture module 7000, in which the housing set includes a top housing 7011 having a plurality of first fasteners 7050 and a bottom housing 7012 having a plurality of second fasteners 7055, where each fastener in the top housing is configured to be reversibly attached to a fastener in the bottom housing. The top housing 7011 includes two access ports 7013,7014 to deliver one or more agents to the insert 7020; and the bottom housing 7012 includes a channel 7016 configured to accommodate the insert 7020 and its associated sealing layers 7031,7041.

The module 7000 also includes a top sealing layer 7031 and a bottom sealing layer 7041, in which these sealing layers are configured to facilitate long-term maintenance and testing of the cell culture. As can be seen, the top sealing layer 7031 of the culture module 7000 includes a channel 7035 to provide transverse access (e.g., along the y-axis in FIG. 7B) across the membrane of the insert 7020, whereas the top sealing layer 731 of the seeding module 700 includes a channel 735 to provide direct top-side access (e.g., along the z-axis in FIG. 7A) to the membrane of the insert 720. The sealing layers, as well as housing sets, can be designed with any useful combination of fluidic elements to provide the desired fluidic pathway and desired access to the cell culture.

Fluidic pathways through the culture module can include those that deliver agents to the cell(s) disposed on the cell culture membrane, as well as those that collect analytes released by the cell(s). As seen in FIG. 7B, a fluidic pathway 7000A,7000B (light gray arrows) is configured to provide access to the cells disposed upon the cell culture membrane. The access port 7013 in the top housing 7011 provides an inlet to the beginning of the fluidic pathway 7000A and another access port 7014 provides an outlet to the end of the fluidic pathway 7000B. The fluidic pathway 7000A,7000B is provided by a first access port 7013, to a first via 7032 disposed in the top sealing layer 7031, through a channel 7035 within the top sealing layer 7031, then through another via located at the end of this channel 7035, and then through the second access port 7014 located in the top housing 7011.

Figure 7C:
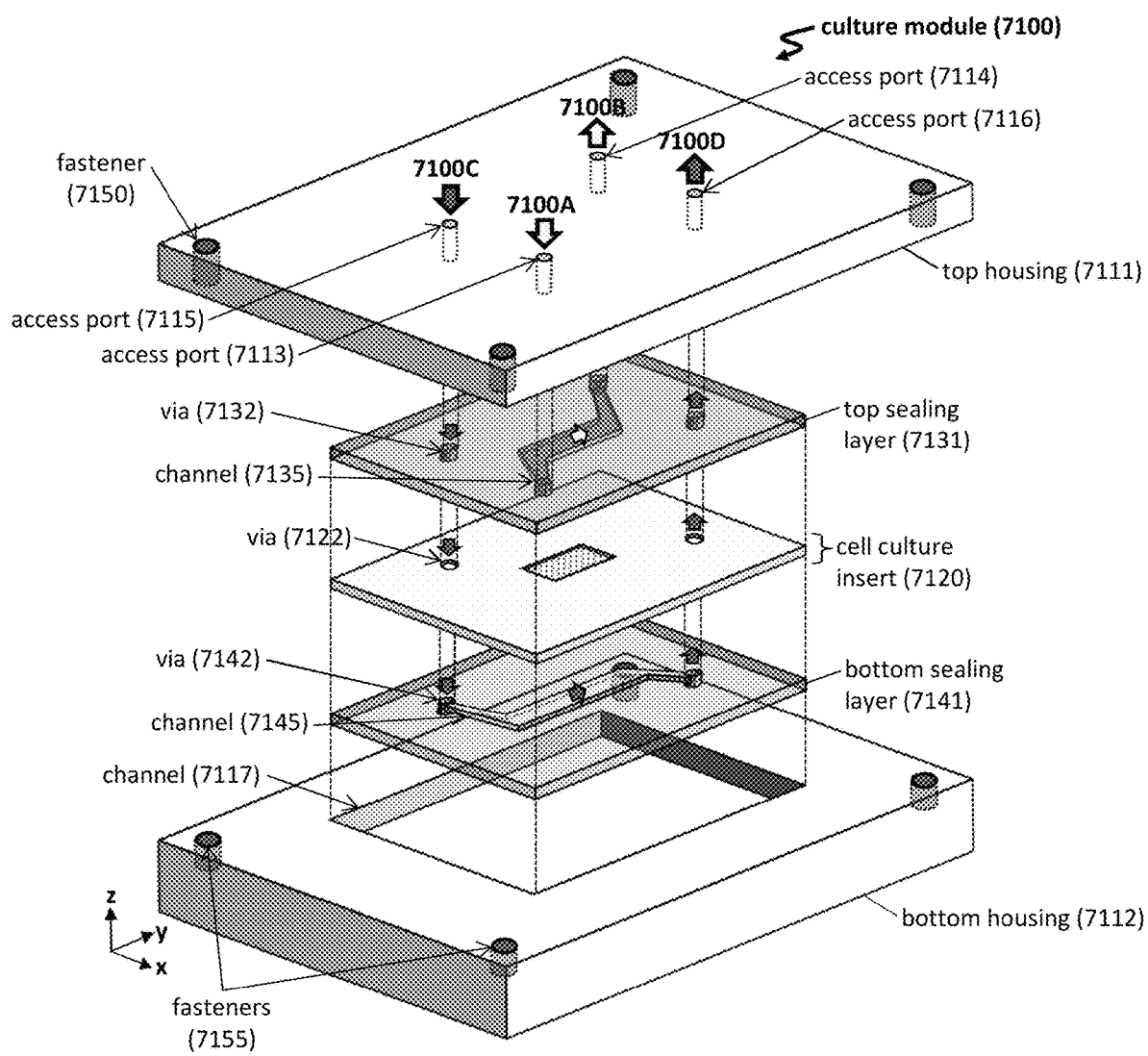

The culture module can include any useful combination of fluidic elements. FIG. 7C provides another exemplary culture module 7100 including fluidic elements to access both the top and bottom interfaces (e.g., apical and basolateral interfaces) of the cell culture disposed on the cell culture membrane in an independent manner. Here, the sealing layers include one or more fluidic elements to direct the fluidic pathway above and below the membrane. The top sealing layer 7131 includes a channel 7135 configured to be disposed above the cell culture membrane of the insert 7120 and vias disposed at the end of the channel 7135. The bottom sealing layer 7141 includes a channel 7145 configured to be disposed below the membrane of the insert 7120 and vias 7142 disposed at the end of the channel 7145.

Two particular fluidic pathways can be established within the culture module 7100. A first fluidic pathway 7100A, 7100B (light gray arrows) provides access to the top side of the membrane. This fluidic pathway begins at an access port 7113 located in the top housing 7111, continues to a via in the top sealing layer 7131, through the channel 7135 in the top sealing layer 7131, to another via in the top sealing layer 7131, and then through the access port 7114 in the top housing 7111. A second fluidic pathway 7100C,7110D (dark gray arrows) provides access to the bottom side of the membrane. This fluidic pathway begins at another access port 7115 located in the top housing 7111, to another via 7132 in the top sealing layer 7131, through another via 7122 in the cell culture insert 7120, to yet another via 7142 in the bottom sealing layer 7141, and then through the channel 7145 disposed beneath the cell culture membrane. Within this channel 7145, analytes released by the cell(s) can be collected and delivered outside of the assembly. For this delivery, the fluidic pathway continues from the channel 7145, to a via located in the bottom sealing layer 7141, up through a via located in the insert 7120, to another via located in the top sealing layer 7131, and then out to the access port 7116 located in the top housing 7111.

To allow reversible attaching and detaching of the housing set, the culture module 7100 includes a top housing 7111 having a plurality of first fasteners 7150 and a bottom housing 7112 having a plurality of second fasteners 7155 and a channel (or reservoir) 7117 to accommodate the culture insert 7120 and its sealing layers 7131,7141.

Delivery of agents through the modular assembly can be facilitated in any useful manner. For instance, active pumps can be employed to provide pressure-driven flow (e.g., applied positive or negative pressure) through the fluidic network established by different components within the assembly. Such active pumps include those that require a power source or another external apparatus, in which exemplary active pumps include use of osmotic membranes to drive flow, a motorized syringe pump, a vacuum pump, a peristaltic pump, an electrokinetic pump, or a centrifugal pump. In another instance, passive pumps are employed. Such passive pumps include use of physical forces to drive flow, such as a gravity-drive pump, a surface tension-based pump, or a pneumatic pressure pump. Additional pumps are described in, e.g., Byun C K et al., "Pumps for microfluidic cell culture," *Electrophoresis* 2014; 35(2-3):245-57; Kim T et al., "On-chip three-dimensional tumor spheroid formation and pump-less perfusion culture using gravity-driven cell aggregation and balanced droplet dispensing," *Biomicrofluidics* 2012; 6:034107 (10 pp.); Kim T et al., "A pumpless cell culture chip with the constant medium perfusion-rate maintained by balanced droplet dispensing," *Lab Chip* 2011; 11:1825-30; Lee D W et al., "A pumpless perfusion cell culture cap with two parallel channel layers keeping the flow rate constant," *Biotechnol. Prog.* 2012; 28(6):1466-71; and U.S. Pat. Nos. 6,743,399 and 8,748,180, each of which is incorporated herein by reference in its entirety. In some embodiments, one or more of these pumps, combined with one or more valves, channels, or vias, are integrated into a modular assembly for perfusion (e.g., by use of a perfusion module).

Figure 7D:
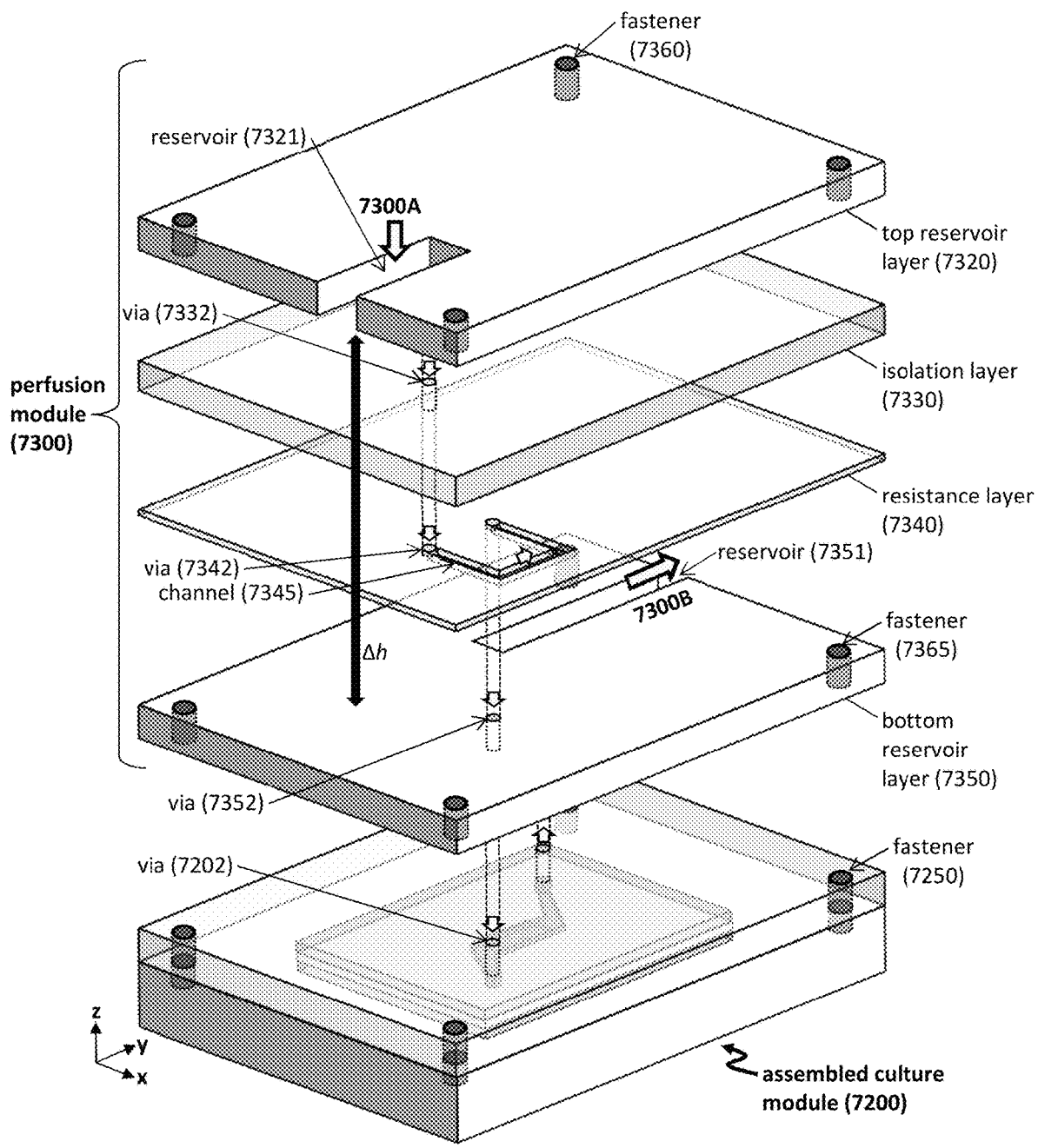

In one instance, the modular system includes a perfusion module configured to be reversibly attached and detached from another modular assembly (e.g., a seeding module or a culture module, such as any described herein). FIG. 7D provides an exemplary perfusion module 7300 configured to be reversibly attached to an assembled culture module 7200. As can be seen, the perfusion module 7300 is also configured to be in fluidic communication with the culture module 7200, in which an outlet of a via 7352 in the bottom reservoir layer 7350 of the perfusion module 7300 is configured to be aligned with a via 7202 of the assembled culture module 7200; and in which a reservoir 7351 of the perfusion module 7300 is configured to be aligned with another via located on a top surface of the assembled culture module 7200.

To facilitate reversible attachment and detachment of the housing set for the perfusion module, the perfusion module 7300 includes fasteners 7360 in the top reservoir layer 7320 and additional fasteners 7365 in the bottom reservoir layer 7350. Furthermore, to facilitate easy attachment and detachment of the perfusion module 7300 to the culture module 7200, the fasteners 7360,7365 in the perfusion module 7300 can be configured to be reversibly attached and detached from the fasteners 7250 in the culture module 7200 (e.g., configured by aligning magnetic poles and fields to facilitate magnetic attraction between the fasteners in the perfusion module to that in the culture module). In another embodiment, a fastener 7365 is a magnet, and the other fasteners 7360,7250 are ferromagnetic metals.

The perfusion module can include any useful combination of fluidic elements to promote fluid flow. For instance, fluid flow can occur when a pressure difference is present between two reservoirs, and gravity acts to equalize this pressure difference. When this pressure difference arises from a height difference between the two reservoirs, then gravity-driven flow will occur until the height difference is equalized. The reservoirs can be oriented in any useful manner, such as horizontally oriented reservoirs (e.g., where the major axis of the reservoir is aligned along the y-axis in FIG. 7D). As seen in FIG. 7D, the reservoirs 7321,7351 are oriented horizontally and separated by a height difference $\Delta h$ (indicated by a black, double-headed arrow). Such horizontally oriented reservoirs are useful because gravity-driven flow from a first reservoir 7321 to a second reservoir 7351 occurs at a constant flow rate.

As seen in FIG. 7D, the perfusion module 7300 include a top reservoir layer 7320 having a first horizontally oriented reservoir 7321; an underlying isolation layer 7330 including a via 7332; a resistance layer 7340 including a channel 7345 and vias 7342 disposed at the end of the channel; and a bottom reservoir layer 7350 including a second horizontally oriented reservoir 7351. Each of these layers can be configured to provide the desired flow rate, flow volume, flow time, etc. For instance, the isolation layer can be configured to provide the desired height difference, and the resistance layer can be configured to provide a channel with the appropriate length and dimensions to control the perfusion rate or flow rate.

The fluidic pathway 7300A,7300B (light gray arrows) within the perfusion module 7300 provides fluid flow through the culture module 7200. The fluidic pathway beings at the reservoir 7321 in the top reservoir layer 7320, through a via 7332 located in the isolation layer 7330, into the vias 7342 and the channel 7345 in the resistance layer 7340, and then into the via 7352 located in the bottom reservoir layer 7350. This fluidic pathway continues from the perfusion module 7300 into the culture module 7200 by way of one via 7202 into the culture module 7200 and then out of another via in the culture module 7200. After pumping through the culture module, the fluidic pathway continues back through the perfusion module 7300 and into the reservoir 7351 in the bottom reservoir layer 7350.

Figure 8:
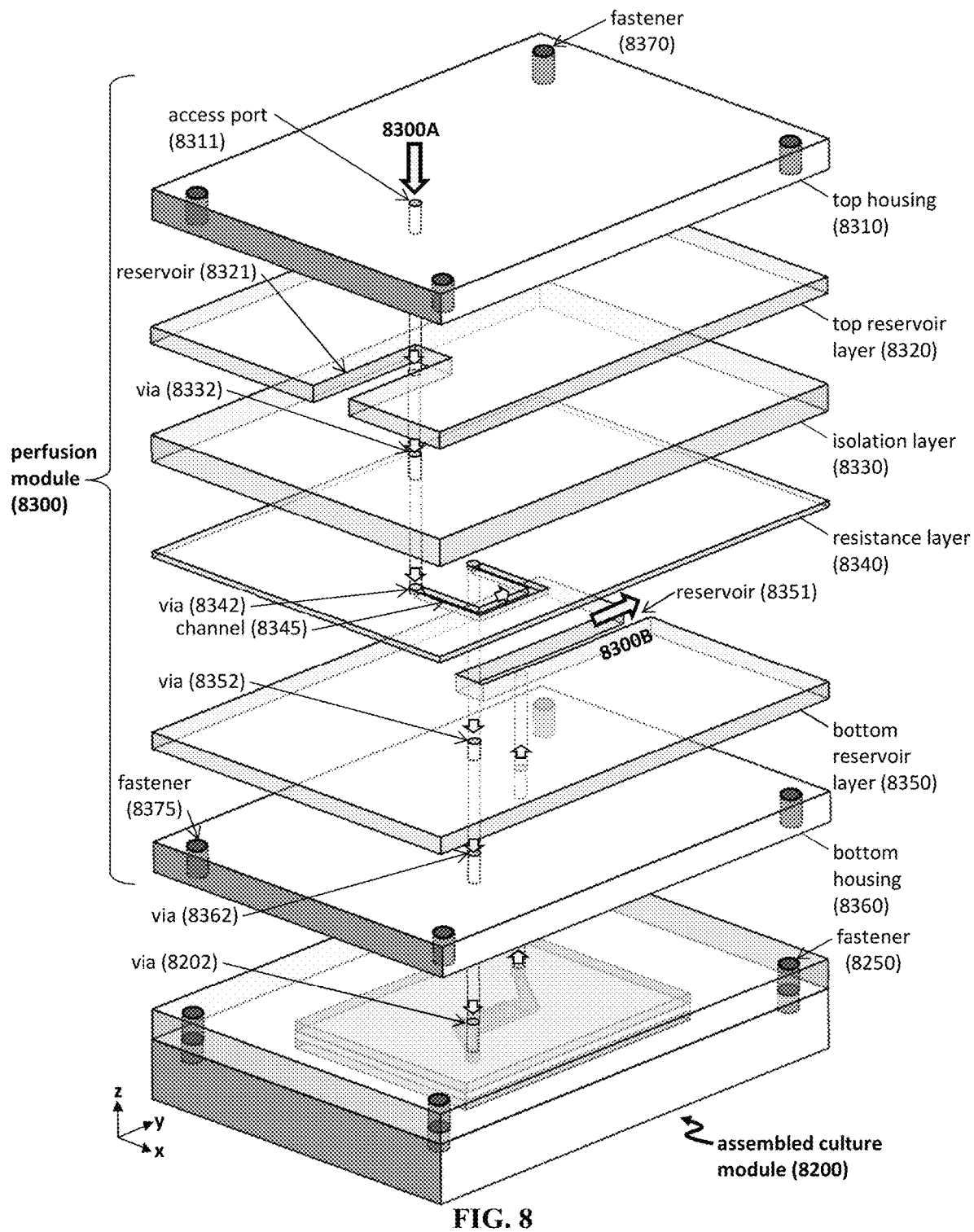
FIG. 8 provides another exemplary perfusion module 8300 configured to be attached to an assembled culture module 8200.

As can be seen, the reservoirs, vias, and channels are aligned to provide the desired fluidic network that connects the perfusion module to another modular assembly and that provides the desired flow rate and time. The perfusion module can optionally include a housing set. FIG. 8 provides an exemplary perfusion module 8300 configured to be reversibly attached to an assembled culture module 8200. As can be seen, the perfusion module 8300 includes fasteners 8360 in the top housing 8310 and additional fasteners 8365 in the bottom housing 8360.

Furthermore, to facilitate easy attachment and detachment of the perfusion module 8300 to the culture module 8200, the fasteners 8370,8375 in the perfusion module 8300 can be configured to be reversibly attached and detached from the fasteners 8250 in the culture module 8200. Fluid flow from the perfusion module 8300 enters into and exits from the culture module 8200 by way of vias 8202.

All components of the perfusion module can be located between a top housing and a bottom housing. As seen in FIG. 8, the perfusion module 8300 includes a top housing 8310 having an access port 8311, a top reservoir layer 8320 having a horizontally oriented reservoir 8321, an isolation layer 8330 having a via 8332, a resistance layer 8340 having a channel 8345 with vias 8342 at the end of the channel 8345, a bottom reservoir layer 8350 having a via 8352 and a reservoir 8351, and a bottom housing 8360 having a via 8362. The fluidic pathway 8300A,8300B (light gray arrows) begins at the access port 8311 in the top housing 8310, continues to the reservoir 8321, through the via 8332 in the isolation layer 8330, down to the vias 8342 and channel 8345 in the resistance layer, to the via 8352 in the bottom reservoir layer 8350, to the via 8362 in the bottom housing 8360, and then into and out of the culture module 8200, up through the via in the bottom housing 8360, and then out to the reservoir 8351 in the bottom reservoir layer 8350. The reservoirs, vias, and channels can be aligned to provide any useful fluidic pathway.

Methods of Forming a Transferrable Insert

The transferrable insert can be formed in any useful manner. For instance, as described herein, the insert can be formed by laminating one or more different components. In one example, the cell culture membrane can be laminated to the handling layer. In another example, the cell culture membrane is laminated between a top handling layer and a bottom handling layer. In yet another example, the handling layer is formed by laminating different materials, such as to provide a porous material in proximity to a periphery of an aperture disposed in the handling layer and to provide a non-porous material in a portion of the handling layer configured for manipulating or transferring the insert. Exemplary inserts are described herein, as well as in FIG. 3A-3F. An additional insert is provided in FIG. 19A, in which a porous support is provided in proximity to a periphery of the aperture or cut-out region. This porous support allows a self-assembled membrane to be tethered to the handling layer by interleaving into the porous support, as well as to be suspended within the aperture.

The membranes can be formed in any useful manner. The membrane of the insert can be formed by reacting one or more precursor agents that are configured to react and form a self-assembled membrane. The method can include placing an aperture of a handling layer in contact with one or more precursor agents; and forming the self-assembled membrane disposed within the aperture and/or in proximity to the aperture. The handling layer can include a porous region (e.g., in which a periphery of the aperture further includes a porous material, a cross-section around the periphery of the aperture includes a porous material, a portion of the handling layer includes a porous region, or the entire handling layer includes a porous region). If such a porous region is present, then one or more fibers of the self-assembled membrane can be interleaved into the porous material surrounding the periphery of the aperture or surrounding a portion of the periphery.

Any useful precursor agents can be employed in the methods herein, in which exemplary precursor agents include a peptide amphiphile, an ECM protein, a saccharide (e.g., hyaluronic acid), or a carbohydrate, as well as a component thereof. The precursor agents generally require a particular reaction time in order to form a membrane composed of fibers. The handling layer can be incubated with the one or more precursor agents for a time sufficient to allow self-assembly of fibers within the open region of the aperture and/or the porous material present in the handling layer or a portion of the handling layer. In addition, the incubation time can be optimized to provide a self-assembled membrane to establish a desired thickness of self-assembled membrane and/or to allow the fibers to interleave through the porous periphery of the aperture, such that the fibers are tethered to the insert. Optionally, the tethered self-assembled membrane can be rinsed (e.g., to remove any excess precursor agent(s)).

The aperture can be contacted with the precursor agent(s) in any useful manner. For instance, the aperture can be placed to be in contact with a first precursor agent on a first surface of the handling layer and a second precursor agent on a second surface of the handling layer. In this way, the interface between the first and second precursor agents is positioned to be located within the aperture, and the interfacial reaction occurs to form a self-assembled membrane within the aperture.

Figure 20A:
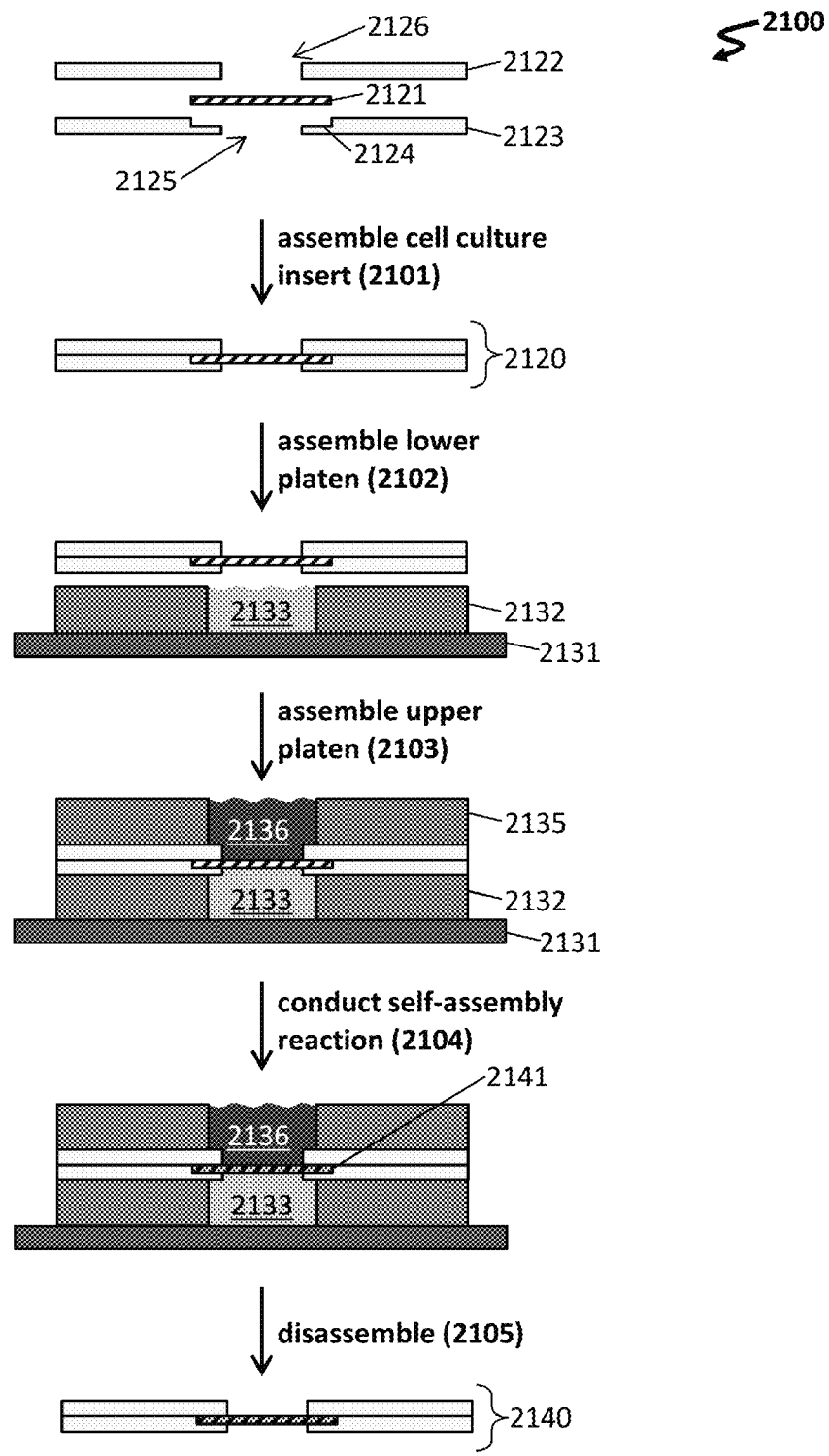
FIG. 20A-20D shows exemplary methods of fabricating a self-assembled membrane for a cell culture insert. Provided are an exemplary method 2100 for depositing a self-assembled membrane using platens 2132,2135 (FIG. 20A); another exemplary method 2200 for depositing a self-assembled membrane within an aperture 2225 of an insert 2220 (FIG. 20B); yet another exemplary method 2300 for depositing a self-assembled membrane within an aperture 2325 of an insert 2323 (FIG. 20C); and an exemplary method for providing a stacked cell culture assembly 2550 (FIG. 20D).

Any useful apparatus can be used to form the membrane within the aperture. Such an apparatus can include the use of platens to deliver the precursor agents to the aperture. In one instance, the handling layer can include a porous scaffold disposed within the aperture. FIG. 20A provides an exemplary method 2100 including assembling 2101 the cell culture insert, assembling 2102 the lower platen, assembling 2103 the upper platen, conducting 2104 the self-assembly reaction, and disassembling 2105 the platen to provide the insert with a self-assembled membrane 2140. The assembling step 2101 can include laminating a porous support 2121 between a top handling layer 2122 having an aperture 2126 and a bottom handling layer 2123 having another aperture 2125. Optionally, the bottom handling layer 2123 can include a rim 2124 to support the porous support 2121.

In a subsequent assembling step 2102, the insert 2120 is placed above a lower platen 2132 with an optional substrate 2131, in which the platen 2132 includes a first precursor agent 2133. In a later assembling step 2103, an upper platen 2135 is placed above the insert 2120, in which the upper platen 2135 includes an orifice that provides a second precursor agent 2136.

The interface between the first and second precursor agents occurs upon the porous support. At this interface, the first and second precursor agents polymerize to form one or more micelles or fibers (e.g., nanofibers). Upon conducting 2104 a self-assembly reaction, the polymerized fibers are deposited upon and/or into the porous substrate, thereby forming a cell culture membrane 2141. Finally, the apparatus is disassembled 2105 to provide the insert 2140 including the cell culture membrane 2141.

Figure 20B:
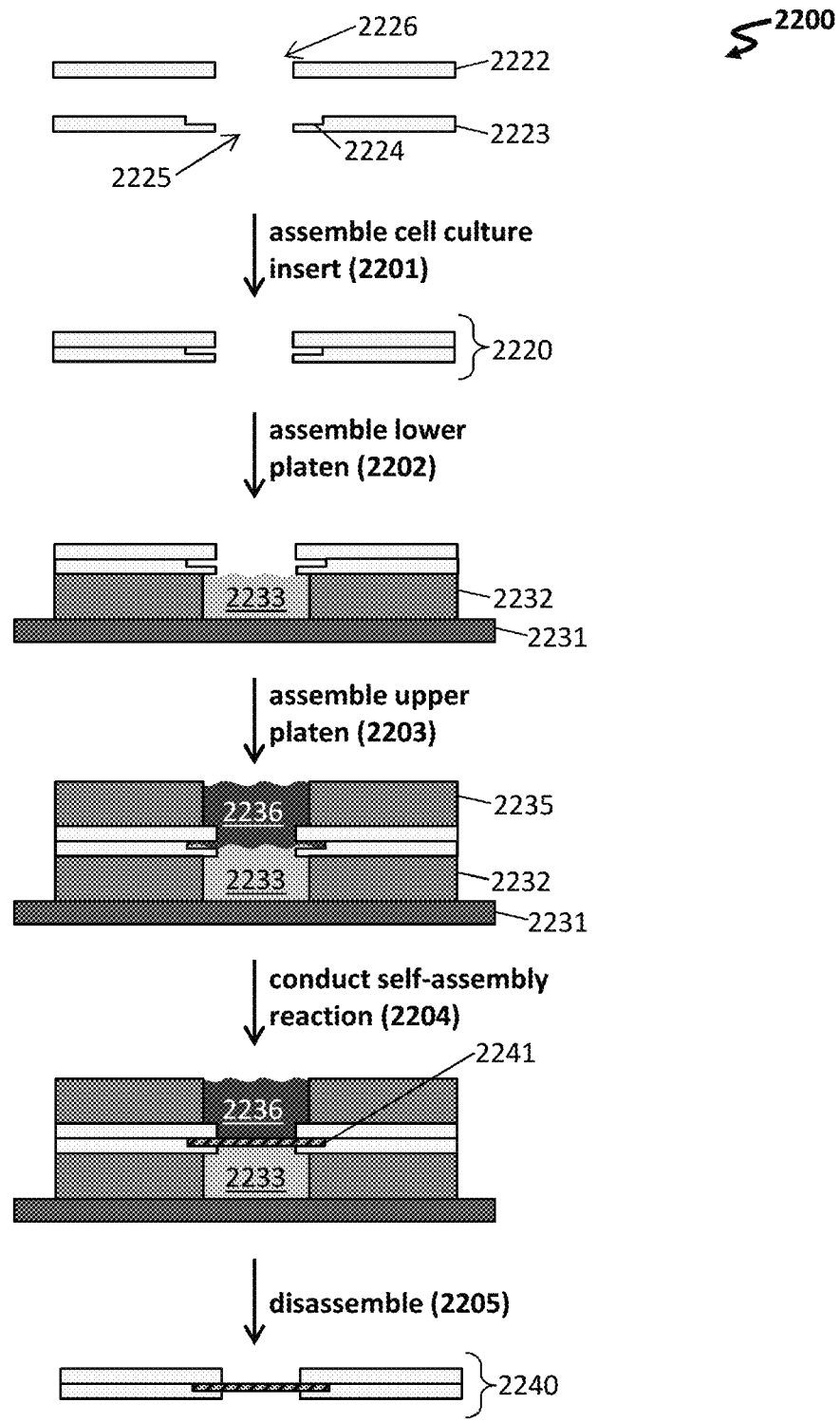

In another instance, the handling layer includes an empty aperture, and the membrane is formed within that aperture to form a suspended membrane. FIG. 20B provides an exemplary method 2200 including assembling 2201 the cell culture insert, assembling 2202 the lower platen, assembling 2203 the upper platen, conducting 2204 the self-assembly reaction, and disassembling 2205 the platens to provide the insert with a self-assembled membrane 2240. The first assembling step 2201 includes providing an insert 2220 having a top handling layer 2222 with an aperture 2226 and a bottom handling layer 2223 with an aperture 2225 and an optional rim 2224. The rim 2224 can optionally include a porous support material, and the remaining portion of the handling layer 2223 can include a porous or non-porous material. The remaining assembling steps include assembling a lower platen 2232 and associated optional substrate 2231 including the first precursor agent 2233; and assembling an upper platen 2235 including the second precursor agent 2236 above the insert 2220. Then, the self-assembly reaction is conducted 2204 at the interface of the precursor agents, thereby forming a membrane 2241 within the insert 2220. Finally, the apparatus is disassembled 2205 to provide the final insert having a self-assembled membrane 2240.

Figure 20C:
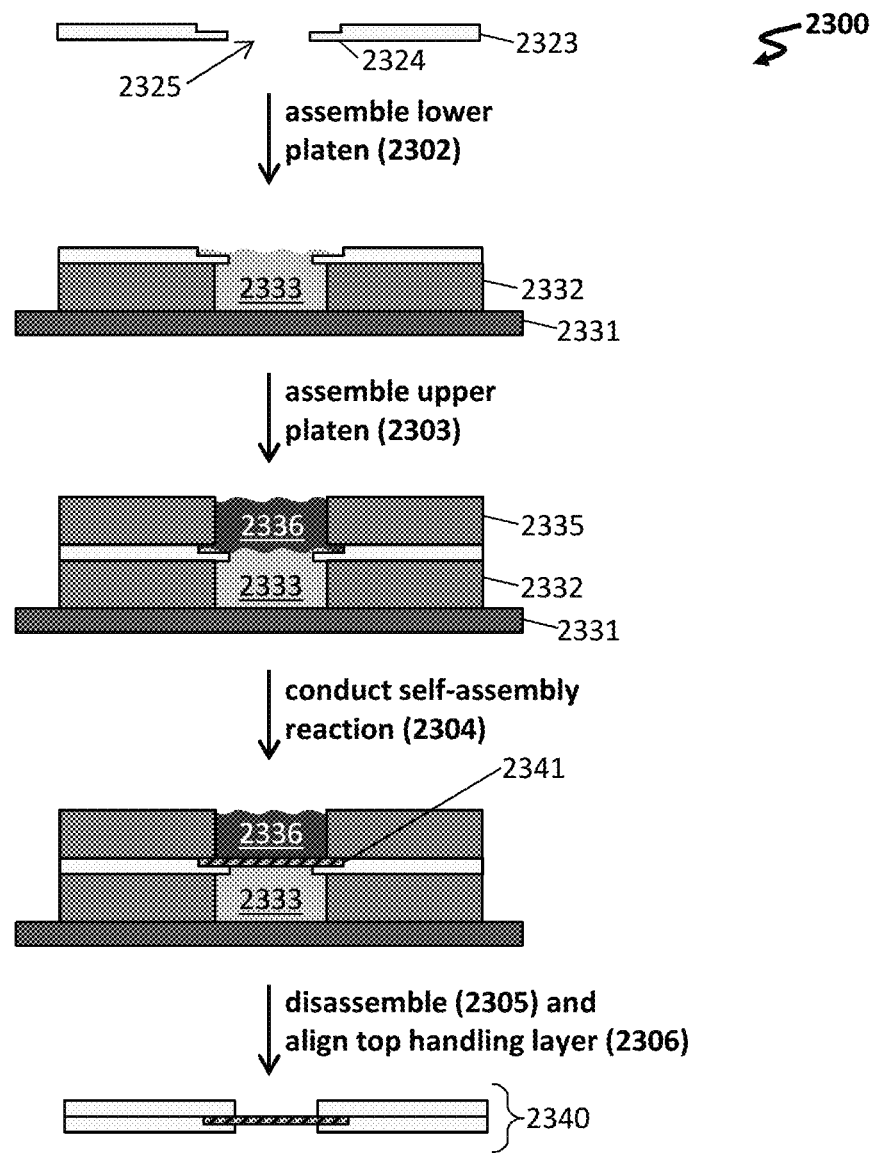

In another instance, the handling layer includes an empty aperture, and only a single handling layer is employed. FIG. 20C provides an exemplary method 2300 including assembling the lower platen 2302, assembling the upper platen 2303, conducting the self-assembly reaction 2304, and disassembling 2305 the platens to provide the insert with a self-assembled membrane. Optionally, the method can include aligning the top handling layer 2306 to form a laminated cell culture insert 2340.

The assembling steps include assembling a lower platen 2332 and associated optional substrate 2331 including the first precursor agent 2333 below the handling layer 2323, which in turn includes an aperture 2325 and an optional rim 2324; and assembling an upper platen 2335 including the second precursor agent 2336 above the handling layer 2323. Then, the self-assembly reaction is conducted 2304 at the interface of the precursor agents, thereby forming a membrane 2341 within the handling layer 2323. Finally, the apparatus is disassembled 2305 to provide a handling layer having a self-assembled membrane 2341. This handling layer can be employed directly with a modular assembly, such as any described herein. Optionally, the handling layer can be further laminated with another handling layer, such as by aligning the top handling layer 2306 to form a laminated cell culture insert 2340.

Figure 20D:
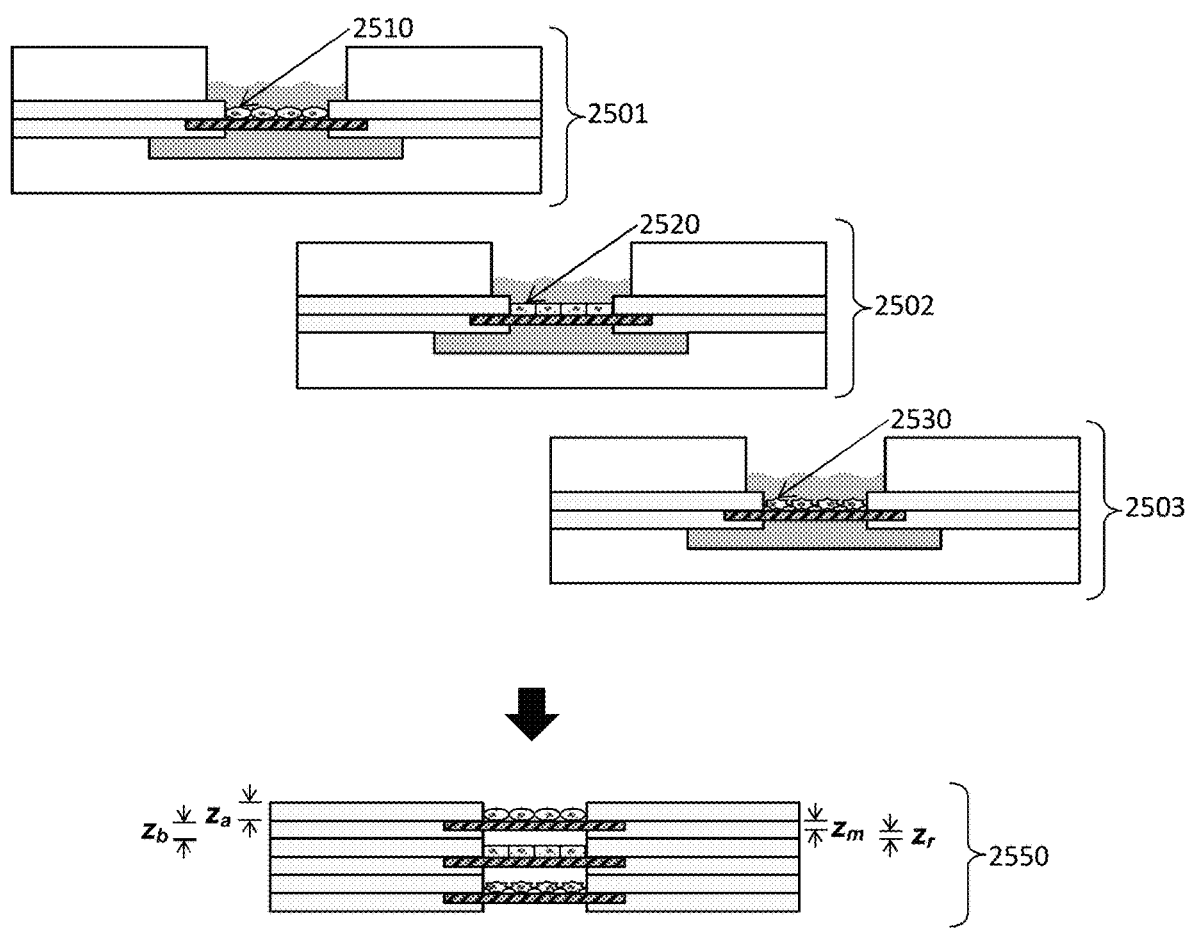

Stacks of culture insert may also be formed. For instance, individual inserts can be fabricated, e.g., using any method herein, and then each insert can be aligned to form a stacked cell culture assembly including a plurality of inserts. Alternatively, each insert can be individually seeded with any useful cell or cell population, and then each insert having cell(s) can be aligned to provide a stacked cell culture assembly. Each insert can have different cell types or the same cell type. FIG. 20D provides an exemplary method of fabricating a stacked assembly 2550. As can be seen, each insert is incubated in separate modular assemblies 2501, 2502, 2503, and each insert includes a different cell type 2510, 2520, 2530. Then, the modular assemblies are disassembled, and the inserts are aligned to form a stack 2550. Each dimension of the insert can be optimized to provide the desired cell-cell communication between the cell cultures disposed on the inserts. Exemplary dimensions include a thickness of the membrane $z_m$, a thickness of the rim $z_r$, a thickness of the top handling layer $z_a$, and a thickness of the bottom handling layer $z_b$.

Methods of Use

The present assemblies and systems can be used to conduct any assay for detecting any target of interest (e.g., any described herein). In particular embodiments, the assembly is useful for on-chip detection, such as by use of optical microscopy methods. In other embodiments, one or more analytes can be eluted off of the assembly and analyzed in an off-chip manner. Exemplary uses include any useful methodology for detection a target (e.g., any described herein), such as polymerase chain reaction amplification, cell culture techniques, etc.

Figure 9A:
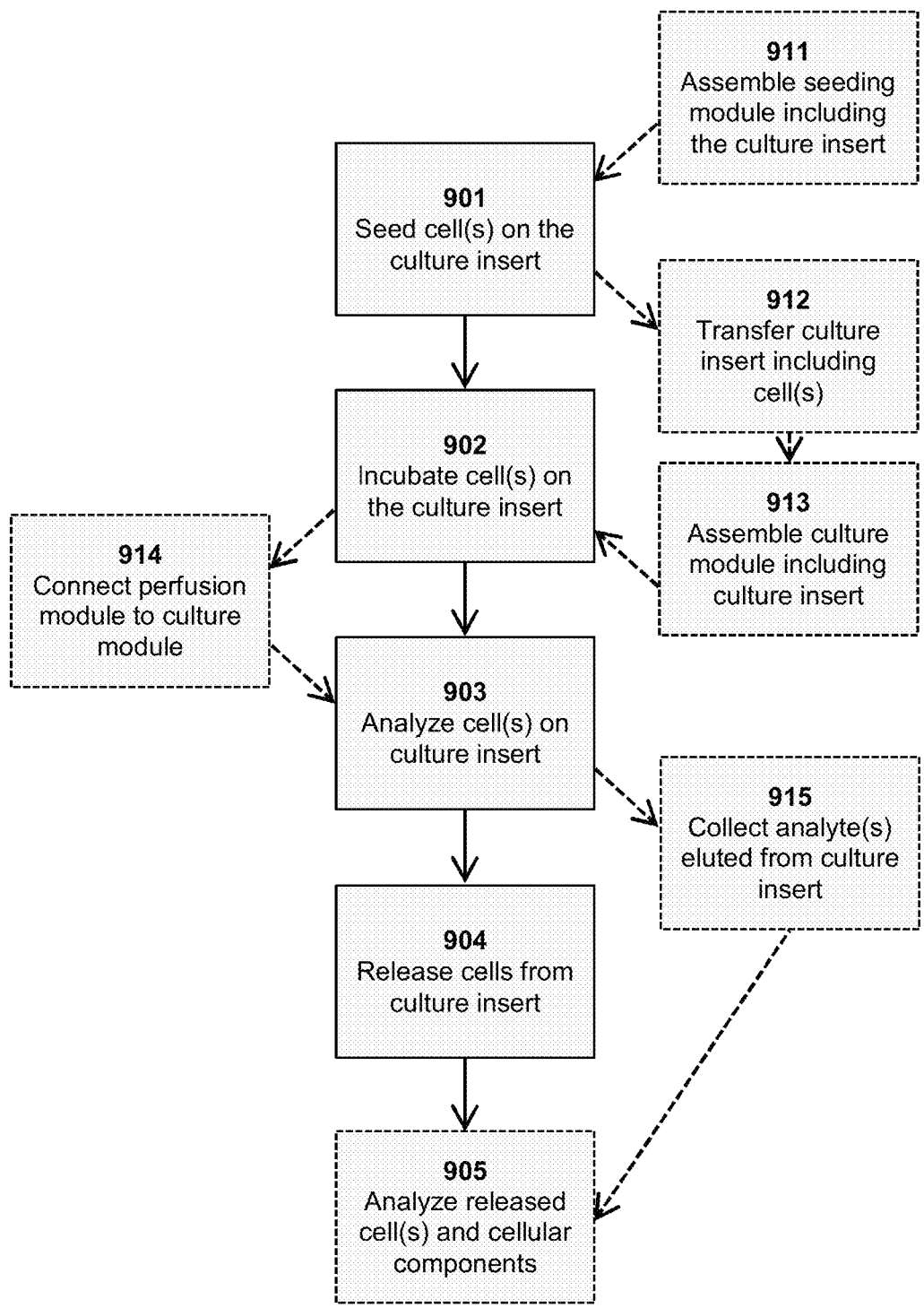
FIG. 9A-9B provides an exemplary method for using a transferrable cell culture insert to analyze cells incubated on that insert. Shown are an exemplary method with various steps (FIG. 9A) and an exemplary step 9003 to analyze cell(s) on the insert (FIG. 9B).
Figure 13A:
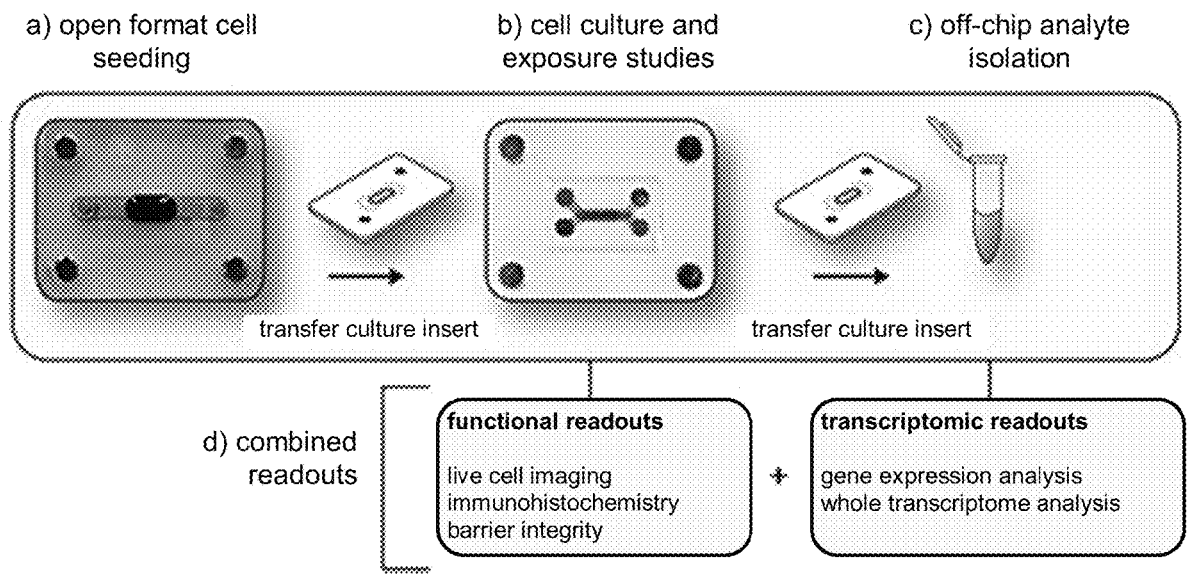
FIG. 13A-13B provides exemplary SEAM workflows.
Figure 13B:
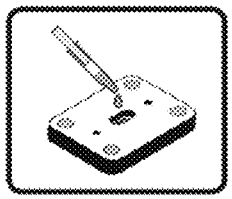
Figure 13B:
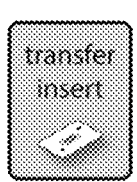
Figure 13B:
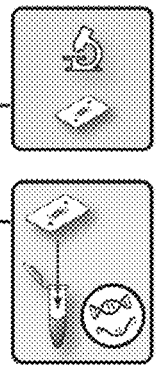
Figure 14:
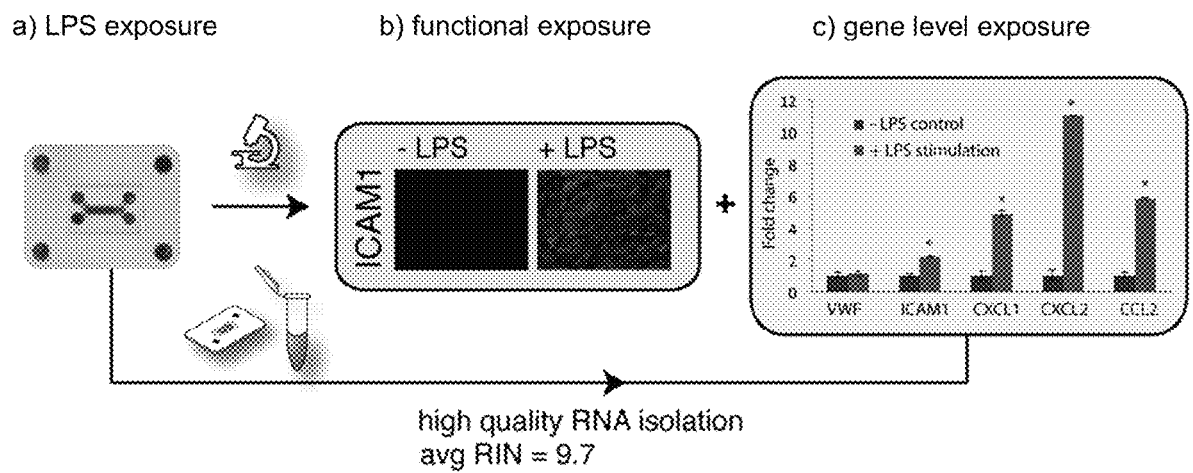
FIG. 14 provides an exemplary SEAM workflow for LPS-treatment and for combined functional and transcriptomic analysis. a) Endothelial cells are seeded using the seeding module, and the culture membrane is transferred to the culture module for controlled bacterial endotoxin lipopolysaccharide (LPS) exposure with the connected perfusion and culture modules. b) After exposure to LPS, the cells are fixed and stained in-channel to explore ICAM1 surface expression. c) Membranes with cells are removed from architecture and transferred to off-chip RNA isolation to achieve high quality RNA for gene expression analysis. Statistically significant ($p<0.001$) differences in mRNA expression were observed in ICAM1, CXCL1, CXCL2, and CCL2 with VFW (a control marker for endothelial cells) remaining constant. The SEAM assembly was able to generate both gene expression and differential surface protein responses to LPS stimulation.

FIG. 9A provides an exemplary method, including the steps of seeding 901 cell(s) on the culture insert, incubating 902 the cells, analyzing 903 the cells on the insert, and then releasing 904 the cells from the insert (e.g., by transferring the insert and rinsing with a buffer). Any additional steps can be conducted to perform this method. For instance, the method can also include optional steps of assembling 911 the seeding module including the insert to facilitate the seeding step 901; transferring 912 the insert including the cells and assembling 913 a culture module around the insert in order to incubate 902 the cells on the insert; connecting 914 a perfusion module to the culture module in order to analyze 903 the cells; collecting 915 analytes in an on-chip manner, where the analytes are eluted from the insert; and analyzing 905 released cells and cellular components in an off-chip manner. FIG. 13A-13B provides an exemplary workflow including this method of combining on-chip growth and exposure studies with off-chip readouts. FIG. 14 shows use of the workflow for controlled exposure to an endotoxin, on-chip staining, and off-chip RNA analysis. Additional details are provided herein.

Any useful analysis can be conducted. Such analysis can be conducted on cells maintained on-chip (i.e., upon the culture insert) and/or removed off-chip (i.e., removed from the culture insert). Exemplary analytical tests include any useful assay, such as bead-based assays (e.g., agglutination assays), biochemistry assays (e.g., detection one or more growth factors, signaling molecules, metabolic products, etc.), cell death assays (e.g., as determined by necrosis and/or apoptosis), diagnostic assays, fractionation assays (e.g., cell sorting assays), functional assays (e.g., motility assays, hemolysis assays, membrane deformability assays, osmotic fragility assays, ATP level assays, and hemoglobin assays), extraction assays (e.g., mRNA extraction assays), genomic assays (e.g., nucleic acid hybridization assays and nucleic acid sequencing assays, such as PCR assays, RT-PCR assays, amplification assays, and next-generation sequencing assays), hybridization assays (e.g., nucleic acid hybridization assays), immunoassays, inhibition assays, labeling assays (e.g., as determined by staining and separation), metabolic assays (e.g., as determined by precursor uptake), microscopy visualization, mobility assays (e.g., chemotaxis assays, chemoinvasion assays, cellular motility assays, or cellular migration assays), phenotype assays, proliferation assays (e.g., cell proliferation assays, DNA synthesis assays, metabolic cell proliferation assays, and intracellular ATP assays), proteomic assays (e.g., protein sequencing assays, protein expression assays, and protein crystallization assays), receptor binding assays, sandwich assays, screening assays (e.g., high-throughput screening assays or ultra-high-throughput screening assays), signaling assays (e.g., cell signaling assays), toxicity assays (e.g., cytotoxicity assays, viability assays, and proliferation assays), transfection assays, and viability assays (e.g., membrane leakage assays, mitochondrial activity assays, caspase assays, functional assays, genomic assays, and proteomic assays), which can be detected in any useful manner (e.g., fluorescence, luminescence, chemiluminescence, colorimetric, radioactive, immunohistochemical, absorbance, epifluorescence, phase, optical, and/or visual methodologies).

Figure 9B:
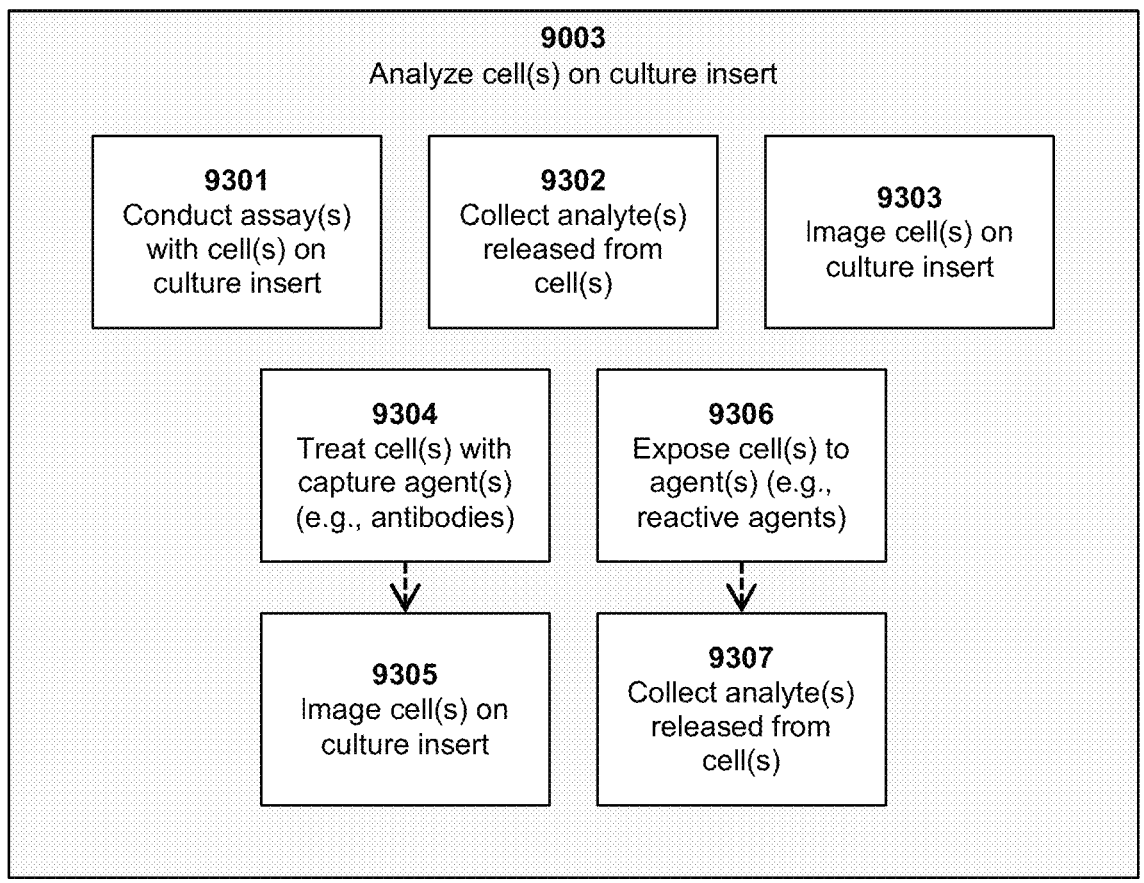

FIG. 9B provides exemplary step(s) to analyze cell(s) on an insert 9003. Such steps can include one or more of the following: conducting 9301 one or more assays with cells disposed on an insert (e.g., one or more on-chip assays), collecting 9302 one or more analytes released from cells (e.g., on-chip collection of one or more analytes released from cells), imaging 9303 one or more cells disposed on the insert (e.g., on-chip imaging by way of optical, fluorescence, epifluorescence, luminescence, or chemiluminescence methodologies), treating 9304 one or more cells with one or more capture agents (e.g., any capture agents described herein, such as one or more antibodies) with optional imaging 9305 of one or more cells disposed on the insert, and/or exposing 9306 one or more cells to one or more agents (e.g., any agent described herein, such as a reactive agent) with optional collecting 9307 of one or more analytes released from one or more cells.

Arrays

The modular assemblies and systems herein can be used to conduct numerous cell cultures and assays. In one instance, the assembly can be configured to include a plurality of transferrable inserts, in which each insert can be used to culture a different cell type or population. In another instance, each insert can include the same cell type or population, but a different assay can be conducted for each insert by injecting different agents into the access port that is in fluidic communication with each insert. In yet another embodiment, an insert can include an array of membranes disposed within a single handling layer. Thus, the present invention encompasses the use of a housing set that accommodates an array of a plurality of transferrable inserts and/or an insert having an array of a plurality of membranes. For instance, the housing set can include a top housing having a plurality of access ports configured to be in fluidic communication with the array of inserts; and a bottom housing having a plurality of recesses, where each recess is configured to accommodate one insert. One or more sealing layers can be present, which can further include one or more fluidic channels or vias to deliver one or more agents to each insert in a controlled manner.

Channels and Vias

The present assemblies can include one or more channels, which can be configured to substantially enclose a fluid or a substance in a layer of the assembly. The channel can have any useful geometry or dimension. Each channel can be interconnected to another channel (e.g., by way of a via), reservoir, or volume within the assembly to create a fluidic pathway (e.g., a fluidic pathway between one access port and another access port). Any of the channels described herein can be surface modified (e.g., to increase biocompatibility, decrease protein adsorption or absorption, and/or decrease surface contamination). Furthermore, such channels can also include one or more capture agents to selectively or non-selectively bind to cell components or contaminants within a sample.

The present assemblies can also include one or more vias, such as, e.g., inlets, outlets, fluidic opening, ports, access ports, vents, or any other structure to allow for fluidic communication between one or more channels, chambers, enclosures, etc. or between two layers within the assembly.

Fasteners

The present assemblies and systems can be reversibly attached and detached by employing one or more fasteners within the assembly (e.g., within the housing set, top housing, bottom housing, inserts, sealing layers, etc.). In one non-limiting embodiment, the top housing includes a first fastener and the bottom housing includes a second fastener, in which the first and second fasteners are configured to be reversibly attached to each other. In addition, the first fastener and the second fastener can be located within each respective housing to allow maximal alignment of the first and second fasteners. In another non-limiting embodiment, the fastener is configured to apply force to the exterior surfaces of the housing set. For instance, the fastener can be a clamp configured to secure the top and bottom housing together.

Any useful fastener(s) can be employed. Exemplary fasteners include magnetic fasteners (e.g., use of a pair of magnetic fasteners aligned to be reversibly attached to each other by attractive magnetic forces, or use of a magnetic fastener with a metal, such as a ferromagnetic metal, aligned to be reversibly attached to each other by attractive magnetic forces), adhesive fasteners (e.g., pressure sensitive adhesives), mechanical fasteners (e.g., clamps, latches, etc.), connectors, clasps, clamps, clips, closures, latches, mating members (e.g., a hook and eye, a protrusion and cavity, a hook and loop fastener, etc.), screws (e.g., spring-loaded screws), suction cups, and pegs, in which each of these may be present as fastener pairs (e.g., a first fastener and a second fastener, in which each is configured to be reversibly attached to the other fastener) and each may be present within the housing or external to the housing.

The fastener can be formed from any useful material that is responsive to an applied magnetic field, such as a magnetic material or a metal aligned in any manner (e.g., an axially magnetized material, a diametrically magnetized material, a material magnetized through the thickness of the material, an arc magnetized material, and a circumferential magnetized material). Exemplary magnetic materials include a neodymium magnet (also known as NdFeB), a samarium-cobalt magnet, a ferrite magnet, an alnico magnet, a rare earth magnet (e.g., an Nd—Pr—Ce—Fe—B alloy (e.g., MQP-12-5 isotropic powder), an Nd—Fe—B alloy, an Nd—Pr—Fe—B alloy, an Nd—Co—Fe—B alloy, an Nd—Ce—Fe—B alloy, an Nd—Pr—La—Fe—B alloy, an Nd—Nb—Fe—B alloy, a Pr—Fe—B alloy, or a Pr—Co—Fe—B alloy), a permanent magnet, a magnetic coil (e.g., a solenoid), a metallic element to attract the valve element, and an electromagnet (e.g., an integrated electromagnet configured to be activated electronically) in any useful form, including membranes, layers, particles (e.g., a thin membrane or layer including a magnetic nanocomposite material or bead, such as a rare earth magnetic powder), plated forms (e.g., including a plating having nickel, copper, epoxy, gold, silver, and/or zinc), or solids. Exemplary metals include iron, nickel, cobalt, gadolinium, neodymium, samarium, steel, magnetite, a ferrite, as well other metals, alloys, or composites thereof, and any capable of being magnetized.

The adhesive fastener can include any useful adhesive. Exemplary adhesives include a pressure sensitive adhesive (e.g., an acrylic, silicon, or acrylic-hybrid based adhesive optionally including a support layer), an acrylic adhesive, an acrylic-hybrid adhesive, a silicone adhesive, and/or an adhesion promoter (e.g., Dow Corning® 1200 primer, including light aliphatic petroleum solvent naptha, xylene, tetrapropyl orthosilicate, tetrabutyl titanate, ethylene glycol methyl ether, tetra (2-methoxyethoxy) silane, and/or ethylenebenzene).

The fasteners can be attached and detached in any useful manner. When the fastener is an adhesive fastener, such fasteners can be attached and detached by manually aligning fasteners and peeling away fasteners. When the fastener is a magnetic fastener, such fasteners can be attached and detached by increasing and decreasing the distance, respectively, between the first and second fasteners. Magnetic fasteners can also be attached and detached by applying a magnetic field (e.g., an external magnetic field source). Exemplary sources include a permanent magnet, a magnetic coil (e.g., a solenoid), a metallic element to attract the valve element, and an electromagnet (e.g., an integrated electromagnet configured to be activated electronically).

Materials

The present assemblies, and components thereof, can be formed from any useful material. Exemplary materials include a polymer, such as polymethyl methacrylate (PMMA), polyethylene terephthalate (PET, e.g., biaxially-oriented PET or bo-PET, often marketed under the tradename "Mylar™"), an acrylic polymer, poly(dimethylsiloxane) (PDMS), polycarbonate (PC), cyclo-olefin copolymer (COC), polyester, polyethylene terephthalate glycol (PETG), polyethylene (PE, such as branched homopolymer PE), polyvinylchloride (PVC), polystyrene (PS), styrene copolymer, polyimide (PI), polypropylene (PP), polytetrafluoroethylene (PTFE), polynorbornene (PN), poly (4-methyl-1-pentene), silicone, and combinations or co-polymers thereof, silicon; glass; an adhesive, such as a pressure sensitive adhesive; as well as combinations thereof (e.g., combinations of such materials provided in separate layers or within the same layer). Polymers can include any useful additive, such as, e.g., fillers (e.g., mica, talc, or calcium carbonate), plasticizers (e.g., dioctyl phthalate), heat stabilizers (e.g., organo-tin compounds), antioxidants (e.g., phenols or amines), and/or UV stabilizers (e.g., benzophenones or salicylates). Such materials can be provided in any useful form, such as in one or more layers that can be laminated to provide a housing that can be assembled around the transferrable insert.

Exemplary adhesives include an acrylate (e.g., a silicone acrylate, a polymethyl acrylate, a polymethyl methacrylate, including those formed from 2-ethyl hexyl acrylate or n-butyl acrylate monomers), a polyolefin (e.g., polyethylene, polybutene, or polypropylene), an acetate (e.g., an ethylene-vinyl acetate having a melting temperature of about 110° C.), a styrene (e.g., a polystyrene, a styrene block copolymer (e.g., styrene-butadiene-styrene, styrene-isoprene-styrene, styrene-ethylene/butylene-styrene, or styrene-ethylene/propylene), an isobutylene (e.g., polyisobutylene, a copolymer of isobutylene with isoprene, including copolymers thereof, as well as any having a melting temperature of about 100° C.), a rubber (e.g., a polyisoprene, a silicone rubber, a polychloroprene, a polyisobutylene, as well as copolymers of any of these), a polyamide, a polyester, a polyurethane, a polynitrile (e.g., nitrile butadiene rubber), a polyether (e.g., a vinyl ether), etc. The adhesive material can be provided in any useful format. For instance, the adhesive material can be provided as a substantially planar substrate.

The materials, as well as components and assemblies formed such materials, can be processed using any useful method. Exemplary methods of fabrication include rapid prototyping, microfabrication (e.g., by casting, injection molding, compression molding, embossing, ablation, thin-film deposition, and/or Computer Numerically Controlled (CNC) micromachining), photolithography, etching techniques (e.g., wet chemical etching, reactive ion etching, inductively coupled plasma deep silicon etching, laser ablation, or air abrasion techniques), methods for integrating these structures into high-throughput analysis equipment (e.g., integration with a microplate reader or a control instrument, such as a computer), methods for fabricating and integrating valves (e.g., one or more pneumatic valves), methods for integrating structures with a transducer array, methods for modifying surfaces (e.g., by including a layer of extracellular matrix components, such as fibronectin (FN), laminin, Matrigel™, albumin, and/or RGD peptide), methods for including one or more capture arrays (e.g., a capture array including one or more capture agents provided in a high-density array on a substrate), and methods for providing vias or inlets (e.g., by piercing, drilling, ablating, or laser cutting), such as those described in U.S. Pat. No. 8,257,964; and U.S. Pub. Nos. 2012/0231976, 2012/0214189, 2011/0129850, 2009/0251155, and 2009/0036324, each of which is incorporated herein by reference in its entirety.

Additional Components

The present assemblies and systems can include one or more additional components, as described herein. For instance, one or more detection components can be provided, which can allow for detection by electrochemical, colorimetric, fluorescent, western blot, immunohistochemistry, immunoassay (e.g., lateral flow assay), immunochromatography, radio immunoassay, optical immunoassay, enzyme immunoassay, chemiluminescence, and/or electrochemiluminescence methods in any useful format.

The device can include one or more separation/extraction components (e.g., filters, posts, membranes, weirs (optionally including beads), matrices, or high voltage electrodes for performing on-chip capillary electrophoresis separations); heating components (e.g., electrodes or filaments); pumps (e.g., active or passive pumps, such as a low flow rate peristaltic pump or application of negative pressure, such as by actuating a valve); a membrane (e.g., placed within a channel and/or an aperture); a multifunctional sensor (e.g., to measure temperature, strain, and electrophysiological signals, such as by using amplified sensor electrodes that incorporate silicon metal oxide semiconductor field effect transistors (MOSFETs), a feedback resistor, and a sensor electrode in any useful design, such as a filamentary serpentine design); a microscale light-emitting diode (LEDs, such as for optical characterization of the test sample); an active/passive circuit element (e.g., such as transistors, diodes, and resistors); an electrode sensor; an actuator; a wireless power coil; a device for radio frequency (RF) communications (e.g., such as high-frequency inductors, capacitors, oscillators, and antennae); a resistance-based temperature sensor; a photodetector; a photovoltaic cell; a diode; and/or a data-processing circuit powered by the power source and electrically connected to the energy source.

Agents

The present assembly can facilitate on-chip processing of any number of useful agents. Exemplary agents include a reactive agent (e.g., a stimulus, a toxin, a drug, a vaccine, a virus, a viral particle, a toxin, a protein, a peptide, a nucleic acid, an enzyme, a lipid, a polysaccharide, an immunoreactive agent, a hormone, a chemoselective agent, a cofactor, an antigen, an antibody, etc., such as lipopolysaccharide (LPS) or siRNA), a reagent (e.g., any agent herein useful for conducting an assay or another biochemical technique, such as a buffer, a salt, a detergent, a label, a cleavable substrate, a dye, a fluorophore, etc.), a detection agent (e.g., a dye, such as an electroactive detection agent, a fluorescent dye, a luminescent dye, a chemiluminescent dye, a colorimetric dye, a radioactive agent, etc.; a particle, such as a microparticle, a nanoparticle, a latex bead, a colloidal particle, a magnetic particle, a fluorescent particle, etc.), a label (e.g., an electroactive label, an electrocatalytic label, a fluorescent label, a colorimetric label, a quantum dot, a nanoparticle, a microparticle, a barcode, a radio label (e.g., an RF label or barcode), avidin, biotin, a tag, a dye, a marker, an enzyme that can optionally include one or more linking agents and/or one or more dyes), an amplifying agent (e.g., a PCR agent, such as a polymerase, one or more deoxyribonucleotide triphosphates, a divalent metal (e.g., $MgCl_2$), a template DNA, a primer), a capture agent (e.g., such as a protein that binds to or detects one or more markers (e.g., an antibody or an enzyme), a globulin protein (e.g., bovine serum albumin), a nanoparticle, a microparticle, a sandwich assay reagent, a catalyst (e.g., that reacts with one or more markers), an enzyme (e.g., that reacts with one or more markers, such as any described herein)), a cell medium (e.g., agar; nutrient media; minimal media; differential media; nutrient broth; or brain-heart infusion broth, where any of these can optionally include one or more antibiotics, one or more nutrients (e.g., a carbon source, such as glucose), one or more enzymes, one or more host cells, and/or one or more salts), a detergent (e.g., sodium dodecyl sulfate (SDS)), a surfactant (e.g., Tween 20, Triton X-100, glycerin, polyvinylalcohol (PVA), polyvinylpyrrolidone (PVP), or polyethylene glycol (PEG)), a buffer (e.g., a phosphate or borate buffer), an alcohol (e.g., from about 1% v/v to about 10% v/v methanol, ethanol, or isopropanol), a preservative (e.g., sucrose or trehalose), a blocking agent (e.g., gelatin, casein, bovine serum albumin, IgG, PVP, or PVA), a bead (e.g., a glass bead, silica bead, etc., such as to aid in mixing), etc., as well as combinations thereof.

Cell Samples and Targets

The assemblies herein can be employed to grow or culture any useful cell, including any useful cell type, population, or subpopulation. Exemplary cells include a bacterium, a fungus, a mammalian cell, a plant cell, a eukaryote, a prokaryote, etc. Exemplary cell types include endothelial cells, epithelial cells, fibroblasts, bone marrow cells, embryonic cells, hepatocytes, myocytes, neural cells, adipocytes, astrocytes, brain cells, blood cells (e.g., leukocytes, erythrocytes, platelets, neutrophils, eosinophils, basophils, lymphocytes, etc.), liver cells, heart cells, kidney cells, lung cells, stomach cells, intestine cells, pancreas cells, ovary cells, cervix cells, spleen cells, artery cells, venule cells, capillary cells, connective tissue cells, organ tissue boundary layer cells, connective tissue cells, muscle cells, bone cells, nervous tissue cells, germ cells, stem cells, healthy and diseased cells, tumor cells or tissues (e.g., primary and cultured neoplastic cells), cultures thereof, 3D tissues or cultures thereof, as well as combinations thereof.

Any useful target within a cell can be detected and/or assayed. Exemplary targets include a membrane protein (e.g., a receptor), a protein (e.g., a growth factor, an enzyme, a cytokine, or a transmitter), a nucleic acid (e.g., DNA, RNA, and/or mRNA for detecting one or more alleles, pathogens, single nucleotide polymorphisms, mutations, etc.), a metabolite (e.g., a nucleotide, an amino acid, a vitamin), etc.

EXAMPLES

Example 1: A Modular Self-Contained Organ-On-a-Chip Architecture Featuring Multi-Tiered Readouts and Advanced Biomaterial Culture Interfaces Organ-on-a-chip (OC) technologies have emerged as physiologically relevant in vitro screening tools to explore tissue and organ-level interactions with an external agent, e.g., any described herein. To help OCs reach end-users in clinical medicine and life science research, we present a modular, magnetically coupled OC architecture that provides (i) direct access to microscale culture supports for cell seeding; (ii) simplified fluidics to maintain cultures and study interactions with added stimuli; (iii) on-chip fixing, staining and visualization of tissue responses; and (iv) direct tissue access for high quality RNA isolation for pathway-level readouts. In addition, advanced biomimetic interfaces can be readily incorporated into the architecture.

OC technologies (e.g., microfluidic barrier tissues (MBTs)) are advanced culture platforms that combine microengineering techniques with living cells to address the pressing need for in vitro tissue constructs that can predict human responses to external stimuli such as drug candidates, pathogens, or toxins (see, e.g., Ghaemmaghami A M et al., *Drug Discov. Today* 2012; 17:173-81; Bhatia S N et al., *Nat. Biotechnol.* 2014; 32:760-72; and Esch M B et al., *Adv. Drug Deliv. Rev.* 2014; 69-70:158-69).

Typical OC systems are monolithic polymer structures composed of a synthetic microporous culture membrane irreversibly bonded between microfluidic channel networks. The individually addressable channels above and below the suspended culture membrane provide excellent control over the cellular scale microenvironment and enable (i) replication of physiological fluid flows and shear stresses, (ii) generation of tissue-specific biochemical cues, and (iii) development of co-cultured cell architectures. These unique capabilities have been leveraged to create highly defined biological interfaces that extend the capabilities of conventional culture models and open new avenues for exploration (see, e.g., Huh D et al., "Microengineered physiological biomimicry: organs-on-chips," *Lab Chip* 2012; 12(12): 2156-64; Kim H J et al., "Human gut-on-a-chip inhabited by microbial flora that experiences intestinal peristalsis-like motions and flow," *Lab Chip* 2012; 12(12):2165-74; Huh D et al., "From 3D cell culture to organs-on-chips," *Trends Cell. Biol.* 2011; 21(12):745-54; and Esch M B et al., "Multi-cellular 3D human primary liver cell culture elevates metabolic activity under fluidic flow," *Lab Chip* 2015; 15:2269-77).

OCs excel at providing the quantitative functional readouts (e.g., cell viability, metabolic activity, barrier permeability, and differential staining) that are critical to understanding the basic responses of a tissue to external stimuli. For example, Huh and coworkers demonstrated endothelial cell activation and white blood cell transmigration in response to bacterial and nanomaterial stimulation under cyclical stretch and physiological fluid flow using their pioneering lung-on-a-chip device (see, e.g., Huh D et al., "A human disease model of drug toxicity-induced pulmonary edema in a lung-on-a-chip microdevice," *Sci. Transl. Med.* 2012; 4(159):159ra47; and Huh D et al., "Reconstituting organ-level lung functions on a chip," *Science* 2010; 328 (5986):1662-8). Although highly informative, functional responses only represent one dimension of the complex, multi-factorial interaction between an external agent and a tissue. The combination of functional responses with subtle pathway-level readouts can shed light on the complex activities that drive tissue responses.

With the mapping of the human genome and advancements in bioinformatics, transcriptomic analysis has emerged as a powerful approach to explore the activities that occur upstream of protein expression (see, e.g., Licatalosi D D et al., "RNA processing and its regulation: global insights into biological networks," *Nat. Rev. Genet.* 2010; 11(1):75-

87). For example, transcriptomic readouts can identify whether a drug candidate can engage targeted signaling pathways with specificity, or guide the development of a medical countermeasure by mechanistically exploring host-pathogen interactions (see, e.g., Verbist B et al., "Using transcriptomics to guide lead optimization in drug discovery projects: Lessons learned from the QSTAR project," *Drug Discov. Today* 2015; 20(5):505-13).

Although nucleic acid isolation protocols are well established within conventional lab-on-a-chip platforms (Van Heirstraeten L et al., "Integrated DNA and RNA extraction and purification on an automated microfluidic cassette from bacterial and viral pathogens causing community-acquired lower respiratory tract infections," *Lab Chip* 2014; 14(9): 1519-26; and Berry S M et al., "Streamlining gene expression analysis: integration of co-culture and mRNA purification," *Integr. Biol.* (Camb.) 2014; 6(2):224-31), the robust RNA isolation required for transcriptomic analysis can be difficult to achieve with current monolithic organ-on-a-chip platforms. The challenge likely stems from the inevitable sample losses that occur along the fluidic pathway during lysate collection from sample dilution, dead volumes, and transport along high surface area to volume ratio channels in sealed multi-compartment systems (see, e.g., Nan L et al., "Emerging microfluidic devices for cell lysis: a review," *Lab Chip* 2014; 14(6):1060-73).

In addition, permanently sealed architectures also have difficulty incorporating alternative, biologically inspired culture interfaces due to challenges related to the formation of robust seals between polymer microfluidic channels and hydrated biomaterials (see, e.g., Duffy D C et al., "Rapid prototyping of microfluidic systems in poly(dimethylsiloxane)," *Anal. Chem.* 1998; 70(23):4974-84). In particular, processes associated with effective cell seeding, culture maintenance, and access to cells for downstream analysis can be challenging. The aim of the work presented here is to introduce a new approach that incorporates specialized pre-fabricated microfluidic modules to help streamline and simplify experimental workflows. Advancements in organ-on-a-chip technologies that integrate functional responses, transcriptomic readouts, and tailored biomaterial culture interfaces would help improve insight into tissue-level interactions and enhance the predictive power of in vitro assays.

Toward this end, we present a scalable, easy-access, modular (SEAM) OC architecture. SEAM features a reversibly sealed magnetic latching mechanism that combines the advantages found in open access cell cultures with the microenvironment control found in microfluidic culture systems. The self-contained, easy-to-use, modular architecture offers unique capabilities in (i) cell seeding, (ii) high quality RNA isolation, (iii) multi-tiered experimental readouts, (iv) simplified equipment-free micro-perfusion, and (v) compatibility with advanced biomaterial culture interfaces.

As proof of concept, we employed the self-contained SEAM platform to demonstrate both functional cellular-level responses and gene expression readouts from primary human microvascular endothelial (HMVEC) cells after stimulation with the bacterial endotoxin lipopolysaccharide (LPS). We also demonstrate the inclusion of ultra-thin, self-assembled suspended biological culture membranes with tissue-specific Young's modulus, and demonstrate multi-tiered readouts from cultured primary rat cortical cells. We anticipate that the combination of functional and pathway-level readouts from physiologically relevant culture platform will help establish a unique set of metrics to help assess the potential safety and efficacy of drug candidates and better understand toxin and pathogen interactions with the human body.

To expand the capabilities of organ-on-a-chip assays and provide economical user-friendly operation, we have established a self-contained platform that consists of a removable cell culture insert and three distinct modules for microfluidic operations: direct cell seeding, cell culture, and micro-perfusion. The reversibly sealed modules allow the culture insert to be rapidly coupled, decoupled and transferred between modules to achieve a precise and efficient experimental workflow. The modular approach provides unique advantages in (i) cell seeding, (ii) efficient cell isolation, (iii) generation of multi-tiered readouts, (iv) inclusion of tailored biological interfaces, and (v) simplified user-friendly operation.

In addition, the exemplary assembly includes magnetic latching. This magnetic latching approach enabled reversibly sealed modules and also provides a simple approach to connect different tissue modules together (e.g., heart to lung) through a magnetic manifold to explore multi-module drug or toxin interactions. Experimental scale up can be achieved by connecting multiple modules to a common perfusion source. The modular approach described here also enables in-line microfluidic immunoassays to be integrated with SEAM to analyze secreted proteins from small cell populations (see, e.g., Lin C C et al., "Microfluidic immunoassays," *J. Assoc. Lab. Automat.* 2010; 15:253-74; Herr A E et al., "Microfluidic immunoassays as rapid saliva-based clinical diagnostics," *Proc. Nat'l Acad. Sci. USA* 2007; 104(13): 5268-73; and Hatch A V et al., "Integrated preconcentration SDS-PAGE of proteins in microchips using photopatterned cross-linked polyacrylamide gels," *Anal. Chem.* 2006; 78(14):4976-84), and the layer-by-layer fabrication technique can support electrode integration to provide barrier integrity measurements in real time. Accordingly, the reversible SEAM architecture provides a technique to explore multi-tiered readouts from cells cultured on a variety of substrates to help better understand how a tissue responds to an external agent. Additional details are provided in the following Examples.

Example 2: Culture Module

As an alternative to monolithic organ-on-a-chip constructs, we developed the reversibly sealed SEAM architecture. As shown in FIG. 10A, the culture module was constructed from (i) laser cut PMMA housing layers (PMMA thickness of about 1.5875 mm, McMaster Carr, VersaLaser 40 W $CO_2$ laser, Universal Laser Systems, Inc., Scottsdale, Ariz.) with embedded rare earth magnets (K&J Magnetics, Inc., Pipersville, Pa.), (ii) molded PDMS microchannels, and (iii) a removable culture insert.

Rigid plastic housing layers were constructed by laminating two laser cut pieces of PMMA (base layer: 18 mm×22 mm, and cavity: 18 mm×22 mm with 7 mm×11 mm cutout) using pressure sensitive adhesive sheets (Fralock). Each housing layer contained rare earth magnets (2.54 mm diameter) oriented such that the top and bottom housings had opposite magnetic poles facing one another. The cavities were designed to accept the PDMS containing channels as described below.

PDMS channel features (height of about 0.25 mm, width of about 1 mm, length of about 9 mm) were fabricated using standard soft-lithography replica molding techniques (see, e.g., Beebe D J et al., "Microfluidic tectonics: a comprehensive construction platform for microfluidic systems,"

*Proc. Nat'l Acad. Sci. USA* 2000; 97(25):13488-93). Briefly, UV reactive photoresist SU-8 100 (MicroChem) was spin coated onto a silicon wafer, soft-baked, and then exposed to UV light through a high-density transparency mask (Fineline Imaging, Inc.) to define channel features. The wafer was then immersed in developer solution (MicroChem) to remove non-crosslinked SU-8 and hard baked to establish a "master" used to create microfluidic channels.

To achieve PDMS blocks of defined total height, the master was placed into a mold cavity composed of a PMMA ring (outer diameter=250 mm, inner diameter=200 mm) attached to a PMMA disk (diameter=300 mm) using pressure sensitive adhesive (Fralock). The mold cavity was then filled with degassed PDMS prepolymer (10:1 base to catalyst ratio). A Mylar transparency sheet was placed on top of the filled mold to create a flat upper surface and covered with an additional PMMA ring (diameter=300 mm). The assembled mold was clamped and placed in an oven for 6 hours at 65° C. The resulting PDMS block (with total height of 1.7 mm) was removed from the mold and cut to size (7 mm×11 mm) with a razor blade. Access ports were cored using a 1 mm biopsy punch (Miltex). PDMS blocks were inserted into the upper and lower PMMA housings with the channel features oriented toward the interior of the device. The attraction forces between the magnets in each housing layer sealed the PDMS channels against the culture insert and established a liquid-tight seal capable of withstanding 70 kPa of applied pressure.

As shown in FIG. 10A, magnetic latching allows culture membranes to be sandwiched in between fluidic channels and sealed in place to support compartmentalized (apical/basolateral) cultures. We demonstrated the use of two cell culture materials, i) a standard track etched micro-porous culture membrane and ii) a hydrated, self-assembled culture membrane to highlight the flexibility of the magnetic sealing approach (see FIG. 10B). The hydrated, suspended membrane represents a material that is difficult to incorporate into MBT models due to aforementioned bonding incompatibilities. A polyester track-etched culture membrane (0.4 μm pore diameter, Sterlitech) was laser cut, sandwiched, and laminated between two laser cut polyethylene (PE) sheets containing an open central region and pressure sensitive silicone adhesive on one face (Fralock). The non-porous PE isolated the fluidic compartments and ensured that communication between the channels only occurred through the nanoporous culture membrane. The PE sheets also allowed the culture insert to be easily transferred between specialized modules.

As shown in FIG. 10B, the culture insert can include non-porous regions to maintain distinct fluidic compartments while providing a defined central region for cell culture. A polyester track-etched culture membrane (0.005 mm pore diameter, Sterlitech Corp., Kent, Wash.) was laser cut, sandwiched, and laminated between two laser cut polyethylene (PE) sheets that contained pressure sensitive adhesive on one face (Fralock Corp., Valencia, Calif.). The non-porous PE isolated the fluidic compartments and ensured that communication between the channels only occurred through the microporous culture membrane.

For the culture insert that included a hydrated material, PE sheets and porous membranes (0.1 μm, Sterlitech) were laser cut to create open central regions. A nanoporous track etched membrane was arranged so that a small edge extended into the open region. We adapted a liquid-liquid supramolecular self-assembly chemistry pioneered by Stupp et al. to establish a water permeable culture membrane that tethered to the carrier insert (see, e.g., Hartgerink J D et al., "Self-assembly and mineralization of peptide-amphiphile nanofibers," *Science* 2001; 294:1684-8; Hartgerink J D et al., "Peptide-amphiphile nanofibers: a versatile scaffold for the preparation of self-assembling materials," *Proc. Nat'l Acad. Sci. USA* 2002; 99:5133-8; and Beniash E et al., "Self-assembling peptide amphiphile nanofiber matrices for cell entrapment," *Acta Biomater.* 2005; 1:387-97). A PDMS reservoir was filled with a 2% w/v solution of hyaluronic acid (HA) in acetate buffer (pH 5.7, 50 mM), and a culture insert was positioned on top. A second PDMS reservoir was placed over the insert and filled with a 3% w/v solution of peptide amphiphile (PA) in acetate buffer (pH 5.7, 50 mM). The structure of PA contained a palmitic acid tail, beta sheet forming sequence, and a charged head group ($C_{16}V_3A_3K_3$). HA is a large molecular weight negatively charged linear polymer that is abundant in mammalian extracellular matrix. When the solutions came into contact with one another, a solid membrane instantaneously formed at the liquid-liquid interface through a self-assembly process driven by hydrophobic collapse of the palmitic acid tails and charge screening between the positively charged PA heads and negatively charged HA. Membrane thickness could be tuned based on liquid-liquid contact time (see, e.g., Capito R M et al., "Self-assembly of large and small molecules into hierarchically ordered sacs and membranes," *Science* 2008; 319: 1812-6; and Carvajal D et al., "Physical properties of hierarchically ordered self-assembled planar and spherical membranes," *Soft Matter* 2010; 6:1816-23).

After self-assembly, membranes were gently washed in PBS (10 mM sodium phosphate, 150 mM sodium chloride, pH 7.4). Membranes were then mounted onto a cleaned glass coverslip in a fluid cell filled with PBS. The Young's modulus for the membrane was extracted from a plot of cantilever deflection versus displacement by fitting data to a spherical Hertz contact equation using a pre-calibrated AFM cantilever modified with 0.005 mm spherical probe as described by Soofi S S et al., "The elastic modulus of Matrigel as determined by atomic force microscopy," *J. Struct. Biol.* 2009; 167: 216-9. Thickness of the membrane was determined by AFM in contact mode using a silicon nitride probe with tip dimension of 27±nm and 800 nm height (Novoscan). Data were exported in NanoScope Analysis (Bruker) for analysis in Origin Pro (Origin Labs). The molecular weight cutoff of the membrane was determined by measuring the transport of fluorescently labeled dextrans purchased from Sigma (10 kDa, 40 kDa, 70 kDa, 120 kDa, 150 kDa) across the membrane in 24 hours.

The attraction forces between the magnets in each housing layer sealed the PDMS channels against the culture insert and established a liquid-tight seal capable of withstanding about 35 kPa of applied pressure. The assembled SEAM culture platform is shown in FIG. 10C with a top channel and a bottom channel, each being a distinct compartment. Each channel could be separately perfused with cell medium to maintain the culture or employed to introduce an experimental test compound (e.g., drug, virus, or environmental toxin). The magnetic latching mechanism enabled the carrier insert (and attached cells) to be introduced and removed from SEAM modules and handled independently from the fluidic network.

Example 3: Seeding Module

In permanently sealed monolithic organ-on-a-chip systems, cells are introduced to the interior of the device by flowing a cell suspension through the microfluidic channels that are in contact with the culture membrane. Then, the flow is stopped, and cells settle onto the membrane surface. The sedimentation process along the entire channel length makes it difficult to control initial cell density and reproducibly introduce the same number of cells to the system. Special care must also be taken to prevent the introduction of bubbles during the cell introduction process. Cell seeding is significantly easier in conventional open format culture platforms, such as Petri dishes and multi-well plates, where cells are directly added to the culture surface with a pipette.

Here, the seeding module uses an open seeding approach. As an example, primary HMVEC cells were seeded and cultured on-chip using the seeding module. The simplicity of the open seeding approach is replicated here by sandwiching the culture insert in the seeding module and adding a defined number of cells directly to the cell culture region through the open reservoir. Direct seeding can significantly reduce the number of cells that are needed per experiment and enable enabling the use of rare or expensive cell populations including stem cells, primary human cells, and clinically relevant samples.

Figure 11A:
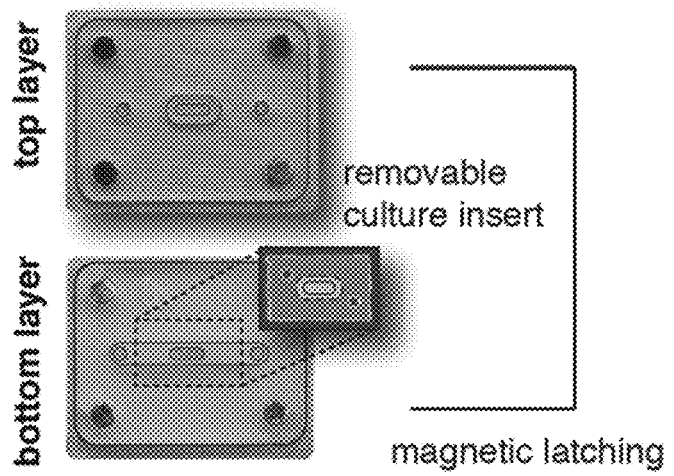
FIG. 11A-11E provides exemplary seeding modules for use in the SEAM assembly.

As shown in FIG. 11A, magnetic latching enabled the carrier insert to be coupled with a seeding module, in which cells were directly introduced to the culture region (surface area is about 0.05 cm$^2$). The fabrication process used the laser cutting and lamination processes described for the culture module.

The fabrication process utilized the laser cutting and lamination processes described for the culture module. The direct seeding module included a top PMMA housing with embedded magnets, access ports, and a central reservoir. A laser cut PDMS sheet (0.125 mm, Interstate Specialty Products, Inc., Sutton, Mass.) was attached to the bottom with pressure sensitive adhesive (0.050 mm, Fralock Corp., Valencia, Calif.) to promote leak-free seal formation around the culture insert during magnetic compression. The bottom PMMA housing contained magnets, a fluidic channel, and a laser cut PDMS sheet defining fluidic access ports.

Figure 11B:
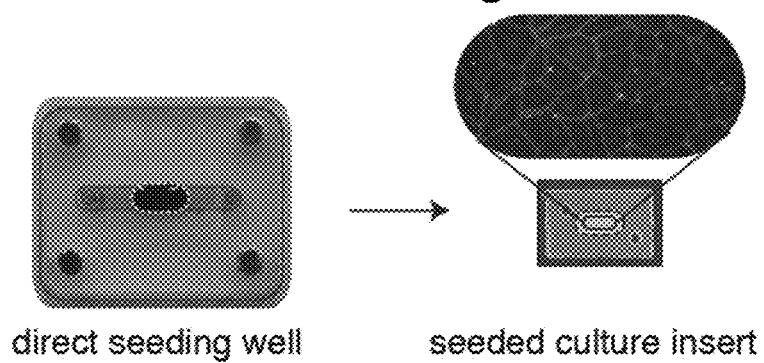

The culture membrane was aligned onto the bottom layer over the central access port, and the housings were magnetically connected (FIG. 11B). The top reservoir was then loaded with fibronectin (5 μg mL$^{-1}$) and incubated (37° C. at 5% $CO_2$) overnight to coat the membrane.

Figure 11C:
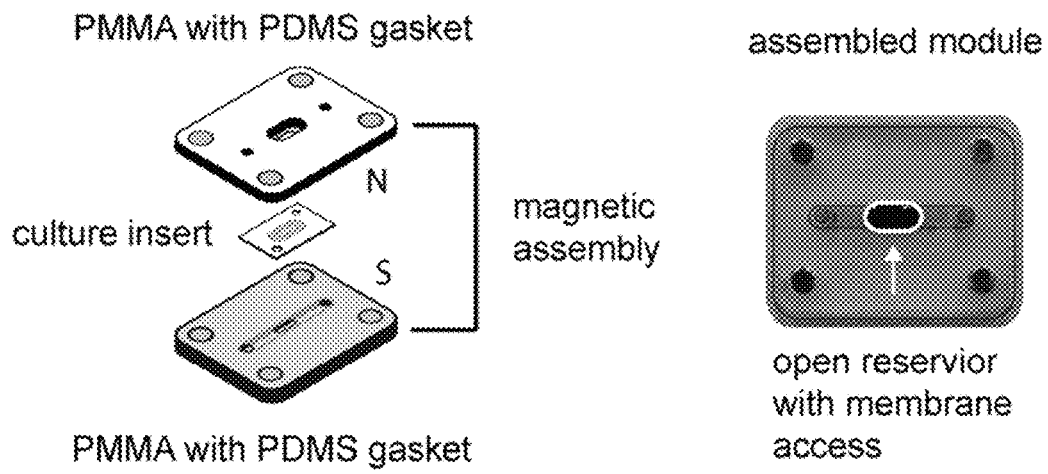
Figure 11D:
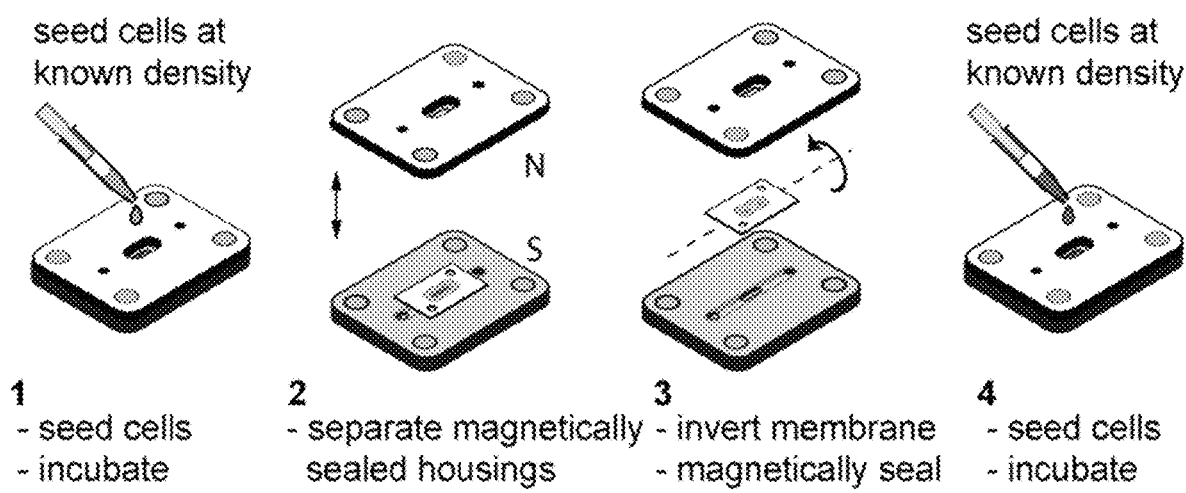
Figure 11E:
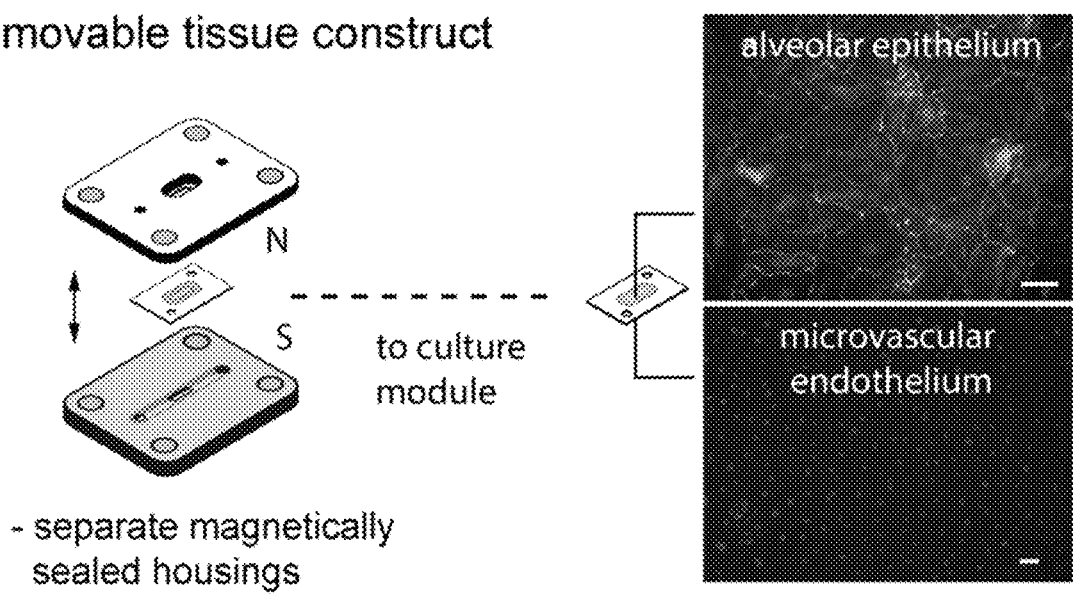

The bottom channel and top reservoir were filled with culture medium to support cell attachment, and the desired number of cells was added directly over the culture region of the carrier insert. In one instance, the reservoir and channel were then emptied via pipette and washed with PBS (10 mM sodium phosphate, 150 mM sodium chloride, pH 7.4). Then, the coated seeding module was filled with appropriate culture medium (ScienCell Research Laboratories, Carlsbad, Calif.) to support cell attachment. The seeding module was incubated for 4-6 hours until cells adhered to the culture membrane. For co-cultures, the magnetically latched PMMA housings were separated and the membrane was flipped and resealed between the housings. The bottom channel was filled with appropriate culture medium to support the attached cell population, and the exposed side of the membrane was then seeded with the second cell population. After cell adhesion, the insert (with attached cells) could then be transferred to the culture module. FIG. 11C-11E shows another embodiment of a direct seeding module.

Primary HMVEC (ScienCell Research Laboratories,) were thawed according to manufacturer's instructions and plated onto fibronectin-coated tissue culture plates. After one subculture, cells were trypsinized and resuspended at a concentration of 500,000 cells mL$^{-1}$. Two μL of the suspension was added to each open well (~1,000 cells input) of the seeding platform directly over the culture region of the sandwiched carrier insert. The cells were visualized with an inverted microscope (Olympus IX-70) to ensure uniform coverage of the membrane. The seeding module was incubated for 4-6 hours until cells adhered to the culture membrane. The insert (with attached cells) was then transferred to the culture module for micro-perfusion culture and stimulation with a test compound.

The seeding module herein minimized sample usage, as well as propagated viable human endothelial cells and rat neuronal cells. For example, a conventional organ-on-a-chip is seeded with ~20,000 primary human cells on one side of the membrane (see, e.g., Huh D et al., "Microfabrication of human organs-on-chips," Nat. Protoc. 2013; 8(11):2135-57). For a commercial primary human cell cost of ~$600 per million cells, and assuming 100% of cells are delivered uniformly to the culture region without sample loss, the conservative cell-related cost is $12/assay. In contrast, with the direct seeding technique described herein, ~1,000 cells can be introduced to a defined culture region with minimal sample loss since fluidic manipulation is not required. The corresponding cell-related cost is decreased to $0.60/assay (20× reduction), thus facilitating experimental scale up and improving practical utility. In addition, because the cell culture area and input cell numbers are both known, surface seeding densities can be rapidly optimized to fit the needs of a particular tissue.

In addition, the seeding module can be readily adapted for any useful cell type, as well as any useful culture. For instance, the seeding module allows co-cultures to be established by (i) seeding one side of the culture region, (ii) waiting for attachment, and (iii) decoupling, flipping, and resealing the insert before directly seeding the other side. After a second phase of cell attachment, the membrane can be transferred directly to the culture module.

Example 4: Perfusion Module

Figure 12A:
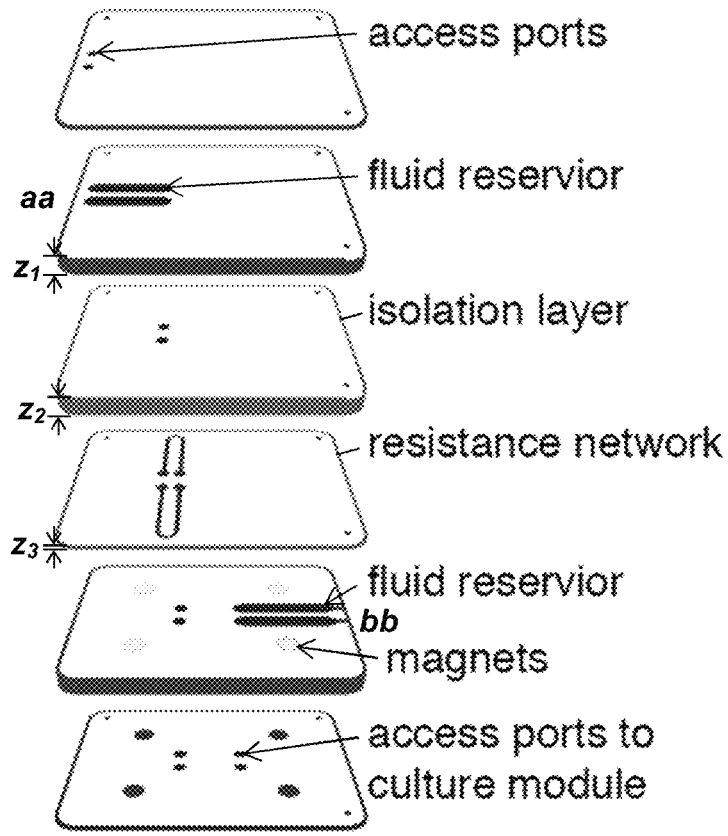
FIG. 12A-12D provides an exemplary perfusion module for use in the SEAM assembly. Shown are a schematic representation of the components of a laminated, gravity-fed perfusion module with magnetic connection to culture module (FIG. 12A); a schematic cross-sectional view of the perfusion module connected to the culture module (FIG. 12B); a schematic cross-sectional view of gravity-fed perfusion (FIG. 12C); and an image of a top view of the perfusion module connected to the culture module (FIG. 12D).

Conventional OC platforms rely on syringe pumps to drive fluid flow to maintain culture health and deliver experimental test compounds. Systems relying on syringe pumps are difficult to scale into highly multiplexed, low-cost, user-friendly research platforms. To address these concerns, we developed a multi-layer, gravity fed micro-perfusion module that was coupled to the culture module via magnetic latching (see FIG. 12A).

The micro-perfusion module was fabricated using the combination of PMMA laser machining, pressure sensitive adhesive, and lamination described previously. The layers include horizontally oriented top and bottom fluid reservoirs (PMMA thickness of about 3 mm, including about 2.5 mm), a fluidic isolation layer that defined the separation distance between reservoirs (height of about 1 mm), a fluidic resistance network (height of about 0.02 mm, width of channels of about 0.5 mm, and length of channels of about 25 mm) to control perfusion rate, and access ports to connect the modules and complete the fluidic circuit.

To provide a user-friendly option for fluid perfusion to support simple cell growth, we used a gravity-based perfusion module comprised of horizontally oriented liquid-filled reservoirs separated by a defined height. In typical gravity based approaches with vertically oriented reservoirs, the difference in liquid height between free liquid surfaces produces a hydrostatic pressure drop, $\Delta P = \rho g \Delta z$, that is reduced as the difference, $\Delta z$, between the liquid levels approaches zero.

Figure 12B:
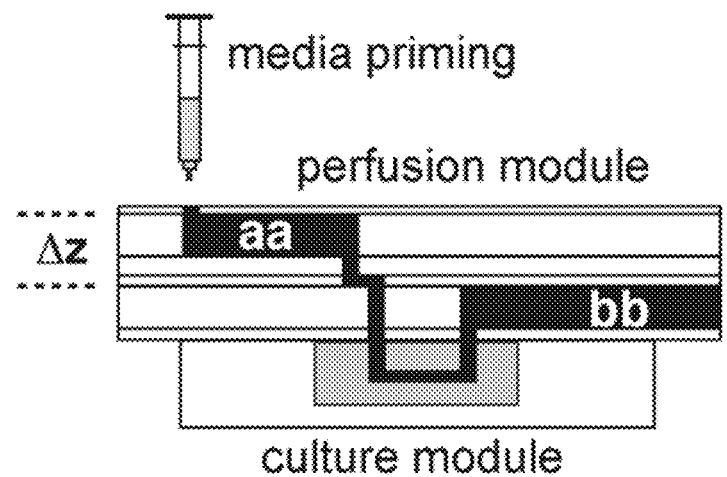

As shown in the top panel of FIG. 12B, the difference in hydrostatic pressure $\Delta P = \rho g \Delta z_{aa-bb}$. (Eq. 1) drives fluid from the higher reservoir (aa) to the lower reservoir (bb) through the magnetically coupled culture module, where $\rho$ is fluid density, g is gravity acceleration, and $\Delta z_{aa-bb}$ is the height difference between reservoir aa and reservoir bb. In contrast to vertically oriented reservoirs in which $\Delta P$ decreases as liquid levels drop over time, horizontally oriented fluid reservoirs ensure that fluid level and hydraulic pressure drop across a connected microfluidic channel network because $\Delta z$ remains constant (see, e.g., Zhu X et al., "Arrays of horizontally-oriented mini-reservoirs generate steady microfluidic flows for continuous perfusion cell culture and gradient generation," *Analyst* 2004; 129(11):1026-31). In this manner, horizontally oriented reservoirs (along the x-y plane in FIG. 1A) can be used to control fluid flow through the culture module.

As shown in FIG. 12B, the connected perfusion and culture modules were magnetically coupled and gently primed with media until the channels were filled and an air-liquid meniscus was established in each reservoir. The surface tension between the medium and the reservoir surfaces was sufficient that the liquid did not spill out in the horizontal configuration and the difference in hydrostatic pressure ($\Delta P_{aa-bb} = \rho g \Delta z$) between the inlet and outlet reservoirs induced flow from aa to bb. The meniscus moved horizontally as the liquid flowed through the circuit; since there was no change in the relative heights of the liquid within the reservoirs ($\Delta z$), and gravitational acceleration and liquid density were constant, $\Delta P$ was also constant. Flow contributions related to capillary pressure were assumed to balance because the inlet and out reservoirs were constructed from the same materials and had the same internal dimensions.

Figure 12C:
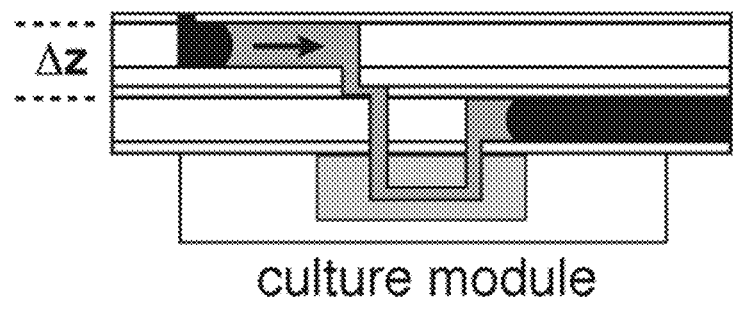

The fluidic resistance network layer was used to control the perfusion rate. In this embodiment, the purpose of the perfusion module was to provide simple micro-perfusion to support cell growth and experimental simulation without the need for syringe pumps or external instrumentation. Flow rate Q through the fluidic system can be determined as follows: $Q = \Delta P/R$ (Eq. 2), where $\Delta P$ is pressure difference and R is fluidic resistance. Once filled, surface tension kept the medium from spilling out of the reservoirs (FIG. 12C).

Whereas pressure drop $\Delta P$ can be determined by Eq. 1, fluidic resistance R is determined by the cross-sectional area of the fluidic channel. For a channel having a rectangular cross-section with a low aspect ratio, fluidic resistance R can be determined as follows:

$$R = \frac{12\mu L}{wh^3}\left[1 - \frac{h}{w}\left(\frac{192}{\pi^5}\sum_{n=1,3,5}^{\infty}\frac{1}{n^5}\tanh\left(\frac{n\pi w}{2h}\right)\right)\right]^{-1} \text{ (Eq. 3), e.g., when } w \sim h)$$

or $$R = \frac{12\mu L}{wh^3}\left[1 - \frac{192h}{\pi^5 w}\tanh\left(\frac{\pi w}{2h}\right)\right]^{-1} \text{ (Eq. 4, e.g., when } w/h < 1, Re < 1000),$$

where $\mu$ is fluid viscosity, L is channel length, w is channel width, h is channel height, and Re is the Reynolds number (Re=$\rho$UL/$\mu$, where $\rho$ is fluid density, U is linear fluid velocity, L is a characteristic length, and $\mu$ is fluid viscosity) (see, e.g., Beebe D J et al., "Physics and applications of microfluidics in biology," *Annu. Rev. Biomed. Eng.* 2002; 4:261-86 and Fuerstman M J et al., "The pressure drop along rectangular microchannels containing bubbles," *Lab Chip* 2007; 7:1479-89).

The average flow rate in the network $Q_{avg}$ was calculated from the expression $Q_{avg} = \Delta P R^{-1}$ with $\mu$=0.0007 [Pa sec] at 37° C., and w, h, L referring to the width, height and length of each segment in the fluidic path respectively. Table 1 shows the relationship between $\Delta z$ and the calculated average flow rate in the culture channel. The flow rate in our system (with $\Delta z$=3.62 mm) was calculated to be 2.42 µL hr$^{-1}$, corresponding to 58 µL used per day (one full medium exchange in the culture channel per hour). New perfusion modules were used at the end of each culture period.

TABLE 1

Differential height vs. predicted flow rate and shear stress

| | Differential height $\Delta z$ [mm] | | | | |
|---|---|---|---|---|---|
| | 1 | 3.6 | 5 | 10 | 20 |
| $Q_{avg}$ [µL hr.$^{-1}$] | 1.36 | 2.42 | 3.34 | 6.68 | 13.6 |
| $\tau$ [dyne cm.$^{-2}$] | 0.00013 | 0.0045 | 0.0006 | 0.0013 | 0.0026 |

Figure 12D:
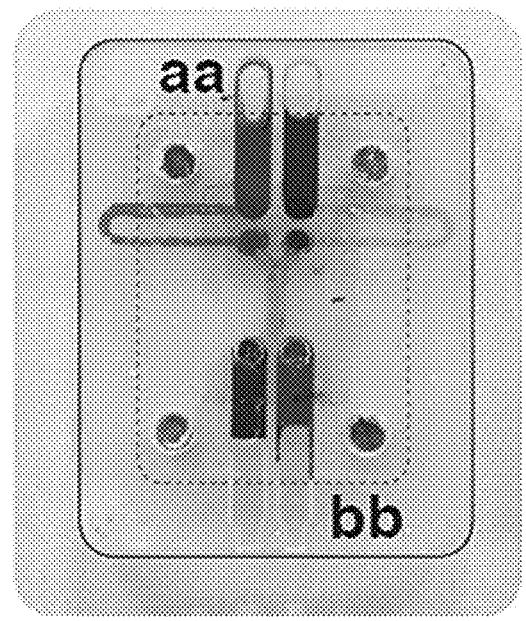

FIG. 12D shows an exemplary perfusion module. In some instances, using Eqs. 1-4, we determined an average flow rate $Q_{avg}$~300 nL hr$^{-1}$. This average flow rate was sufficient for a 50 µL culture media volume loaded in reservoir aa to perfuse the culture for a three day period. If desired, several parameters including the reservoir volume, $\Delta z$, and resistance channel dimensions (height, width, and length) can be adjusted to achieve desired perfusion rates.

The corresponding shear stress T in the culture channel was calculated to be 0.00045 dyne cm$^{-2}$ using the expression in Eq. 5 with $\gamma$ (aspect ratio of culture channel)=0.25:

$$\tau = \frac{6\mu Q}{wh^2}\begin{Bmatrix} 2.95 & \gamma < 0.25 \\ 1.158 + (1-\gamma)^{-2} & 0.25 \leq \gamma \leq 0.85 \end{Bmatrix} \text{ (Eq. 5, e.g., when } \gamma < 0.8),$$

where $\mu$ is fluid viscosity, Q is flow rate, w is channel width, h is channel height, and $\gamma$ is aspect ratio (see, e.g., Gaver D P, "A theoretical model study of the influence of fluid stresses on a cell adhering to a microchannel wall," *Biophys. J.* 1998; 75:721-33). Shear controlled environments can be beneficial in culture maintenance applications using shear-sensitive cells such as neurons and stem cell populations [29]. Calculated shear stress results are tabulated in Table 1. For studies where larger shear stress values are required, increasing the pressure head (i.e., 15.875 mm or ⅝"), removing the resistance network, and reducing the culture channel width to 0.40 mm and height to 0.1 mm enables theoretical shear stresses on the order of 10 dyne cm$^{-2}$ to be achieved.

In the embodiment shown here, the purpose of the perfusion module was to demonstrate an optional stand-alone option capable of maintaining primary human cells in culture without the need for instrument-driven pumping techniques. However, the modular nature of the SEAM platform allows conventional pumping methods, including syringe pumps, to be implemented if desired.

In an effort to make OC assays accessible to a broad range of end users, we developed a gravity fed module that provides perfusion capabilities within a self-contained system. The micro-perfusion module can be used to maintain cell cultures or expose the population to experimental compounds under flow. Each reservoir (and corresponding apical or basal channels) was individually addressable and can be used to establish physiological culture environments such as air-liquid interface culture, which is relevant in models for the cornea, upper lung, and alveolar-capillary interface. Our equipment-free perfusion approach also makes the platform amenable for use in BSL3/4 facilities, where syringe pumps can be difficult to implement because of the risks of aerosol generation and issues arising from problematic decontamination.

The perfusion module can be adapted for any useful flow period and incubation period. For instance, the micro-perfusion module herein was designed to support cell growth over a three-day period. For longer term cultures, the micro-perfusion modules can be replaced periodically or designed with larger fluid reservoirs.

Furthermore, the materials used in the modules (e.g., the perfusion module, seeding module, and/or culture module) can be selected to minimize certain effects, such as evaporation and/or contamination (e.g., by leaching from the material into the cell culture). In this demonstration, microfluidic channels were molded from PDMS and used to seal the channels against the culture insert under magnetic compression and guide fluid flow over the cells. PDMS has several favorable properties including optical clarity and ease of fabrication, but the material also has well known issues related to the partitioning of small hydrophobic molecules into the bulk (see, e.g., Toepke M W et al., "PDMS absorption of small molecules and consequences in microfluidic applications," *Lab Chip* 2006; 6(12):1484-6; and Wang J D et al., "Quantitative analysis of molecular absorption into PDMS microfluidic channels," *Ann. Biomed. Eng.* 2012; 40(9):1862-73). In situations such as small molecule drug candidate testing, other polymers (e.g., polyurethane) with a desired modulus of elasticity (to facilitate sealing) can be used to minimize partitioning effects (see, e.g., Domansky K et al., "Clear castable polyurethane elastomer for fabrication of microfluidic devices," *Lab Chip* 2013; 13(19):3956-64).

Example 5: On-Chip Culture and Stimulation Workflow

The modular approach and removable culture insert in the SEAM platform enabled workflows that combined the microenvironment control of microfluidic systems with the direct cell access provided by open cultures. Culture inserts were reversibly coupled, decoupled, and transferred between specialized microfluidic modules using magnetic latching to achieve several practical advantages. As shown in FIG. 13A, culture inserts were reversibly coupled to seeding modules for precise and economical microscale seeding (FIG. 13A,a), then transferred to the microfluidic culture module for cell culture and exposure studies using the micro-perfusion module (FIG. 13A,b). Following exposure experiments, results (FIG. 13A,d) were obtained from functional readouts (e.g., differential immunostaining of surface proteins) or by transcriptomic readouts (e.g., decoupling the culture insert from the module and transferring it to a commercial off-chip workflow to achieve high quality nucleic acid isolation, FIG. 13A,c) and downstream analysis.

FIG. 13B provides another workflow option. As described schematically in the workflow (FIG. 13B), culture inserts were reversibly coupled to seeding modules for precise microscale seeding (FIG. 13B,a), then transferred to the microfluidic culture module (FIG. 13B,b) for cell culture and LPS stimulation studies using the micro-perfusion module (option 1). Following stimulation, experimental readouts were obtained from differential immunocytochemistry of surface proteins (FIG. 13B,c) or by decoupling the culture insert from the module and transferring it to a commercial off-chip workflow to achieve nucleic acid isolation (FIG. 13B,d).

We employed the well-studied lipopolysaccharide immunoreaction to validate multi-tiered SEAM readouts. The bacterial endotoxin lipopolysaccharide (LPS) is a cell wall component of gram-negative bacteria, and LPS is frequently used to study inflammation during sepsis. LPS is known to activate Toll-like receptor 4 (TLR4) receptors on endothelial cells; induce up-regulation of cell surface adhesion molecules to facilitate neutrophil arrest (see, e.g., Andonegui G et al., "Endothelium-derived Toll-like receptor-4 is the key molecule in LPS-induced neutrophil sequestration into lungs," *J. Clin. Invest.* 2003; 111(7):1011-20); and increase the production of chemokines to recruit and activate dendritic cells and macrophages (see, e.g., Zhang P et al., "Innate immunity and pulmonary host defense," *Immunol. Rev.* 2000; 173:39-51).

Using the workflow shown in FIG. 14, we studied the LPS interaction with primary human microvascular endothelial cells (HMVECs) by seeding HMVECS using the seeding module, as well as incubating and stimulating the cells by employing the culture module to contain the cells and the perfusion module to deliver the LPS stimulant (FIG. 14a). Exposure studies included functional analysis, such as by live cell imaging (FIG. 14b). Furthermore, we decoupled the assembly and released the carrier insert for further transcriptomic analysis (FIG. 14c). Additional details of these experiments follow.

Primary HMVECs were seeded onto the culture region of the insert (surface area=0.05 $cm^2$) using the direct seeding module (1000 cells introduced, corresponding to a seeding density of 20,000 cells $cm^{-2}$). After cell attachment, the culture insert was transferred to the culture module and connected to the micro-perfusion module for 24 hours of culture. The perfusion module was then replaced with a new module, and cells were exposed to LPS through the apical channel for four hours while the basal channel was perfused with culture medium (FIG. 14a).

After stimulation, devices were randomized and selected for ICAM1 immunostaining (FIG. 14b) or RNA extraction downstream gene expression analysis reflecting LPS induced mRNA changes (FIG. 14c). Immunostaining was conducted as follows. Cells were fixed with 4% paraformaldehyde (Sigma-Aldrich Corp., Saint Louis, Mo.) in phosphate-buffered saline (PBS) for 20 minutes followed by permeabilization with 0.1% Triton™ X-100 in PBS for 15 minutes. Cells were then blocked with 2% bovine serum albumin (BSA) in PBS for 2 hours. Primary antibodies against MAP2 (1:000, Sigma-Aldrich Corp.) or ICAM1 (1:40, R&D Systems, Inc., Minneapolis, Minn.) were introduced and incubated for 8 hours at 4° C. The primary antibody solution was removed, and cells were gently rinsed with PBS and then incubated for two hours with secondary antibodies conjugated to Alexa 647 (1:500, Life Technologies, Grand Island, N.Y.) or Qdot 625 (1:500, Life Technologies). Nuclei were stained with DAPI (Life Technologies) at 15 µg mL$^{-1}$. Twelve-bit images were collected through ImagePro software on an Olympus IX-70 microscope with a Photometrics CoolSnap HQ2 camera. Exposure settings were chosen to minimize background fluorescence. Image processing was performed in ImageJ and settings were applied identically to all samples.

After the LPS stimulation, RNA extraction of the cells in the device was performed using the Quick-RNA™ Micro-Prep kit (Cat. No. R1050, Zymo Research Corp., Irvine, Calif.). The culture inserts (and cell layer) were decoupled from the culture modules and immediately submerged in 600 µL of ZR buffer from the MicroPrep kit and centrifuged to lyse all cells. From this point on, the RNA extraction proceeded according to manufacturer's specifications. The RNA was eluted with 10 µL of nuclease free water, and RNA quality was determined using the Agilent RNA 6000 Pico Kit (Cat. No. 5067-1513, Agilent Technologies, Inc., Santa Clara, Calif.). For cDNA synthesis, 5ng of RNA from each sample was used to generate cDNA using the SuperScript® VILO™ cDNA Synthesis Kit (Cat. No. 11754-050, Life Technologies), using manufacturer's recommended conditions. For qPCR, 10 ng of cDNA was used in individual TaqMan® Gene Expression Assays (Applied Biosystems™, Life Technologies). The relative expression of von Willebrand factor (VWF, Cat. No. Hs00169795_m1, Life Technologies), intercellular adhesion molecule 1 (ICAM1, Cat. No. Hs00164932_m1), cadherin 5 (CDH5, Cat. No. Hs00901463_m1), chemokine (C-X-C motif) ligand 1 (CXCL1, Cat. No. Hs00236937_m1), chemokine (C-X-C motif) ligand 2 (CXCL2, Cat. No. Hs00601975_m1), and chemokine (C-C motif) ligand 2 (CCL2, Cat. No. Hs00234140_m1) were analyzed using the ΔΔCt method, with glyceraldehyde-3-phosphate dehydrogenase (GAPDH, Cat. No. Hs99999905_m1) serving as positive control for normalization, and the expression level without LPS stimulation served as basal level. For each cDNA generated, three technical replicates were performed with two controls without template. Determination of threshold Ct at 99% confidence was determined by multiplying the standard deviation of the NTC for each target gene by 6.965.

Significant increases of mRNA expression were found for ICAM1, CXCL1, CXCL2, and CCL2 (FIG. 14c, * p<0.001). ICAM1, a surface adhesion molecule involved in the arrest of rolling leukocytes, was upregulated 2.5 fold while CXCL1 and CXCL2, chemokines involved in the recruitment of neutrophils and lymphocytes, increased 5 fold and 11 fold, respectively (FIG. 14c). CCL2 has been shown to promote dendritic cell and monocyte infiltration and mRNA expression increased 6 fold compared to unstimulated control. The mRNA levels of the endothelial phenotypic marker Von Willebrand Factor (VWF) remained unchanged as expected for healthy control. Staining of ICAM1 between the stimulated and unstimulated cells demonstrated that the mRNA changes were translated to protein level changes in the system. Using the self-contained SEAM platform, we were able to demonstrate mRNA and protein level changes resulting from controlled LPS stimulation.

Figure 15A:
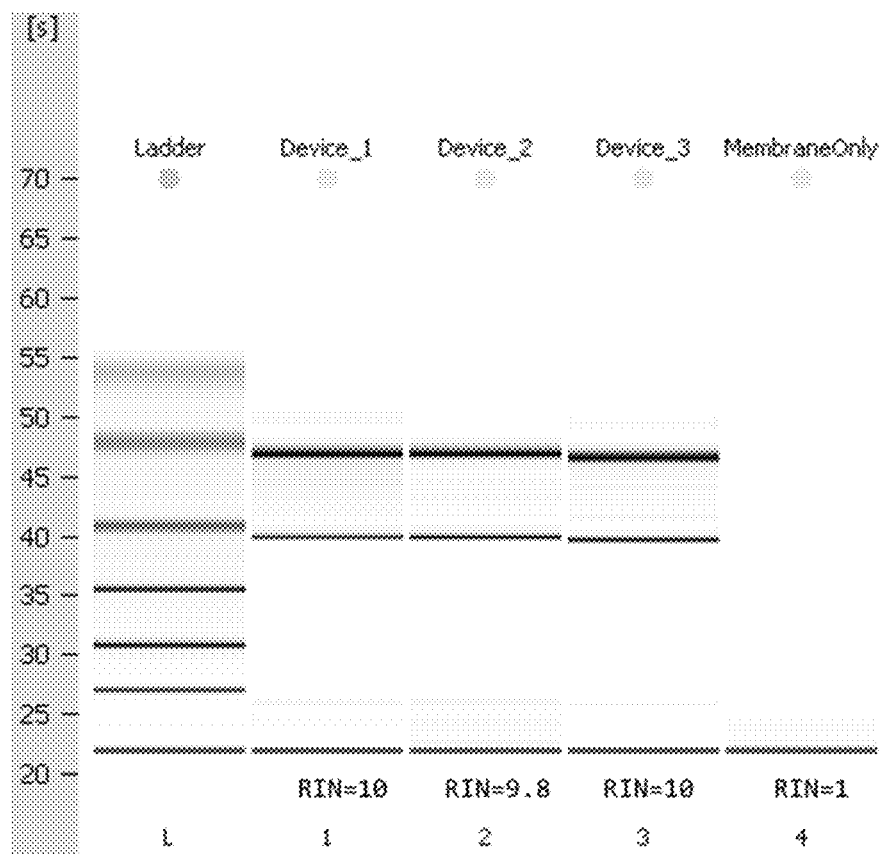
FIG. 15A-15B provides results for off-chip RNA analysis after LPS exposure within the culture module. Shown are RNA quantification using the Bioanalyzer RNA integrity number for off-chip RNA extraction using the culture insert transfer method (FIG. 15A) and a graph showing RNA quantity from on-chip lysis and collection, as compared with the culture insert transfer method (FIG. 15B).
Figure 15B:
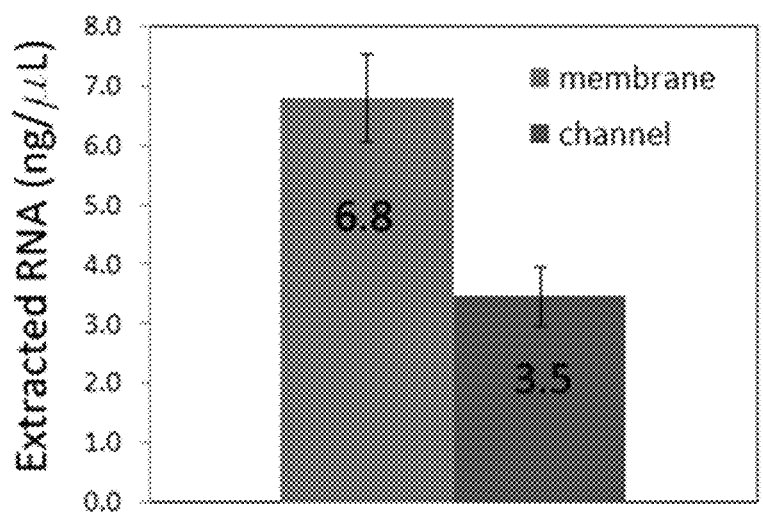

After the experimental exposure, the insert (with entire cell population) was decoupled from the architecture using reversible magnetic latching and transferred directly to the workflow of the off-chip isolation protocol. Decoupling and transferring the culture insert (with attached cells) allowed RNA to be isolated from the entire cell population using optimized commercial off-chip techniques. We successfully achieved high quality RNA isolation (RIN~10, FIG. 15A-15B) from a small initial cell population for downstream analysis. The ability to move an entire cell population without manipulation assisted in limiting sample losses that inevitably occur when transporting cell lysates within high surface-area-to-volume ratio microfluidic channels. Accordingly, this capability provides an avenue for cost effective experimental scale up and supports whole-genome analysis.

Using the transfer approach, we were able to achieve RIN values approaching the maximum value of 10 from a ~1,000 cell input population. Although we demonstrated differential gene expression readouts in this work, transfer of the insert enables a wide variety of optimized commercial techniques, including analysis to explore DNA damage, genotoxicity, and whole genome transcriptomics (e.g., miRNA-Seq or RNA-Seq) that explore global pathway activation patterns that result from the interaction of a drug candidate or pathogen. Although it is well recognized that the activation of a signaling pathway at the mRNA level does not necessarily lead to protein expression and functional response, transcriptomic readouts provide important insights to identify interconnected pathways and components that can be used to assess potential toxicity and guide therapeutic development. In addition, qPCR-based protein assays (e.g., TaqMan® Protein Assays) can be included to the workflow to correlate mRNA expression with protein levels and explore post-translational protein modification. Finally, the removable culture insert can be mounted onto a glass slide for high-resolution imaging of intra-cellular and surface-level protein localization. Accordingly, the assemblies herein use a transferrable insert, which facilitates advanced multi-tiered readouts that provide unique insights into how a tissue or a cell population interacts with an external agent.

Example 6: Incorporation of Alternative Culture Interfaces with Tissue-Specify Properties Although there has been significant progress in the development of biomaterials and tissue scaffolds with well-defined properties (see, e.g., Verhulsel M et al., "A review of microfabrication and hydrogel engineering for micro-organs on chips," *Biomaterials* 2014; 35(6): 1816-32), incorporation of these interfaces into biomimetic organ-on-a-chip platforms has been slow to emerge because incompatibilities between the biomaterials and the fabrication techniques can be used to create permanently sealed systems (e.g., oxygen plasma exposure and bonding).

With reversible magnetic sealing, SEAM architecture can readily incorporate alternative culture interfaces to enhance the physiological relevance of an OC model. Adapting a supramolecular self-assembly chemistry pioneered by Stupp (see, e.g., Beniash E et al., "Self-assembling peptide amphiphile nanofiber matrices for cell entrapment," *Acta Biomater.* 2005; 1(4):387-97; Cui H et al., "Self-assembly of peptide amphiphiles: from molecules to nanostructures to biomaterials," *Biopolymers* 2010; 94(1):1-18; Hartgerink J D et al., "Peptide-amphiphile nanofibers: a versatile scaffold for the preparation of self-assembling materials," *Proc. Nat'l Acad. Sci. USA* 2002(8); 99:5133-8; and Hartgerink J D et al., "Self-assembly and mineralization of peptide-amphiphile nanofibers," *Science* 2001; 294(5547):1684-8, each of which is incorporated herein by reference in its entirety), we prepared an insert including a tethered cell membrane.

Figure 16A:
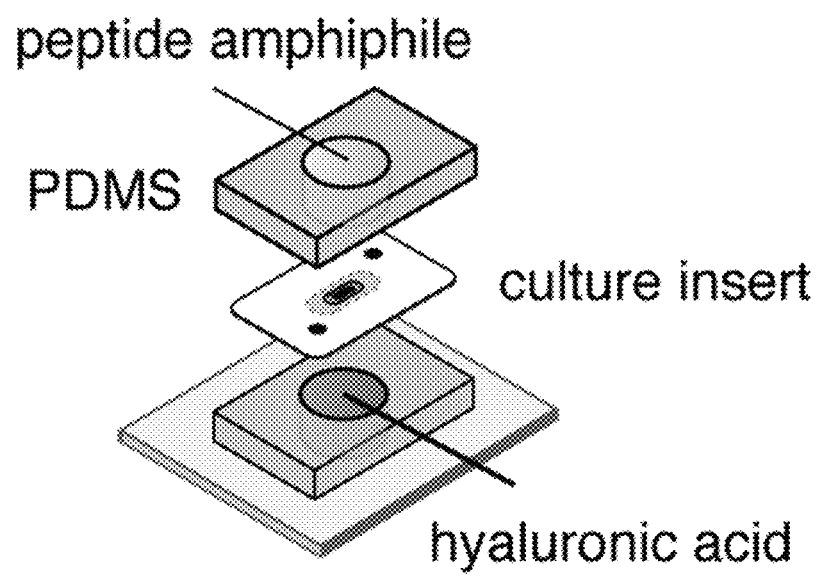
FIG. 16A-16C provides an exemplary culture insert having a self-assembled membrane. Shown is a schematic representation of a system to incorporate a self-assembled membrane into a laminated carrier insert, in which the bottom reservoir is filled with a hyaluronic acid (HA) solution, the carrier insert (with an exposed porous region) is positioned on above the bottom reservoir, and a top PDMS reservoir is placed above the membrane of the insert and filled with a peptide amphiphile (PA) solution (FIG. 16A). The self-assembled (SA) membrane is formed at the interface of the two solutions and tethered to the exposed porous membrane within the carrier insert. The thin, self-assembled membrane and carrier insert was seeded with primary rat neurons (in a SEAM seeding module) and transferred to the culture module (FIG. 16B). After 3 days in culture on the SA membrane, separate membranes were stained for MAP2 (dendritic marker, scale bar=40 µm) and processed for gene expression analysis (FIG. 16C). Gene expression of Neurodap1, NCAM1, TrkA, and c-fos, on the soft self-assembled substrate were closer to rat brain gene expression (dashed horizontal line) than those cultured on rigid substrates.

A carrier insert containing the exposed edge of a laser cut porous membrane (0.1 μm pore diameter, Sterlitech Corp., Kent, Wash.) was fabricated to tether the membrane to the insert (FIG. 16A). Self-assembled membranes were prepared using 3% (wt/v) peptide amphiphile (PA) and 2% (wt/v) hyaluronic acid (HA) in acetate buffer (pH 5.7, 50 mM sodium acetate) with a five-minute contact time. The PA structure contained a palmitic acid tail, a beta sheet forming region, and a charged head group ($C_{15}H_{31}C(O)$-Val$_3$Ala$_3$Lys$_3$ (SEQ ID NO:3)). PA and HA dry weights were corrected for moisture content after analysis by Karl Fisher titration (Sigma-Aldrich Corp.).

Figure 16B:
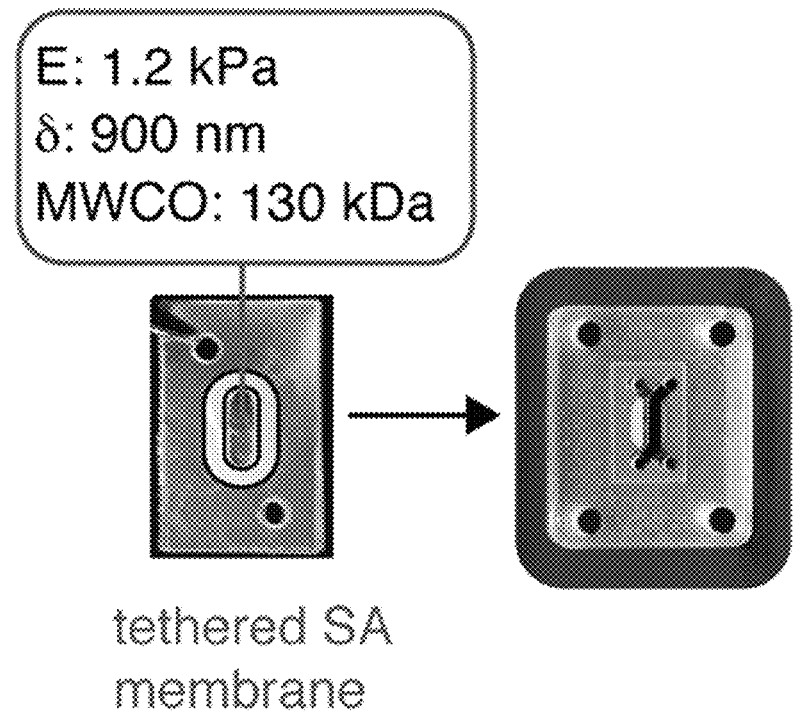
Figure 16C:
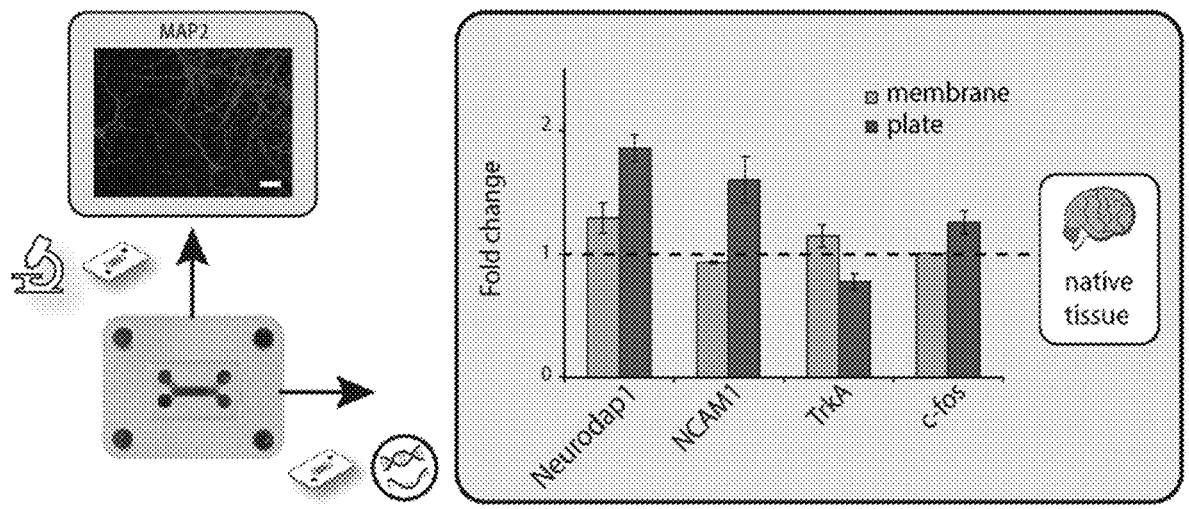

To fabricate the self-assembled membrane, a PDMS reservoir was filled with HA (a large molecular weight component of ECM), and a culture insert was positioned on top. Then, a second PDMS reservoir was placed over the insert and filled with the PA solution (FIG. 16A). When placed in contact with one another, the HA and PA formed a nanofiber complex at their interface with membrane properties that could be tuned as a function of solution concentration and contact time (see, e.g., Capito R M et al., "Self-assembly of large and small molecules into hierarchically ordered sacs and membranes," *Science* 2008; 319:1812-16; and Carvajal D et al., "Physical properties of hierarchically ordered self-assembled planar and spherical membranes," *Soft Matter* 2010; 6:1816-23). After five minutes, the self-assembled membrane became tethered to the porous region of the carrier insert and could be lifted and manipulated (FIG. 16B). After self-assembly, membranes were gently washed in PBS (10 mM sodium phosphate, 150 mM sodium chloride, pH 7.4). Membranes were then mounted onto a cleaned glass coverslip in a fluid cell filled with PBS.

The Young's modulus for the membrane was extracted from a plot of cantilever deflection versus displacement by fitting data to a spherical Hertz contact equation using a pre-calibrated AFM cantilever modified with 0.005 mm spherical probe as described by Soofi S S et al. ("The elastic modulus of Matrigel as determined by atomic force microscopy," *J. Struct. Biol.* 2009; 167(3):216-9). The thickness of the membrane was determined by AFM in contact mode using a silicon nitride probe with tip dimension of 27 nm and 800 nm height (NovoScan). Data were exported in NanoScope Analysis (Bruker) for analysis in Origin Pro (Origin Labs). The molecular weight cutoff of the membrane was determined by quantitating the transport of fluorescently labeled dextrans purchased from Sigma-Aldrich Corp. (10 kDa, 40 kDa, 70 kDa, 120 kDa, and 150 kDa) across the membrane in 24 hours.

Figure 17A:
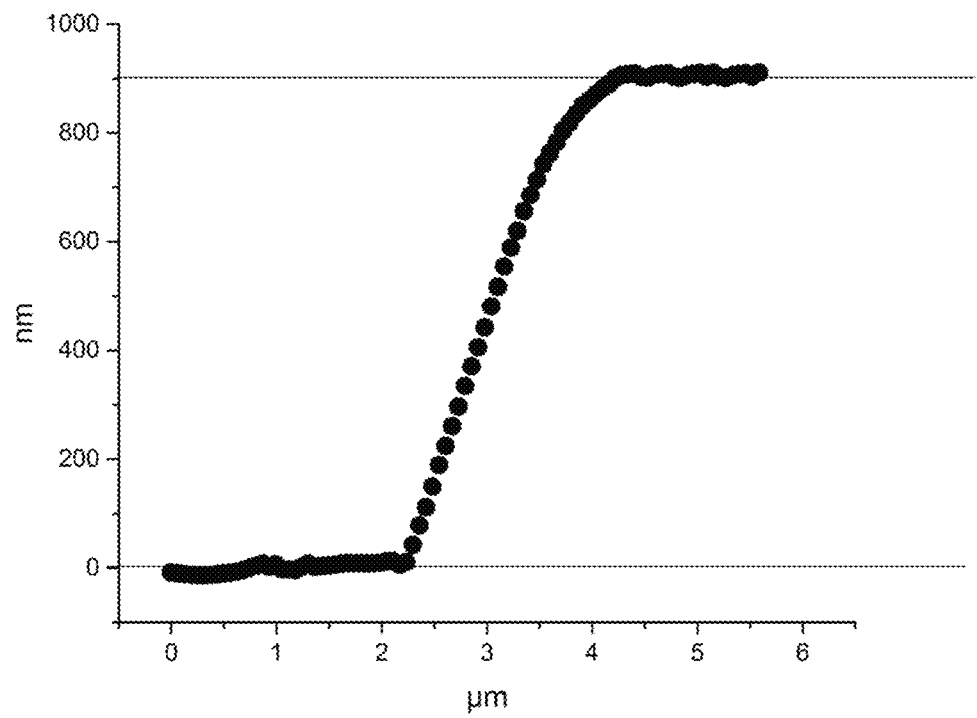
FIG. 17A-17C provides characterization data for a self-assembled membrane formed from a hyaluronic acid and a peptide amphiphile. Shown are a representative atomic force microscopy (AFM) scan used to determine thickness of the self-assembled membrane (FIG. 17A); a representative AFM characterization curve to determine the Young's modulus of the self-assembled membrane (FIG. 17B); and a molecular weight cutoff (90% retention in donor channel) of the membrane determined by quantitating transport of fluorescent dextran across the membrane from a donor to acceptor channel over 24 hours (FIG. 17C).
Figure 17B:
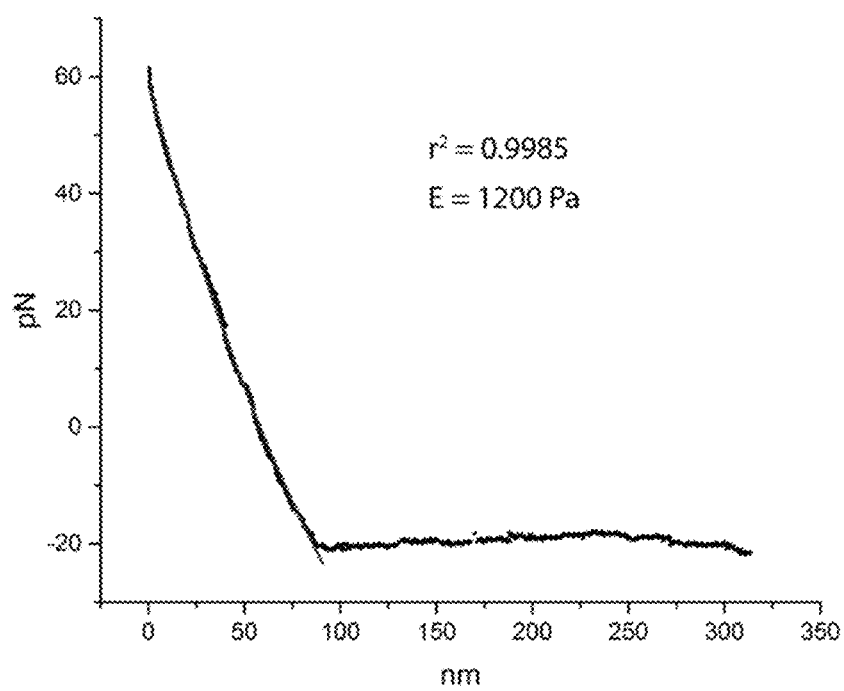
Figure 17C:
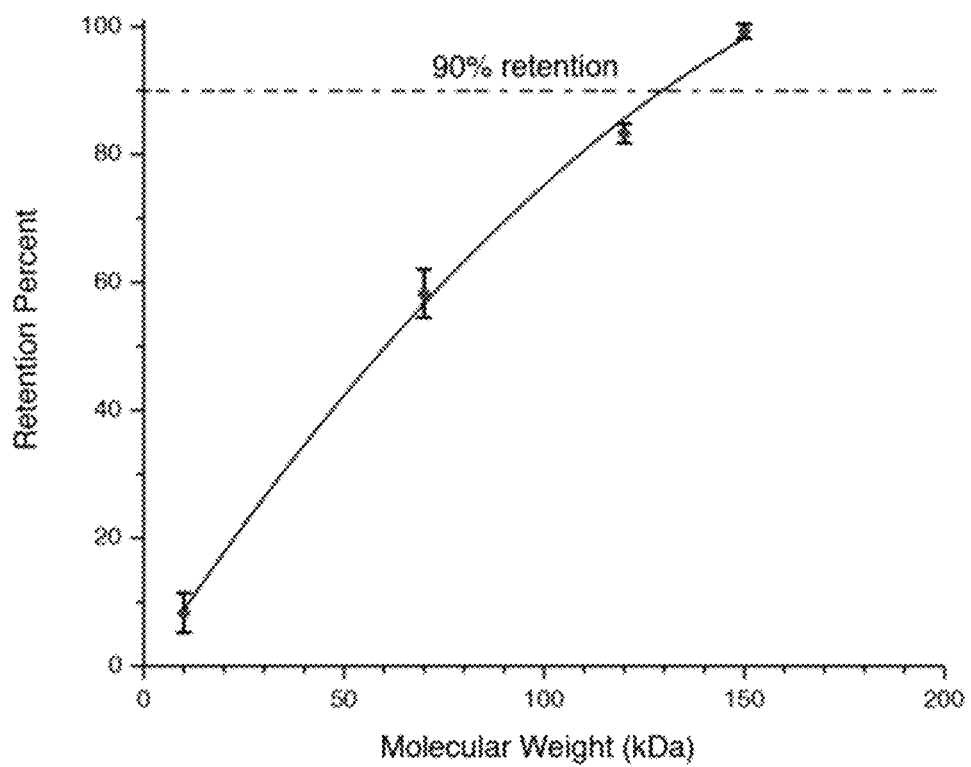

Characterization data are shown in FIG. 17A-17C. AFM analysis showed a membrane thickness of about 900 nm (FIG. 17A) and a Young's modulus of about 1.2 kPa (FIG. 17B). This Young's modulus was similar to the native stiffness of neuronal tissue, see, e.g., Engler A J et al., "Matrix elasticity directs stem cell lineage specification," *Cell* 2006; 126(4):677-89. The molecular weight cut-off (MWCO, 90% retention rate) was determined to be about 130 kDa (FIG. 17C).

To demonstrate the incorporation of a biomimetic culture membrane and explore the effects of substrate stiffness on neuronal gene expression, the self-assembled membrane was seeded with rat cortical neurons and maintained for three days in the culture module. In particular, rat cortical neurons (ScienCell Research Laboratories) were incubated in the seeding module and handled according to manufacturer's instructions. Because of the fragile nature of the neurons, cells were seeded directly into a fibronectin coated polystyrene tissue culture plate (Nunc™ cell-culture dishes, Thermo Scientific) or onto a self-assembled membrane at a density of 30,000 cells cm$^{-2}$.

In one instance, the cerebral cortex or "grey matter" plays an important role in several high level processes including movement and perception. The brain ECM has a unique composition with low percentages of fibrous proteins (e.g. collagen and fibronectin), and high percentages proteoglycans including HA (see, e.g., Ruoslahti E, "Brain extracellular matrix," *Glycobiology* 1996; 6:489-92; and Wang T W et al., "Development of hyaluronic acid-based scaffolds for brain tissue engineering," *Acta Biomater.* 2009; 5:2371-84). To demonstrate SEAM capabilities incorporating biomimetic membranes and isolating nucleic acids, we quantified gene level differences between rat cortical cells grown on a soft suspended HA/PA biomimetic interface with brain specific Young's modulus (~1 kPa) to those grown on a coated rigid plastic surface. As shown in FIG. 16A, the "soft" HA/PA membrane (Young's modulus E~1 kPa) was tethered to the carrier insert using a liquid-liquid self-assembly process.

Figure 18A:
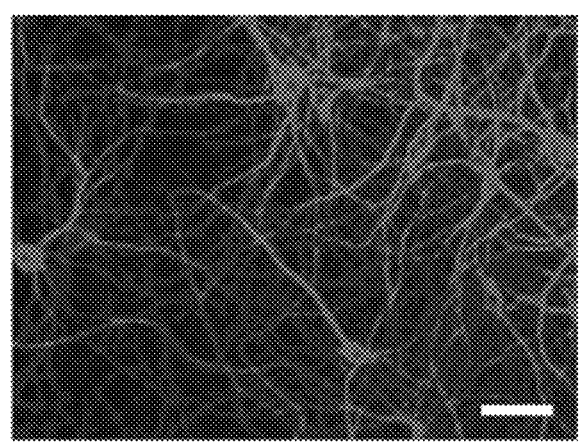
FIG. 18A-18B provides a culture of rat cortical neuron cells on a self-assembled membrane. Shown is a fluorescence microphotograph of neuronal cells after 3 days in culture on the self-assembled membrane, where separate membranes were stained for MAP2 (a dendritic marker and processed for gene expression analysis (FIG. 18A). Scale bar is 50 µm. Also shown is a graph comparing gene expression of Neurodap1, NCAM1, TrkA, and c-fos on two different surfaces: a soft self-assembled membrane (labeled "membrane") or a rigid plate (labeled "plate") (FIG. 18B). The self-assembled membrane provided gene expression levels that were closer to that of native rat brain gene expression (indicated by dashed horizontal line), as compared to gene expression levels for neuron cells cultured on rigid substrates.
Figure 18B:
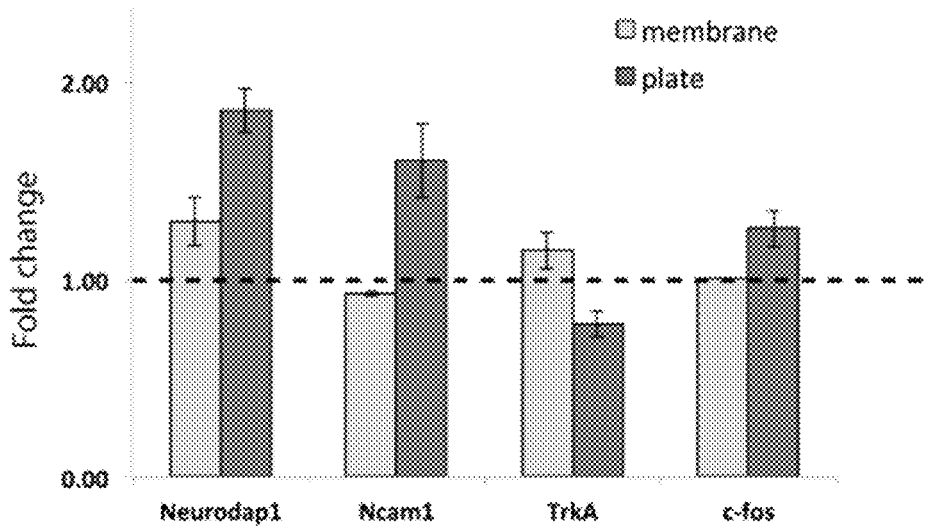

After three days, neuronal cells were either stained for the dendrite marker MAP2 (FIG. 18A); or the culture insert was decoupled from the module and transferred for RNA isolation and downstream gene expression analysis for NeuroDap 1, neuronal adhesion molecule 1 (NCAM-1), c-fos, and tropomyosin receptor kinase A (trkA) (FIG. 18B). NeuroDap 1 is thought to play a role in synaptic communication (see, e.g., Nakayama M et al., "A novel RING-H2 motif protein downregulated by axotomy: its characteristic localization at the postsynaptic density of axosomatic synapse," *J. Neurosci.* 1995; 15(7 Pt 2):5238-48). In addition, NCAM is critical for neuronal adhesion; c-fos is an indirect marker for neuronal activity (see, e.g., Zhang J et al., "c-fos regulates neuronal excitability and survival," *Nat. Genet.* 2002; 30(4):416-20); and trkA is a high affinity receptor for nerve growth factor (NGF) (see, e.g., Geetha T et al., "Nerve growth factor receptor TrkA, a new receptor in insulin signaling pathway in PC12 cells," *J. Biol. Chem.* 2013; 288(33):23807-13). These mRNA targets represent a broad cross-section of adhesion proteins, receptors, and neuronal activity metrics and were chosen to help assess the importance of substrate stiffness from several perspectives.

For RNA isolation, culture inserts were decoupled from the culture module with sterile forceps and placed in 150 μL of RNAzol RT (Molecular Research Center, Inc. Cincinnati, Ohio). From this point on, the RNA extraction proceeded according to manufacturer's instructions. Cells were lysed via pipetting and the solution was centrifuged at 12,000 g for 2 minutes. The supernatant was placed in an RNase-free tube and 150 μL of absolute ethanol was added to the solution. The mixture was vortexed, then placed on a Zymo-Spin™ IC column, and centrifuged at 12,000 g for one minute. The column was then washed and treated with DNase to remove any contaminant DNA. RNA was eluted in 50 μL of ultrapure water. RNA quality was determined using the RNA 6000 kit on the Agilent Bioanalyzer system (Agilent Technologies). For cDNA synthesis, RNA was then reverse transcribed to cDNA using the iScript™ cDNA Synthesis Kit (Bio-Rad Laboratories, Inc., Hercules, Calif.) according to manufacturer's specifications. Each reaction was carried out in duplicate wells with housekeeping genes (GAPDH [5'-VIC], ACTB [5'-FAM], and RPL13A [5'-TET]) detected in multiplex using TaqMan® probes (Applied Biosystems endogenous control sets, Life Technologies) in one well, and the gene of interest detected in the other well using SYBR Green PCR master mix (Life Technologies) on a CFX96 (Bio-Rad Laboratories, Inc.). Gene targets included Neurodap1, NCAM1, c-fos, and trkA.

The ΔΔCt method was used to calculate mRNA quantities relative to housekeeping genes after experimental well factor normalization. For each biological replicate, two reverse transcription reactions were performed with one control without RT. For each cDNA generated, three technical replicates were performed with two controls without template. Determination of threshold Ct at 99% confidence was determined by multiplying the standard deviation of the NTC for each target gene by 6.965. Control experiments using RNA from normal rat brain (Takara/Clontech Laboratories Inc., Mountain View, Calif.) were treated as above to generate data for comparison.

When compared with neurons plated on rigid tissue culture plastic substrates, cells cultured on the self-assembled culture membrane showed interesting and unique similarities to yielded gene expression profiles from RNA isolated from more similar to rat brain tissue (FIG. 18B). The differences in gene expression between the soft biomaterial and the rigid plastic substrates highlighted the importance of including biologically representative culture interfaces that can mimic the tissue microenvironment.

We have demonstrated a novel tethering approach to incorporate a thin, self-assembled HA/PA membrane with stiffness tailored to mimic the brain environment. Our adaptation of nanofiber assembly tethered to a culture insert facilitates handling and manipulation of suspended 900 nm thin membrane throughout the workflow (e.g., seeding, culture, imaging, and nucleic acid isolation).

Thin culture membranes can help accurately represent the dynamics of cell-cell communication across a tissue interface. For example, paracrine signaling factors traveling across a 10 micron culture membrane require 100× longer than with a 900 nm thick membrane. Several barrier tissues (including the alverolar-capillary interface, see, e.g., Bhattacharya J et al., "Regulation and repair of the alveolar-capillary barrier in acute lung injury," *Annu. Rev. Physiol.* 2013; 75:593-615, and blood-brain-barrier, see, e.g., Abbott N.J. et al., "Astrocyte-endothelial interactions at the blood-brain barrier," *Nat. Rev. Neurosci.* 2006; 7(1):41-53) contain polarized cell layers separated by sub-micrometer distances. The ability to include tailored ultra-thin biomaterials provides a unique capability to replicate physiological tissue architectures.

Considerable research has shown that biophysical interactions between a cell and the culture substrate can affect gene expression and drive phenotypic changes (see, e.g., Huynh J et al., "Substrate stiffness regulates PDGF-induced circular dorsal ruffle formation through MLCK," *Cell. Mol. Bioeng.* 2013 June; 6(2); Rehfeldt F et al., "Cell responses to the mechanochemical microenvironment-implications for regenerative medicine and drug delivery," *Adv. Drug Deliv. Rev.* 2007; 59(13):1329-39; Engler A J et al., "Extracellular matrix elasticity directs stem cell differentiation," *J. Musculoskelet. Neuronal Interact.* 2007; 7(4):335; and Engler A J et al., "Myotubes differentiate optimally on substrates with tissue-like stiffness: pathological implications for soft or stiff microenvironments," *J. Cell. Biol.* 2004; 166(6):877-87). We observed this phenomenon in our demonstration exploring gene level changes in rat neurons cultured on soft and rigid interfaces. The long-term implications of these gene level changes can be explored in more detail, and the SEAM architecture provides a convenient approach to include advanced biological interfaces within an organ-on-a-chip platform to help enhance the biomimetic aspect of in vitro assays.

Example 7: Transferrable Inserts Including Suspended Ultrathin Self-Assembled Membranes We have advanced the ability to form and manipulate suspended ultrathin self-assembled sheets. The device and methods herein can include a pre-defined boundary of a suspended membrane using a handling layer (e.g., a porous or fibrous scaffolding support layer) and for manipulating the membrane by manipulating the support layer (e.g., picking up the membrane layer with tweezers, rinsing the membrane, placing the membrane in a microfluidic device, stacking membranes in customized 3D architectures complete with microfluidic inlets and outlets interfacing with the membrane, and later removing the membrane from microfluidic devices or modules).

In one instance, the transferrable insert includes a handling layer and an aperture defined within that layer. Then, a cell culture membrane can be disposed within the aperture. The cell culture membrane can include any useful material. In one instance, the cell culture membrane itself acts as a substrate for cell growth. This cell culture membrane can be a self-assembled polymer membrane (e.g., a membrane including a plurality of nanofibers, such as nanofibers composed of a peptide amphiphile and optionally a protein). In another instance, the cell culture membrane acts as a scaffold (e.g., a porous scaffold), and this scaffold in turn is used to support a polymer membrane (e.g., a self-assembled polymer including a plurality of nanofibers, such as nanofibers composed of a peptide amphiphile and optionally a protein).

Figure 19A:
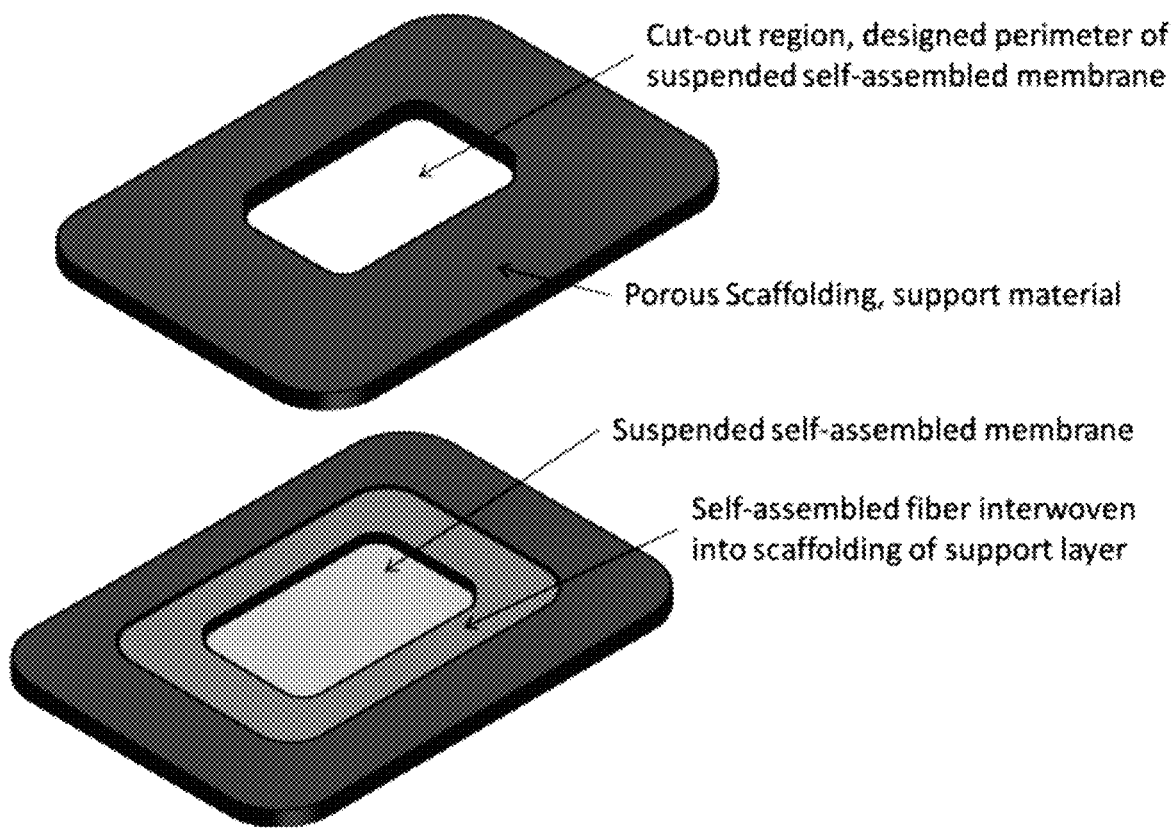
FIG. 19A-19D provides an exemplary self-assembled membrane configured to be suspended within a handling layer and optionally stacked. Shown is a schematic representation of a self-assembled membrane that is suspended across an aperture cut into a 10 μm thick polyester membrane (FIG. 19A). Cell layers can be seeded and cultured independently on separate layers and then stacked to form integrated multi-cellular systems. Also shown are an image of self-assembled membranes that are readily incorporated into microfluidic architectures either before or following initial culture of cell layers (FIG. 19B); and an image of a two compartment microfluidic architecture, which is separated by a suspended, self-assembled membrane (dashed box) (FIG. 19C). Microfluidic channels can provide independent access to the upper and lower compartments facilitating the construction of, e.g., an alveolar-capillary model complete with simulated flow of gas through the alveolar gas-liquid interfacial compartment and simulated blood flow through the endothelial compartment. Primary alveolar epithelial cells were cultured within microfluidic channel, where shown is a fluorescence microphotograph of cells treated with a nuclear stain (gray regions, as indicated by dotted line) and an occludin stain (white regions, as indicated by white arrowheads), which indicates formation of tight junctions (FIG. 19D).

An opening or aperture in the handling layer, within which the membrane is formed, can be laser-cut into a planar porous sheet of support material (FIG. 19A). This support material can be chosen from some membranes currently in use for tissue engineering. The aperture and the edges of the forming support material can be brought into contact with the solutions used to form the membrane by a self-assembly process using a platen. The self-assembled membrane can be of any appropriate thickness, e.g., about 1 μm thick membrane. The self-assembled membrane can be suspended across an aperture cut into a handling layer (e.g., a 10 μm thick polyester membrane).

The support material provides a robust way for handling the membrane sheet, aiding integration within microfluidic devices and tissue layers, and suspending membranes within a device. Preferred, non-limiting embodiments include a porous support membrane measuring within ~1-2 orders of magnitude of the desired thickness of the suspended membrane and preferably within ~1 order of magnitude the desired thickness. For example, a 1 μm membrane has been successfully formed and manipulated using a 10 μm porous sheet as the support, scaffolding layer during the self-assembly process.

A preferred, non-limiting embodiment of the device includes a scaffolding support layer material that is porous and compatible with entry or penetration of self-assembly fluids including peptide amphiphile and negatively charged long chain biomolecule precursors. The support material can be compatible with self-assembly of membrane fibers within the support scaffolding matrix during the same self-assembly step that forms the suspended membrane in the cavity of the supporting material. In one instance, the assembled fibers adhere to or are entangled with the support matrix providing strong anchoring of the suspended self-assembled membrane to the support matrix and a non-leaking boundary along the periphery of the membrane/scaffold interface.

The self-assembled membrane provides a way to control various physical and structural aspects of the cell culture membrane, which in turn can affect the way in which the deposited cell population can proliferate or grow. For instance, lung tissue includes alveolar compartment that are separated from vascular compartments by tissue having a thickness of about 1 µm with a cell layer on each side. Attempts to reproduce lung tissue currently require non-biological materials that are about 10 µm or greater in thickness. This is a technical limitation on the ability to form strong suspended tissue engineering scaffolds. The membranes herein provide an ultrathin (e.g., less than about 2 µm) self-assembled interface that is fully composed of natural biomaterial.

In addition, any useful dimension of the membrane can be customized. For instance, it can be customized for its thickness, as well as tailored with an elasticity and/or stress modulus relevant for tissue engineering and/or for expansion/contraction forces (e.g., as present in lung tissue) by physiologically relevant pressure inputs rather than by mechanical means. We have reproducibly assembled and characterized membranes of 1 µm thickness, which better mimics the in vivo anatomical structure than conventional approaches for tissue engineering that are generally at least 10 times thicker. This is significant with respect to cell-to-cell signaling between tissue layers, e.g., lung epithelial and vascular interfaces as diffusive transport of signaling molecules scale with length squared resulting in 100-fold difference affecting not only timing of signaling interactions but also significant dilution of the signaling molecules near perfusion interfaces (vascular compartment).

We have demonstrated the formation of suspended self-assembled membranes using porous support material using chemistries described by Stupp and coworkers using peptide amphiphiles (PAs). PA self-assembly can be used to develop biomaterials with controlled architecture, definable material properties, and tailored bioadhesive functions (see, e.g., Hartgerink J D et al., "Peptide-amphiphile nanofibers: a versatile scaffold for the preparation of self-assembling materials," *Proc. Nat'l Acad. Sci.* USA 2002(8); 99:5133-8; Storrie H et al., "Supramolecular crafting of cell adhesion," *Biomaterials* 2007; 28(31):4608-18; Capito R M et al., "Self-assembly of large and small molecules into hierarchically ordered sacs and membranes," *Science* 2008; 319: 1812-16; and Carvajal D et al., "Physical properties of hierarchically ordered self-assembled planar and spherical membranes," *Soft Matter* 2010; 6:1816-23, each of which is incorporated herein by reference in its entirety).

In some embodiments, PAs contain three distinct regions that include (i) a hydrophobic tail, (ii) a beta sheet forming sequence, and (iii) a head group containing a functional epitope (e.g., a charged or bioadhesive sequence). In aqueous solutions, self-assembly occurs via hydrophobic collapse of the tail region (thus presenting the functional epitope) and hydrogen bonding between the beta sheet forming sequence. Hierarchical self-assembled sheets or closed gel sacs can be rapidly formed (e.g., within minutes) by interfacial contact with negatively charged long chain biomolecules (LCBs). Applications of self-assembled biomaterials include angiogenesis, neural cell differentiation, and bone regeneration (see, e.g., Chow L W et al., "A bioactive self-assembled membrane to promote angiogenesis," *Biomaterials* 2011; 32:1574-82; Silva G A et al., "Selective differentiation of neural progenitor cells by high-epitope density nanofibers," *Science* 2004; 303(5662):1352-5; and Mata A et al., "Bone regeneration mediated by biomimetic mineralization of a nanofiber matrix," *Biomaterials* 2010; 31(23):6004-12, each of which is incorporated herein by reference in its entirety).

Figure 19B:
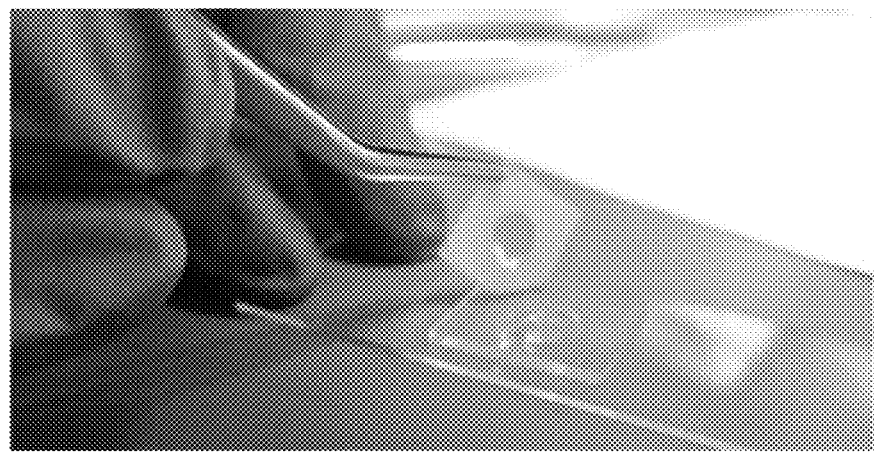

We advanced the self-assembly fabrication process to provide facile incorporation of suspended PA nanofiber membranes. Suspending the membranes within microfluidic architectures provides a well-defined compartmentalized culture environment. The new methods are also robust enough that cell layers on these membranes can be readily stacked. A thin (about 1 µm) self-assembled membrane formed from an interfacial fabrication process is shown in FIG. 19B.

We iterated through a range of customized PAs and LCBs to realize a combination that delivered reproducible membranes possessing the required mechanical properties and cell/tissue compatibility. These membranes have excellent mechanical properties allowing for the first known demonstration of stacking and suspending of self-assembled peptide-amphiphile sheets. To create planar membranes of a desired geometry, we used custom platens to laminate the two solutions (PA and LCB) and to allow the interfacial self-assembly process to occur while controlling the membrane thickness via time allowed for self-assembly.

Figure 19C:
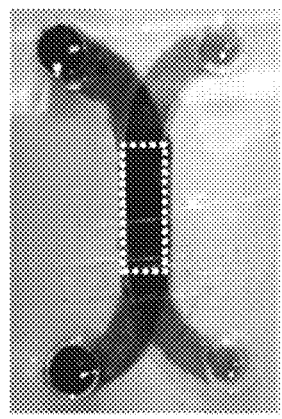

Our advanced methods provide a means for straightforward manipulation of the self-assembled membranes for advanced tissue engineering with suspended or stacked cell layers. As shown in FIG. 19C, the self-assembled membrane is also readily sandwiched between two microfluidic channels. The presence of the suspended membrane prohibited bulk fluid mixing but supported molecular transport between compartments (e.g., growth factors and/or cytokines).

Figure 19D:
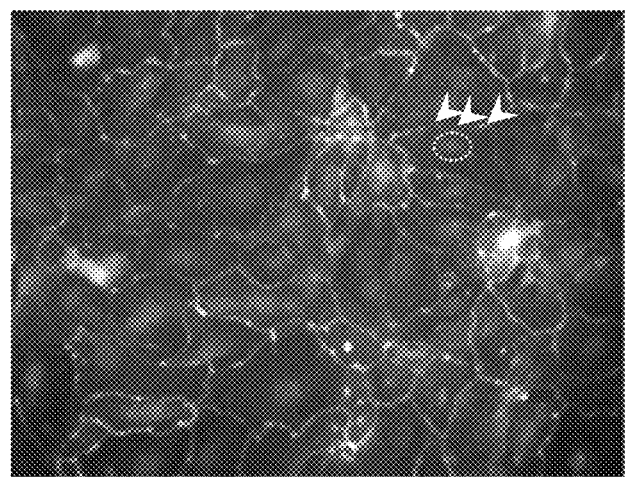

We have successfully cultured primary human cell populations on the membrane material, including small airway epithelial cells, primary microvascular endothelial cells, and primary alveolar epithelial cells (FIG. 19D). Membranes containing unique cell populations can be combined within the architecture to produce a complex biological interface that can maintain appropriate basal to apical cell polarity (e.g., alveolar-capillary interface). Self-assembled membranes have an advantage over conventional porous media in that they are thin (about 1 µm vs. more than about 10 µm) with tunable mechanical properties and customizable bioadhesive properties. The thickness is highly relevant in capturing cell-cell signaling. For example, the thickness closely represents an alveolar-capillary wall whereas even a 10 µm thick alternative would generate 100-fold slower cross-membrane signaling responses linked to differences in diffusive transport that scale with thickness squared.

We have also observed in preliminary studies that pressures applied directly to the alveolar or capillary compartment can approximate to some extent deflation and inflation of the suspended compliant membrane and tissue layer. As both the extent of stretching/relaxing and pressure-volume curves across breathing cycles are important to lung function and also vary in health vs. disease, tailoring the tissue mechanics to best approximate known characteristics (e.g., level of distention across known lung P-V curve) may be important in representing the organ system (see, e.g., Fahlman A et al., "Static inflation and deflation pressure-volume curves from excised lungs of marine mammals," *J. Exp. Biol.* 2011; 214(Pt 22):3822-8; and Harris RS, "Pressure-volume curves of the respiratory system," *Respir. Care* 2005; 50(1):78-99). By implementing designs using a compliant membrane with tailorable mechanical properties (adjusting membrane thickness, properties of the self-assembling peptide amphiphile, and/or chemical modifications after assembly) and directly simulating both P-V and expansion/relaxation, there is potential to further optimize the system to more accurately capture fundamental characteristics and responses to a variety of conditions.

To form self-assembled nanofiber tubes, we propose the following options. A solid rod with diameter approximating the desired tube diameter is coated with PA and then immersed in a bath of the LCB. A PA nanofiber membrane self-assembles at the interfacial layer formed around the tube. The two ends of the nanofiber tubing are secured to ports within the desired structure and the rod is then removed. Alternatively, a porous rod material such as a hydrogel with stimuli responsive crosslinks is used in place of a solid rod. The PA solution can be soaked into the porous rod before immersion into LCB solution. After securing the ends of the formed tube into the desired structure, the porous material is degraded. A third option is to form a flat, long-rectangular membrane and then roll the membrane into a tube using a small rod.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A modular assembly comprising:
a transferrable cell culture insert, wherein the transferrable insert comprises:
   a handling layer, wherein a portion of the handling layer is composed of a non-porous material,
   an aperture disposed within the handling layer;
   a rim comprising a stepped region and disposed around a periphery of the aperture within the handling layer, wherein the rim is composed of a porous material;
   a cell culture membrane disposed within the aperture and tethered to the rim;
   and at least two vias;
a top housing comprising one or more access ports, wherein at least one access port is in fluidic communication with the cell culture membrane;
a bottom housing, wherein the top and bottom housing are configured to accommodate the transferrable insert;
a top sealing layer disposed between the top housing and the transferrable insert, wherein the top sealing layer comprises a channel disposed between two vias, wherein at least one via of the top sealing layer is in fluidic communication with at least one via of the transferrable insert, and wherein the channel in the top sealing layer is in fluidic communication with a top surface of the cell culture membrane;
a bottom sealing layer disposed between the transferrable insert and the bottom housing, wherein the bottom sealing layer comprises a channel disposed between two vias, wherein at least one via of the bottom sealing layer is in fluidic communication with at least one via of the transferrable insert, and wherein the channel in the bottom sealing layer is in fluidic communication with a bottom surface of the cell culture membrane; and
one or more fasteners disposed within the top housing, within the bottom housing, and/or between the top and bottom housing, wherein the top and bottom housing are configured to be reversibly detached, thereby facilitating transfer of the transferrable insert.

2. The modular assembly of claim 1, wherein the one or more fasteners comprises one or more adhesive layers, wherein at least one adhesive layer is disposed between the top housing and the transferrable insert and/or between the transferrable insert and the bottom housing, and wherein at least one adhesive layer comprises a reversible sealing material.

3. The modular assembly of claim 1, wherein the one or more fasteners comprises a first fastener disposed within the top housing and a second fastener disposed within the bottom housing, wherein the first fastener and the second fastener are configured to be reversibly attached to each other.

4. The modular assembly of claim 3, wherein the bottom housing further comprises a recess configured to accommodate the transferrable insert.

5. The modular assembly of claim 1, further comprising:
a recess within the bottom housing further configured to accommodate the transferrable insert affixed to the top sealing layer and to the bottom sealing layer, wherein the top sealing layer and the bottom sealing layer are configured to be reversibly affixed to the transferrable insert and to form a seal between the transferrable insert, the top housing, and the bottom housing.

6. The modular assembly of claim 5, wherein the at least one via of the top sealing layer is in fluidic communication with the at least one via of the transferrable insert and at least one access port of the top housing.

7. The modular assembly of claim 1, further comprising:
a fluidics layer comprising a channel and a via, wherein the fluidics layer is disposed between the top sealing layer and the top housing, and wherein the via of the fluidics layer is in fluidic communication with at least one access port of the top housing, and wherein further the channel of the fluidic layer is in fluidic communication with the channel of the top sealing layer.

8. The modular assembly of claim 1, wherein the cell culture membrane comprises a porous substrate, and wherein the handling layer is rigid.

9. The modular assembly of claim 8, wherein the transferrable insert comprises a laminated structure, the handling layer comprising a top handling layer having a first aperture, and a bottom handling layer having a second aperture, and wherein the cell culture membrane is disposed between the top and bottom handling layers and positioned between the first and second apertures; and wherein the top handling layer, the cell culture membrane, and the bottom handling layer are positioned such that the first aperture and the second aperture form the aperture of the transferrable insert and are laminated.

10. The modular assembly of claim 1, further comprising a perfusion module configured to be reversibly attached to the top housing and configured to be in fluidic communication with at least one access port of the top housing.

11. The modular assembly of claim 1, wherein the cell culture membrane comprises a self-assembled peptide amphiphile in the presence of an extracellular matrix protein, a saccharide, or a carbohydrate.

12. A modular assembly comprising:
 a transferrable cell culture insert, wherein the transferrable insert comprises a non-porous handling layer, an aperture disposed within the handling layer, a porous rim comprising a stepped region and disposed around a periphery of the aperture within the handling layer, a cell culture membrane disposed within the aperture and tethered to the rim, a first via, and a second via;
 a top housing comprising a first access port, a second access port, a third access port, and a fourth access port, wherein at least one access port is in fluidic communication with the cell culture membrane;
 a bottom housing, wherein the top and bottom housing are configured to accommodate the transferrable insert and to be reversibly attached, thereby facilitating transfer of the transferrable insert;
 a top sealing layer disposed between the top housing and the transferrable insert, wherein the top sealing layer comprises a channel disposed between a first via and a second via, a third via, and a fourth via; wherein the third via of the top sealing layer is in fluidic communication with the first via of the transferrable insert; wherein the fourth via of the top sealing layer is in fluidic communication with the second via of the transferrable insert; and wherein the channel in the top sealing layer is in fluidic communication with a top surface of the cell culture membrane;
 a bottom sealing layer disposed between the transferrable insert and the bottom housing, wherein the bottom sealing layer comprises a channel disposed between a first via and a second via; wherein the first via of the bottom sealing layer is in fluidic communication with the first via of the transferrable insert; wherein the second via of the bottom sealing layer is in fluidic communication with the second via of the transferrable insert; and wherein the channel in the bottom sealing layer is in fluidic communication with a bottom surface of the cell culture membrane; and
 one or more fasteners disposed within the top housing, within the bottom housing, and/or between the top and bottom housing.

13. The modular assembly of claim 12, wherein the first access port is in fluidic communication with the first via of the top sealing layer; wherein the second access port is in fluidic communication with the second via of the top sealing layer; wherein the third access port is in fluidic communication with the third via of the top sealing layer, the first via of the transferrable insert, and the first via of the bottom sealing layer; and wherein the fourth access port is in fluidic communication with the fourth via of the top sealing layer, the second via of the transferrable insert, and the second via of the bottom sealing layer.

14. The modular assembly of claim 12, wherein the one or more fasteners comprises one or more adhesive layers, wherein at least one adhesive layer is disposed between the top housing and the transferrable insert and/or between the transferrable insert and the bottom housing, and wherein at least one adhesive layer comprises a reversible sealing material.

15. The modular assembly of claim 12, further comprising:
 a fluidics layer comprising a channel and a via, wherein the fluidics layer is disposed between the top sealing layer and the top housing, and wherein the via of the fluidics layer is in fluidic communication with at least one access port of the top housing, and wherein further the channel of the fluidic layer is in fluidic communication with the channel of the top sealing layer.

16. The modular assembly of claim 12, wherein the cell culture membrane comprises a porous substrate, and wherein the handling layer is substantially rigid.

17. The modular assembly of claim 16, the handling layer comprising a top handling layer having a first aperture, a bottom handling layer having a second aperture, the first aperture and the second aperture aligned to form the aperture of the handling layer, and wherein the cell culture membrane is disposed between the top and bottom handling layers and positioned between the first and second apertures; and wherein the top handling layer, the cell culture membrane, and the bottom handling layer are positioned and laminated.

18. The modular assembly of claim 12, further comprising a perfusion module configured to be reversibly attached to the top housing and configured to be in fluidic communication with at least one access port of the top housing.

19. The modular assembly of claim 12, wherein the one or more fasteners comprises a magnet or a ferromagnetic metal.

20. A modular assembly comprising:
 a transferrable cell culture insert, comprising:
  a handling layer having a non-porous outer portion;
  an aperture disposed within the handling layer;
  a porous rim disposed around a periphery of the aperture; and
  a cell culture membrane disposed within the aperture and tethered to the rim;
 a top housing comprising a first access port;
 a bottom housing, wherein the top and bottom housing are configured to accommodate the transferrable cell culture insert and to be reversibly attached to one another;
 a fluidics layer comprising a first channel and a first via that is in fluidic communication with the first access port and the first channel, wherein the fluidics layer is disposed between the top housing and the transferable cell culture insert;
 a top sealing layer disposed between the fluidics layer and the transferrable cell culture insert, wherein the top sealing layer comprises a second channel that is in fluidic communication with a top surface of the cell culture membrane and with the first channel of the fluidics layer; and
 a bottom sealing layer disposed between the transferrable insert and the bottom housing.

21. The modular assembly of claim 20, wherein the top sealing layer comprises a second via and the handling layer comprises a third via, the second and third vias in fluidic communication with the first channel, the bottom sealing layer comprising a third channel that is in fluidic communication with the third via and with a bottom surface of the cell culture membrane.

22. The modular assembly of claim 20, wherein the handling layer is a rigid layer.

\* \* \* \* \*

SEQUENCE LISTING

```
<160> NUMBER OF SEQ ID NOS: 14

<210> SEQ ID NO 1
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 1

Val Val Val Ala Ala Ala
1               5

<210> SEQ ID NO 2
<211> LENGTH: 7
<212> TYPE: PRT
<213> ORGANISM: Artificial Sequence
<220> FEATURE:
<223> OTHER INFORMATION: Sythetic Sequence

<400> SEQUENCE: 2

Ala Ala Ala Ala Gly Gly Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (1)..(1)
<223> OTHER INFORMATION: palmitic acid tail (C15H31C(O))

<400> SEQUENCE: 3

Val Val Val Ala Ala Ala Lys Lys Lys
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (1)..(1)
<223> OTHER INFORMATION: X as described in the Specification
<220> FEATURE:
```

```
<221> NAME/KEY: MOD_RES
<222> LOCATION: (9)..(9)
<223> OTHER INFORMATION: Y as described in the Specification

<400> SEQUENCE: 4

Val Val Val Ala Ala Ala Lys Lys Lys
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (1)..(1)
<223> OTHER INFORMATION: X as described in Specification
<220> FEATURE:
<221> NAME/KEY: MOD_RES
<222> LOCATION: (6)..(6)
<223> OTHER INFORMATION: Y as described in Specification

<400> SEQUENCE: 5

Val Val Val Ala Ala Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (1)..(1)
<223> OTHER INFORMATION: X as described in Specification
<220> FEATURE:
<221> NAME/KEY: MOD_RES
<222> LOCATION: (7)..(7)
<223> OTHER INFORMATION: Y as described in Specification

<400> SEQUENCE: 6

Ala Ala Ala Ala Gly Gly Gly
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (1)..(1)
<223> OTHER INFORMATION: X as described in Specification
<220> FEATURE:
<221> NAME/KEY: MOD_RES
<222> LOCATION: (6)..(6)
<223> OTHER INFORMATION: Y as described in Specification

<400> SEQUENCE: 7

Ala Ala Ala Leu Leu Leu
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Sequence
```

```
<220> FEATURE:
<221> NAME/KEY: MOD_RES
<222> LOCATION: (1)..(1)
<223> OTHER INFORMATION: X as described in Specification
<220> FEATURE:
<221> NAME/KEY: MOD_RES
<222> LOCATION: (8)..(8)
<223> OTHER INFORMATION: Y as described in Specification

<400> SEQUENCE: 8

Ala Ala Ala Leu Leu Leu Glu Glu
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (1)..(1)
<223> OTHER INFORMATION: X as described in Specification
<220> FEATURE:
<221> NAME/KEY: MOD_RES
<222> LOCATION: (8)..(8)
<223> OTHER INFORMATION: Y as described in Specification

<400> SEQUENCE: 9

Ala Ala Ala Leu Leu Leu Lys Lys
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (1)..(1)
<223> OTHER INFORMATION: X as described in Specification
<220> FEATURE:
<221> NAME/KEY: MOD_RES
<222> LOCATION: (8)..(8)
<223> OTHER INFORMATION: Y as described in Specification

<400> SEQUENCE: 10

Ala Ala Ala Leu Leu Leu Glu Glu
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 11

Glu Ile Lys Val Ala Val
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 12
```

```
Ile Lys Val Ala Val
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 13

Glu Arg Gly Asp
1

<210> SEQ ID NO 14
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 14

Arg Gly Asp Ser
1
```